US011866474B2

(12) United States Patent
Cai et al.

(10) Patent No.: US 11,866,474 B2
(45) Date of Patent: Jan. 9, 2024

(54) MODULATING ANGIOGENESIS BY PROTEOMIMETICS OF VASCULAR ENDOTHELIAL GROWTH FACTOR

(71) Applicant: UNIVERSITY OF SOUTH FLORIDA, Tampa, FL (US)

(72) Inventors: Jianfeng Cai, Tampa, FL (US); Sami Abdulkadir, Tampa, FL (US)

(73) Assignee: UNIVERSITY OF SOUTH FLORIDA, Tampa, FL (US)

( * ) Notice: Subject to any disclaimer, the term of this patent is extended or adjusted under 35 U.S.C. 154(b) by 0 days.

(21) Appl. No.: 18/069,797

(22) Filed: Dec. 21, 2022

(65) Prior Publication Data

US 2023/0220028 A1  Jul. 13, 2023

Related U.S. Application Data

(60) Provisional application No. 63/265,835, filed on Dec. 21, 2021.

(51) Int. Cl.
*C07K 14/475* (2006.01)
*A61P 9/00* (2006.01)
*A61K 38/00* (2006.01)

(52) U.S. Cl.
CPC .............. *C07K 14/475* (2013.01); *A61P 9/00* (2018.01); *A61K 38/00* (2013.01)

(58) Field of Classification Search
CPC .......... C07K 14/475; A61P 9/00; A61K 38/00
See application file for complete search history.

(56) References Cited

PUBLICATIONS

Sang et al., 2019, Inhibition of beta-catenin/B cell lymphoma 9 protein-protein interaction using alpha-helix-mimicking sulfono-gamma-AApeptide inhibitors, PNAS, 116(22): 10757-10762.*
Akram, O. N.; DeGraff, D. J.; Sheehan, J. H.; Tilley, W. D.; Matusik, R. J.; Ahn, J. M.; Raj, G. V., Tailoring peptidomimetics for targeting protein-protein interactions. *Mol. Cancer Res.* 2014, 12 (7), 967-78.
Anisimov, A.; Leppänen, V.M.; Tvorogov, D.; Zarkada, G.; Jeltsch, M.; Holopainen, T.; Kaijalainen, S.; Alitalo, K., The basis for the distinct biological activities of vascular endothelial growth factor receptor-1 ligands. *Sci. Signal.* 2013, 6 (282), ra52-ra52, 1-11.
Arvidsson, P. I.; Frackenpohl, J.; Ryder, N. S.; Liechty, B.; Petersen, F.; Zimmermann, H.; Camenisch, G. P.; Woessner, R.; Seebach, D., On the antimicrobial and hemolytic activities of amphiphilic beta-peptides. *ChemBioChem* 2001, 2 (10), 771-3.
Basile, A.; Del Gatto, A.; Diana, D.; Di Stasi, R.; Falco, A.; Festa, M.; Rosati, A.; Barbieri, A.; Franco, R.; Arra, C., Characterization of a designed vascular endothelial growth factor receptor antagonist helical peptide with antiangiogenic activity in vivo. *J. Med. Chem.* 2011, 54 (5), 1391-1400.
Bergers, G.; Benjamin, L. E., "Tumorigenesis and the angiogenic switch." *Nature reviews cancer* 3.6 (2003): 401-410.
Bolarinwa, O.; Nimmagadda, A.; Su, M.; Cai, J., Structure and Function of AApeptides. *Biochemistry* 2017, 56 (3), 445-457.

Bolarinwa, O.; Zhang, M.; Mulry, E.; Lu, M.; Cai, J., Sulforto-γ-AA modified peptides that inhibit HIV-1 fusion. *Org. Biomol. Chem.* 2018, 16 (42). 7878-7882.
Brem, H.; Folkman, J., Inhibition of tumor angiogenesis mediated by cartilage. *The Journal of Experimental Medicine* 1975, 141 (2), 427-439.
Brozzo, M. S.; Bjelić, S.; Kisko, K.; Schleier, T.; Leppänen, V.-M.; Alitalo, K.; Winkler, F. K.; Ballmer-Hofer, K., Thermodynamic and structural description of allosterically regulated VEGFR-2 dimerization. *Blood* 2012, 119 (7), 1781-88.
Bullock, B. N.; Jochim, A. L.; Arora, P. S., Assessing Helical Protein Interfaces for Inhibitor Design. *J. Am. Chem. Soc.* 2011, 133 (36), 14220-14223.
Byrne, A. M.; Bouchier-Hayes, D. J.; Harmey, J. H., Angiogenic and cell survival functions of vascular endothelial growth factor (VEGF). *J. Cell Mol. Med.* 2005, 9 (4), 777-94.
Carmeliet, P.; Jain, R. K., Angiogenesis in cancer and other diseases. *Nature* 2000, 407 (6801), 249-57.
Checco, J. W.; Gellman, S. H., Iterative non-proteinogenic residue incorporation yields α/β-peptides with a helix-loop-helix tertiagy structure and high affinity for VEGF. *Chembiochem* 2017, 18 (3), 291.
Checco, J. W.; Kreitler, D. F.; Thomas, N. C.; Belair, D. G.; Rettko, N. J.; Murphy, W. L.; Forest, K. T.; Gellman, S. H., Targeting diverse protein-protein interaction interfaces with α/β-peptides derived from the Z-domain scaffold. *Proc. Natl. Acad. Sci.* 2015, 112 (15), 4552-4557.
Cheng, R. P.; Gellman, S. H.; DeGrado, W. F., beta-Peptides: from structure to function. *Chem. Rev.* 2001, 101 (10), 3219-32.
Cohen, M. H.; Gootenberg, J.; Keegan, P.; Pazdur, R., FDA drug approval summary. bevacizumab plus FOLFOX4 as second-line treatment of colorectal cancer. *Oncologist* 2007, 12 (3), 356-61.
Cook, K. M.; Figg, W. D., Angiogenesis Inhibitors: Current Strategies and Future Prospects. *CA Cancer J. Clin.* 2010, 60 (4), 222-243.
Cussol, L.; Mauran-Ambrosino, L.; Buratto, J.; Belorusova, A. Y.; Neuville, M.; Osz, J.; Fribourg, S.; Fremaux, J.; Dolain, C.; Goudreau, S. R.; Rochel, N.; Guichard, G., Structural Basis for α-Helix Mimicry and Inhibition of Protein—Protein Interactions with Oligourea Foldamers. *Angew. Chem. Int. Ed.* 2021, 60 (5), 2296-2303.
D'Andrea, L. D.; Iaccarino, G.; Fattorusso, R.; Sorriento, D.; Carannante, C.; Capasso, D.; Trimarco, B.; Pedone, C., Targeting angiogenesis: structural characterization and biological properties of a de novo engineered VEGF mimicking peptide. *Proc. Natl. Acad. Sci. U. S. A.* 2005, 102 (40), 14215-20.
Dellinger, M. T.; Brekken, R. A.., Phosphorylation of Akt and ERK1/2 Is Required for VEGF-A/VEGFR2-Induced Proliferation and Migration of Lymphatic Endothelium. *PLoS ONE* 2011, 6 (12), e28947, 1-9.
Dias, S.; Shmelkov, S. V.; Lam, G.; Rafii, S., VEGF(165) promotes survival of leukemic cells by Hsp90-mediated induction of Bcl-2 expression and apoptosis inhibition. *Blood* 2002, 99 (7), 2532-40.
Dvorak, H. F.; Brown, L. F.; Detmar, M.; Dvorak, A. M., Vascular permeability factor/vascular endothelial growth factor, microvascular hyperpermeability, and angiogenesis. *Am. J. Pathol.* 1995, 146 (5), 1029-39.

(Continued)

*Primary Examiner* — Amber D Steele
(74) *Attorney, Agent, or Firm* — Quarles & Brady LLP

(57) ABSTRACT

Provided herein are novel VEGF mimics, pharmaceutical compositions thereof, and methods of their use in increasing or reducing angiogenesis.

20 Claims, 27 Drawing Sheets
(20 of 27 Drawing Sheet(s) Filed in Color)
Specification includes a Sequence Listing.

(56) References Cited

PUBLICATIONS

Eskens, F. A. L. M., Angiogenesis inhibitors in clinical development; where are we now and where are we going? *Br. J. Cancer* 2004, 90, 1-7.
Felix, J.; Savvides, S. N., Mechanisms of immunomodulation by mammalian and viral decoy receptors: insights from structures. *Nat. Rev. Immunol.* 2017, 17 (2), 112-29.
Ferrara, N., Vascular endothelial growth factor: molecular and biological aspects. *Curr. Top. Microbiol. Immunol.* 1999, 237, 1-30.
Ferrara, N.; F.; Geber, H.P.; LeCouter, J., The biology of VEGF and its receptors. *Nat. Med.* 2003, 9 (6), 669-676.
Ferrara, N.; Davis-Smyth, T., the biology of vascular endothelial growth factor. *Endocr. Rev.* 1997, 18 (1), 4-25.
Fletcher, J. M.; Horner, K. A.; Bartlett, G. J.; Rhys, G. G.; Wilson, A. J.; Woolfson, D. N., De novo coiled-coil peptides as scaffolds for disrupting protein-protein interactions. *Chem. Sci.* 2018, 9 (39), 7656-165.
Folkman, J., Role of angiogenesis in tumor growth and metastasis. *Semin. Oncol.* 2002, 29 (6, Supplement 16), 15-18.
Folkman, J, Tumor angiogenesis: therapeutic implications. N. Engl. J. Med. 1971, 285 (21), 1182-6.
Folkman, J.; Hochberg, M., Self-regulation of growth in three dimensions. *J. Exp. Med.* 1973, 138 (4), 745-53.
Fosgerau, K.; Hoffmann, T., Peptide therapeutics: current status and future directions. *Drug Dis. Today* 2015, 20 (1), 122-128.
Gante, J., Azapeptides. *Synthesis* 1989, 21 (06), 405-413.
Gibadullin, R.; Randall, C. J.; Sidney, J.; Sette, A.; Gellman, S. H., Backbone Modifications of HLA-A2-Restricted Antigens Induce Diverse Binding and T Cell Activation Outcomes. *J. Am. Chem. Soc.* 2021, 143 (17), 6470-6481.
Gimbrone, M. A., Jr.; Cotran, R. S.; Leapman, S. B.; Folkman, J., Tumor growth and neovascularization: an experimental model using the rabbit cornea. *J. Natl. Cancer Inst.* 1974, 52 (2), 413-27.
Gimbrone, M. A., Jr.; Leapman, S. B.; Cotran, R. S.; Folkman, J., Tumor dormancy in vivo by prevention of neovascularization. *J. Exp. Med.* 1972, 136 (2), 261-76.
Gupta, K.; Zhang, J., Angiogenesis: a curse or cure? *Postgrad. Med. J.* 2005, 81 (954), 236-42.
Hanahan, D.; Weinberg, R. A., Hallmarks of cancer: the next generation. *Cell* 2011, 144 (5), 646-74.
Hiratsuka, S.; Minowa, O.; Kuno, J.; Noda, T.; Shibuya, M., Flt-1 lacking the tyrosine kinase domain is sufficient for normal development and angiogenesis in mice. *Proc. Natl. Acad. Sci. U. S. A.* 1998, 95 (16), 9349-54.
Ho, V. C.; Fong, G. H., Vasculogenesis and Angiogenesis in VEGF Receptor-1 Deficient Mice. *Methods Mol. Biol.* 2015, 1332, 161-76.
Ivanov, A. A.; Khuri, F. R.; Fu, H., Targeting protein-protein interactions as an anticancer strategy. *Trends Pharmacol. Sci.* 2013, 34 (7), 393-400.
Jedhe, G. S.; Arora, P. S., Chapter One—Hydrogen bond surrogate helices as minimal mimics of protein α-helices. In *Methods Enzymol.*, Petersson, E. J., Ed. Academic Press: 2021; vol. 656, pp. 1-25.
Karamysheva, A. F., Mechanisms of angiogenesis. *Biochemistry (Moscow)* 2008, 73 (7), 751.
Klagsbrun, M.; Moses, M. A., Molecular angiogenesis. *Chem. Biol.* 1999, 6 (8), R217-R224.
Langer, R.; Conn, H.; Vacanti, J.; Haudenschild, C.; Folkman, J., Control of tumor growth in animals by infusion of an angiogenesis inhibitor. *Proc. Natl. Acad. Sci. U. S. A.* 1980, 77 (7), 4331-5.
Lee, K. J.; Bang, G.; Kim, Y. W.; Shin, M. H.; Lim, H.-S., Design and synthesis of a DNA-encoded combinatorial library of bicyclic peptoids. *Biorg. Med. Chem.* 2021, 48, 116423.
Leung, D. W.; Cachianes, G.; Kuang, W. J.; Goeddel, D. V.; Ferrara, N., Vascular endothelial growth factor is a secreted angiogenic mitogen. *Science* 1989, 246 (4935), 1306-9.
Lohela, M.; Bry, M.; Tammela, T.; Alitalo, K., VEGFs and receptors involved in angiogenesis versus lymphangiogenesis. *Curr. Opin. Cell Biol.* 2009, 21 (2), 154-165.

Maity, D.; Hamilton, A. D., The helical supramolecular assembly of oligopyridylamide foldamers in aqueous media can be guided by adenosine diphosphates. *Chem. Commun.* 2021, 57 (73 ), 9192-95.
Muller, Y. A.; Christinger, H. W.; Keyt, B. A.; de Vos, A. M., The crystal structure of vascular endothelial growth factor (VEGF) refined to 1.93 Å resolution: multiple copy flexibility and receptor binding. *Structure* 1997, 5 (10), 1325-1338.
Muller, Y. A, Li, B., Christinger, H. W.; Wells, J. A.; Cunningham, B. C.; De Vos, A. M., Vascular Endothelial Growth Factor: Crystal Structure and Functional Mapping of the Kinase Domain Receptor Binding Site. *Proc. Natl. Acad. Sci. U. S. A.* 1997, 94 (14), 7192-7197.
Neufeld, G.; Tessler, S.; Gitay-Goren, H.; Cohen, T.; Levi, B. Z., Vascular endothelial growth factor and its receptors. *Prog. Growth Factor Res.* 1994, 5 (1), 89-97.
Outlaw, V. K.; Cheloha, R. W.; Jurgens, E. M.; Bovier, F. T.; Zhu, Y.; Kreitler, D. F.; Harder, O., Niewiesk, S.; Porotto, M.; Gellman, S. H.; Moscona, A., Engineering Protease-Resistant Peptides to Inhibit Human Parainfluenza Viral Respiratory Infection. *J. Am. Chem. Soc.* 2021, 143 (15), 5958-5966.
Pelay-Gimeno, M.; Glas, A.; Koch, O.; Grossmann, T. N., Structure-Based Design of Inhibitors of Protein-Protein Interactions: Mimicking Peptide Binding Epitopes. *Angew. Chem. Int. Ed. Engl.* 2015, 54 (31), 8896-927.
Rahimi, N.; Dayanir, V.; Lashkari, K., Receptor Chimeras Indicate That the Vascular Endothelial Growth Factor Receptor-1 (VEGFR-1) Modulates Mitogenic Activity of VEGFR-2 in Endothelial Cells*. *J. Biol. Chem.* 2000, 275 (22), 16986-16992.
Ronca, R.; Benkheil, M.; Mitola, S.; Struyf, S.; Liekens, S., Tumor angiogenesis revisited: Regulators and clinical implications. *Med. Res. Rev.* 2017, 37 (6), 1231-1274.
Ryan, D. P.; Matthews, J. M., Protein-protein interactions in human disease. *Curr. Opin. Struc. Biol.* 2005, 15 (4), 441-446.
Rzeigui, M.; Traikia, M.; Jouffret, L.; Kriznik, A.; Khiari, J.; Roy, O.; Taillefumier, C., Strengthening Peptoid Helicity through Sequence Site-Specific Positioning of Amide cis-Inducing NtBu Monomers. *J. Org. Chem.* 2020, 85 (4), 2190-2201.
Sabatino, D.; Proulx, C.; Pohankova, P.; Ong, H.; Lubell, W. D., Structure-Activity Relationships of GHRP-6 Azapeptide Ligands of the CD36 Scavenger Receptor by Solid-Phase Submonomer Azapeptide Synthesis. *J. Am. Chem. Soc.* 2011, 133 (32), 12493-12506.
Sang, P.; Shi, Y.; Huang, H.; Xue, S.; Odom, T.; Cai, J., Sulfono-γ-AApeptides as Helical Mimetics: Crystal Structures and Applications. *Acc. Chem. Res.* 2020, 53 (10), 2425-2442.
Sang, P.; Shi, Y.; Lu, J.; Chen, L.; Yang, L.; Borcherds, W.; Abdulkadir, S.; Li, Q.; Daughdrill, G.; Chen, J.; Cai, J., α-Helix-Mimicking Sulfono-γ-AApeptide Inhibitors for p53-MDM2/MDMX Protein-Protein Interactions. *J. Med. Chem.* 2020, 63, 975-986.
Sang, P.; Zhang, M.; Shi, Y.; Li, C.; Abdulkadir, S.; Li, Q.; Ji, H.; Cai, J., Inhibition of β-catenin/B Cell Lymphoma 9 Protein-protein Interaction using α-helix-mimicking Sulfono-γ-AApeptide Inhibitors. *Proc. Natl. Acad. Sci. U. S. A.* 2019, 116, 10757-62.
Sang, P.; Zhou, Z.; Shi, Y.; Lee, C.; Amso, Z.; Huang, D.; Odom, T.; Nguyen-Tran, V.; Shen, W.; Cai, J., The Activity of Sulfono-γ-AApeptide Helical Foldamers That Mimic GLP-1. *Sci. Adv.* 2020, 6, eaaz4988, 1-7.
Schaefer, M. H.; Lopes, T. J.; Mah, N.; Shoemaker, J. E.; Matsuoka, Y.; Fontaine, J. F.; Louis-Jeune, C.; Eisfeld, A. J.; Neumann, G.; Perez-Iratxeta, C.; Kawaoka, Y.; Kitano, H.; Andrade-Navarro, M. A., Adding protein context to the human protein-protein interaction network to reveal meaningful interactions. *PLoS Comput. Biol.* 2013, 9 (1), e1002860, 376-385.
She, F.; Teng, P.; Peguero-Tejada, A.; Wang, M.; Ma, N.; Odom, T.; Zhou, M.; Gjonaj, E.; Wojtas, L.; van der Vaart, A.; Cai, J., De Novo Left-Handed Synthetic Peptidomimetic Foldamers. *Angew. Chem. Int. Ed.* 2018, 57 (31), 9916-9920.
Shi, Y.; Sang, P.; Lu, J.; Higbee, P.; Chen, L.; Yang, L.; Odom, T.; Daughdrill, G.; Chen, J.; Cai, J., Rational Design of Right-Handed Heterogeneous Peptidomimetics as Inhibitors of Protein-Protein Interactions. *J. Med. Chem.* 2020, 63 (21), 13187-13196.

(56) References Cited

PUBLICATIONS

Shi, Y.; Teng, P.; Sang, P.; She, F.; Wei, L.; Cai, J., γ-AApeptides: Design, Structure, and Applications. *Acc. Chem. Res.* 2016, 49 (3), 428-441.

Shibuya, M., Vascular endothelial growth factor receptor-1 (VEGFR-1/Flt-1): a dual regulator for angiogenesis. Angiogenesis 2006, 9 (4), 225-30; discussion 231.

Shubik, P., Vascularization of tumors: a review. J. Cancer Res. Clin. Oncol. 1982, 103 (3), 211-26.

Teng, P.; Ma, N.; Cerrato, D. C.; She, F.; Odom, T.; Wang, X.; Ming, L. J.; van der Vaart, A.; Wojtas. L.; Xu, H.; Cai, J., Right-Handed Helical Foldamers Consisting of De Novo d-AApeptides. J. Am. Chem. Soc. 2017, 139, 7363, 1-18.

Teng, P.; Gray, G. M.; Zheng, M.; Singh, S.; Li, X.; Wojtas, L.; van der Vaart, A.; Cai, J., Orthogonal Halogen-Bonding-Driven 3D Supramolecular Assembly of Right-Handed Synthetic Helical Peptides. Angew. Chem., Int. Ed. 2019, 58, 7778, 1-12.

Wu, H.; Qiao, Q.; Hu, Y.; Teng, P.; Gao, W.; Zuo, X.; Wojtas, L.; Larsen, R. W.; Ma, S.; Cai, J., Sulfono-γ-AApeptides as a New Class of Nonnatural Helical Foldamer. *Chem. Eur. J.* 2015, 21 (6), 2501-2507.

Yoo, S. H.; Li, B.; Dolain, C.; Pasco, M.; Guichard, G., Chapter Three—Urea based foldamers. In *Methods Enzymol.*, Petersson, E. J., Ed. Academic Press: 2021; vol. 656, pp. 59-92.

Zetter, P. B., Angiogenesis and Tumor Metastasis. *Annu. Rev. Med.* 1998, 49 (1), 407-424.

\* cited by examiner

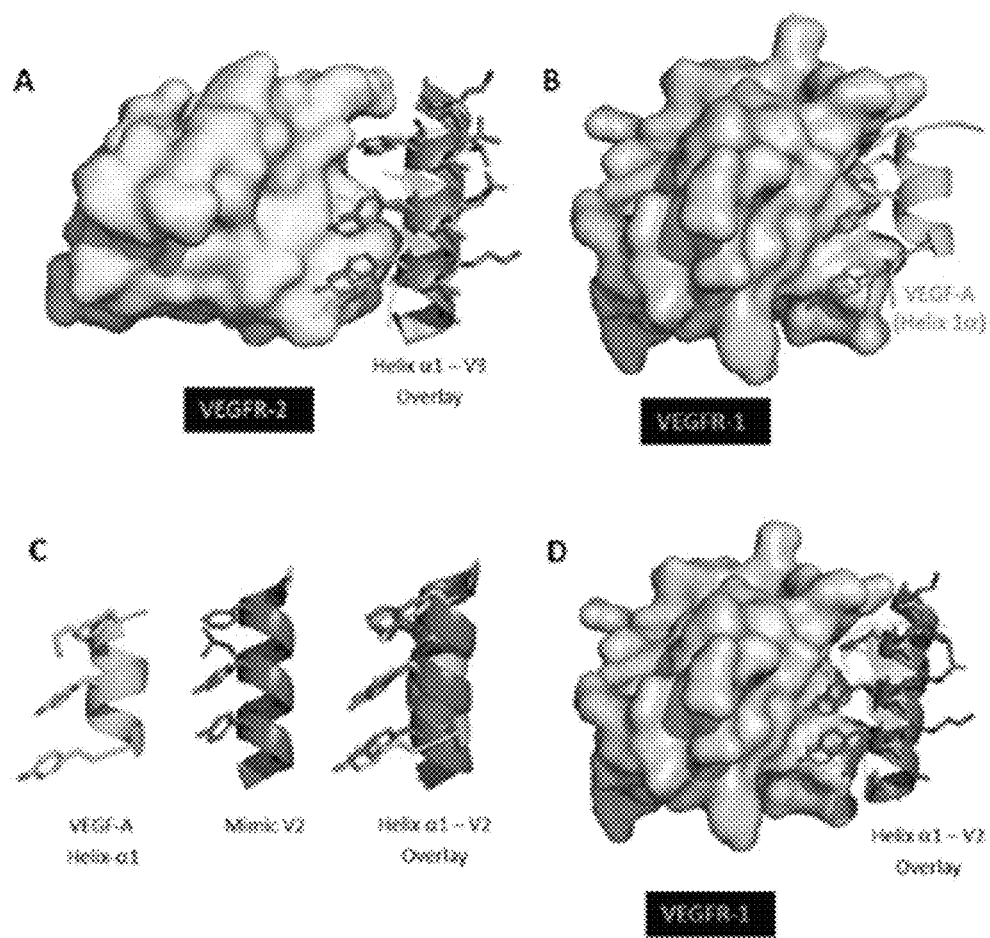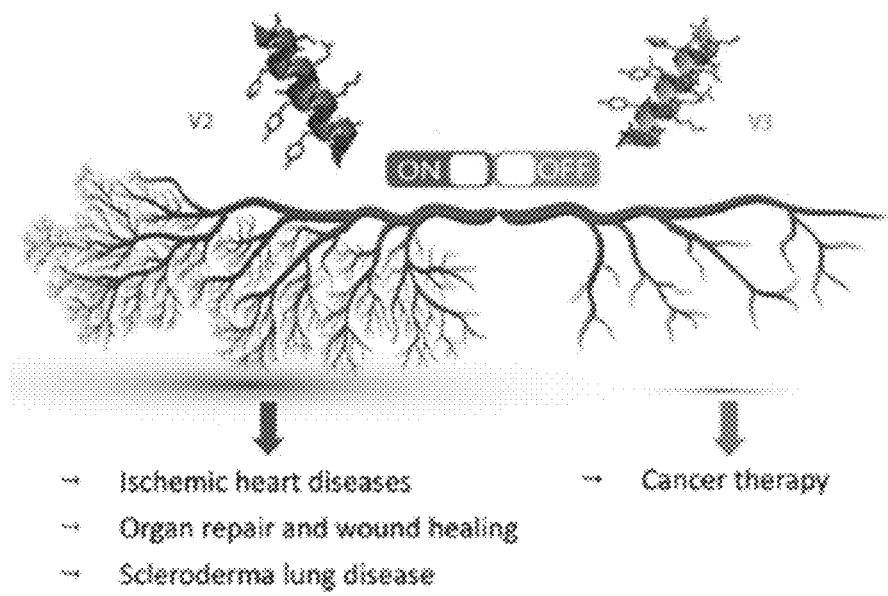
FIGS. 10A-10E

| | Structure | Kd (μM) | |
|---|---|---|---|
| | | VEGFR-1 | VEGFR-2 |
| V1 | 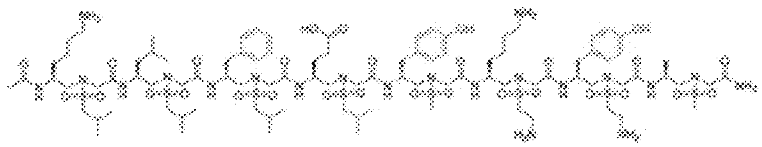 | 12.9 | 5.1 |
| V2 | 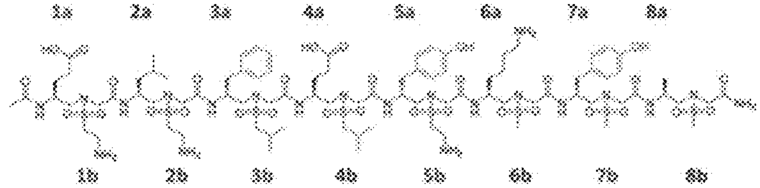 | 0.46 | 2.3 |
| V3 | 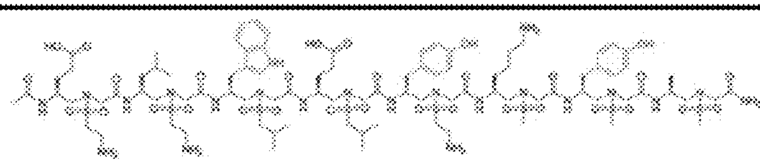 | 7.7 | 0.63 |
| V4 | 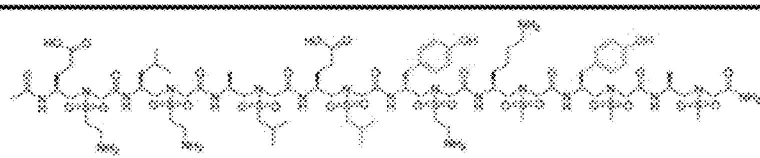 | >100 | >100 |
| V5 | 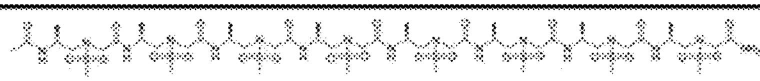 | >100 | >100 |
| QK | Ac-KLTWQELYQLKYKGI (SEQ ID NO: 1) | | |
| MA | Ac-KLTWMELYQLAYKGI (SEQ ID NO: 2) | | |

FIG. 12

MODULATING ANGIOGENESIS BY PROTEOMIMETICS OF VASCULAR ENDOTHELIAL GROWTH FACTOR

CROSS-REFERENCE TO RELATED APPLICATIONS

This application claims priority to, and the benefit of, U.S. Application No. 63/265,835 filed Dec. 21, 2021, the content of which is incorporated herein by reference in its entirety.

STATEMENT REGARDING FEDERALLY SPONSORED RESEARCH

This invention was made with government support under R01AG056569 and R01AI152416 awarded by the National Institutes of Health. The government has certain rights in this invention.

REFERENCE TO AN ELECTRONIC SEQUENCE LISTING

The contents of the electronic sequence listing (173738.02616.xml; Size: 2,683 bytes; and Date of Creation: Dec. 19, 2022) is herein incorporated by reference in its entirety.

BACKGROUND

Angiogenesis, formation of new blood vessels from the existing vascular network, is a vital process in early developmental processes and healing. Notably, this process is mostly inactive in healthy adults and is tightly regulated by a combination of pro-angiogenic and anti-angiogenic proteins. However, during tumor progression the angiogenesis signaling is activated and leads to tumor vascular proliferation and consequent tumor metastasis.[1-5] It is for this reason that the prospect of affecting this process has gained considerable interest in the fight against cancer. On the other hand, silenced angiogenesis could hamper tissue regeneration, resulting in other diseases such as stroke and cardiovascular disease. As such, the strategy that could manipulate the angiogenic response would be promising for applications in both molecular biology and therapeutics.

It is well recognized that sustained angiogenesis constitutes one of the hallmarks of cancer cells and is modulated through vascular endothelial growth factor (VEGF),[6,7] a potent proangiogenic factor. VEGF is a homodimeric glycoprotein that binds to three VEGF-specific receptor tyrosine kinases, VEGFR-1, VEGFR-2, and VEGFR-3, and is overexpressed in a number of cancer cells.[8-10] VEGF-A$_{165}$ represents the most predominant VEGF isoform in humans and is a potent activator of VEGFR-1 and VEGFR-2 expressed on vascular endothelial cells. The binding of VEGF with VEGFR-2 leads to VEGFR-2 dimerization and phosphorylation of intracellular kinases, which induce cell survival, migration, and proliferation.[11-15] VEGFR-1 has a 10-fold higher binding affinity to VEGF-A as compared with VEGFR-2; however its proangiogenic effect is low to none.[16,17] The exact role of VEGFR-1 in angiogenesis is debatable, but its higher affinity to VEGF-A and low proangiogenic effects and the existence of a soluble form of VEGFR-1 lacking a transmembrane tyrosine kinase domain suggest that it may serve as a decoy receptor and negatively control angiogenesis.[18,19] This is also supported by gene deletion studies where VEGFR-1 (−/−) mice died due to excessive endothelial cell differentiation, whereas VEGFR-2 (−/−) mice died due to lack of vascular formation.[20,21]

The therapeutic relevance of inhibiting angiogenesis in cancer has been established through the extensive works done by Folkman and colleagues in the 1970s,[22-26] and concerted efforts in the following decades have produced clinically viable angiogenesis inhibitors targeting VEGF-A and VEGFRs, with Bevacizumab being the first angiogenesis inhibitor approved by the FDA in 2004, which was followed by other monoclonal antibodies and small-molecule tyrosine kinase inhibitors.[27-29] However, the success of antiangiogenic agents has been mixed across different types of cancers and has not met the high expectation of universal anticancer efficacy, underlining the need for a better understanding and more effective approach to modulate angiogenesis.[30]

SUMMARY OF THE DISCLOSURE

Provided herein are compositions and methods relating to sulfono-γ-AA peptides that mimic VEGF.

In an embodiment, a sulfono-γ-AA peptides according to Formula 1 and having the structure:

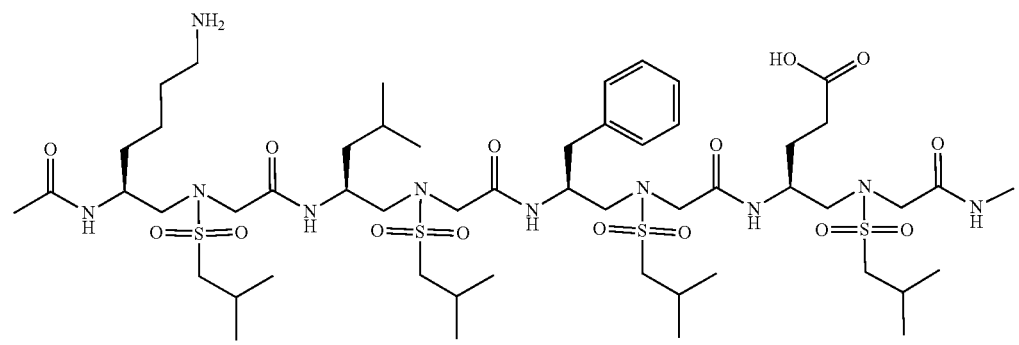

-continued

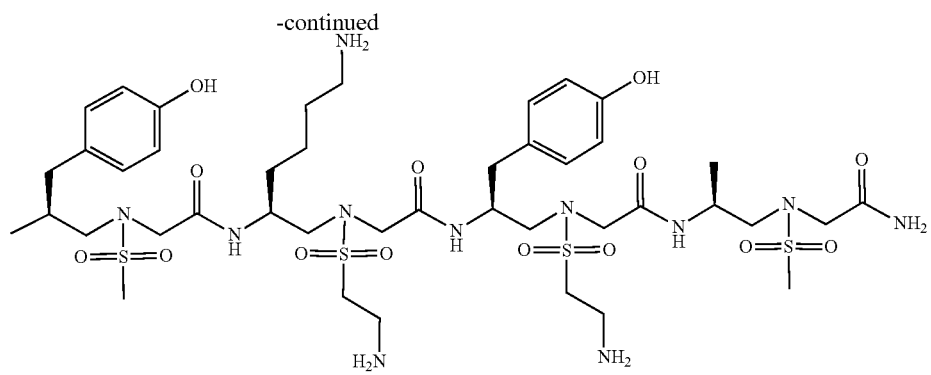

is provided.

In an embodiment, a sulfono-γ-AA peptide according to Formula 3 and having the structure:

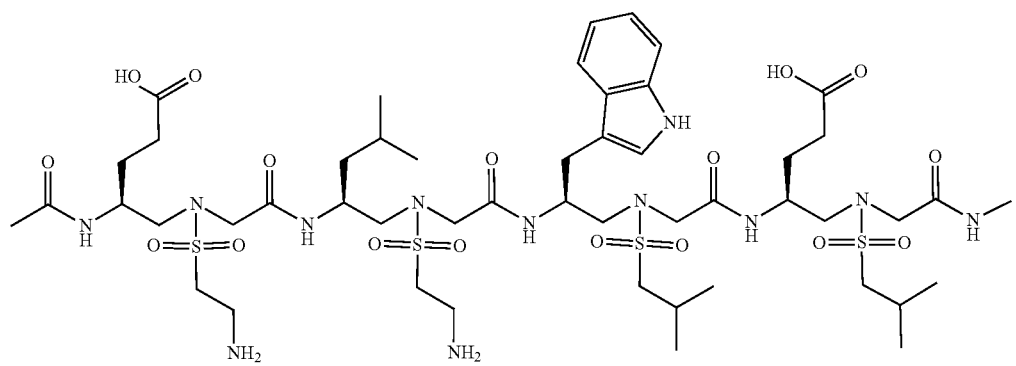

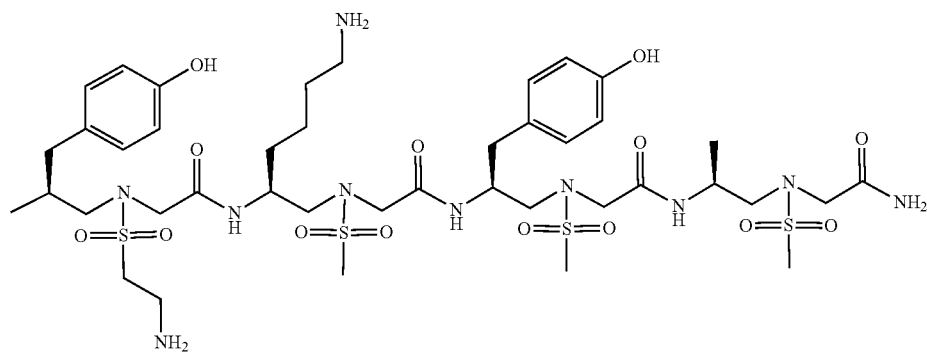

is provided.

In an embodiment, a method of reducing cell migration in a population of cells, the method comprising administering to the cells the sulfono-γ-AA peptide of Formula 1 or Formula 3 is provided.

In an embodiment, a method of reducing capillary tube formation in a population of cells, the method comprising administering to the cells the sulfono-γ-AA peptide of Formula 1 or Formula 3 is provided.

In an embodiment, a pharmaceutical composition comprising the sulfono-γ-AA peptide of Formula 1 or Formula 3; and a pharmaceutically acceptable carrier is provided.

In an embodiment, a method of reducing angiogenesis in a subject in need thereof comprising administering to the subject a therapeutically acceptable amount of the composition of Formula 1 or Formula 3 is provided. In some embodiments, the subject in need thereof has, or is suspected of having, a cancer or retinopathy.

In an embodiment, a sulfono-γ-AA peptide according to Formula 2 and having the structure:

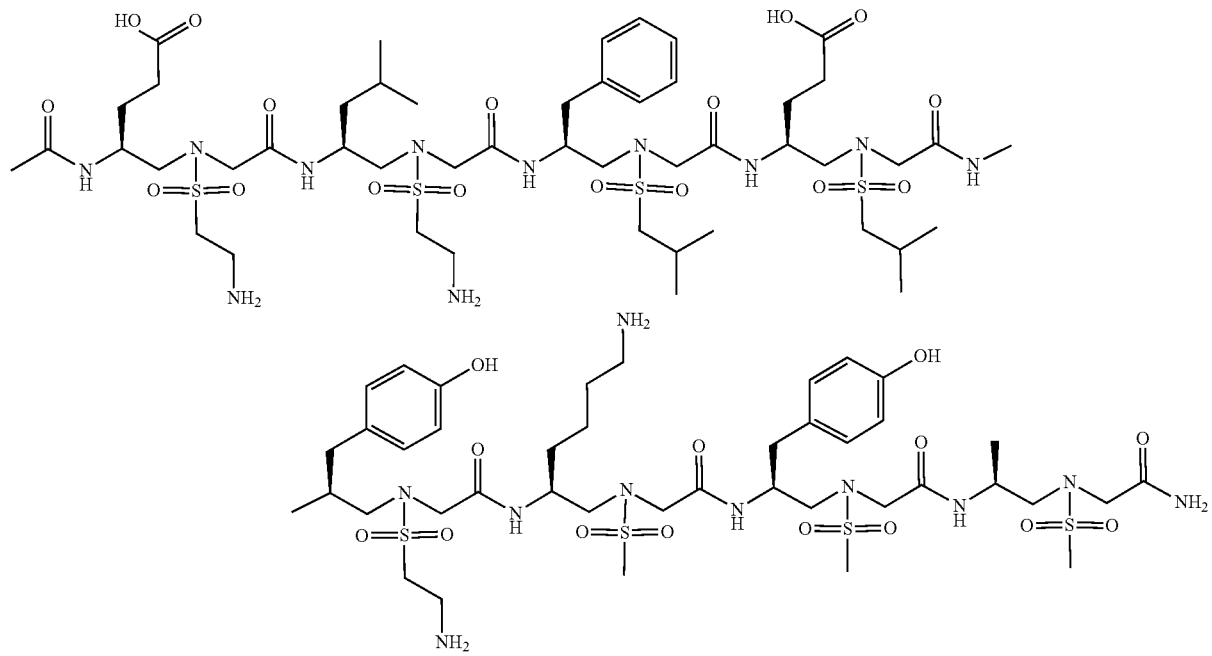

is provided.

In an embodiment, a method of increasing cell migration in a population of cells, the method comprising administering to the cells the sulfono-γ-AA peptide of Formula 2 is provided.

In an embodiment, a method of increasing capillary tube formation in a population of cells, the method comprising administering to the cells the sulfono-γ-AA peptide of Formula 2 is provided.

In an embodiment, a pharmaceutical composition comprising the sulfono-γ-AA peptide of Formula 2; and a pharmaceutically acceptable carrier.

In an embodiment, a method of increasing angiogenesis in a subject in need thereof comprising administering to the subject a therapeutically acceptable amount of the composition of Formula 2 is provided. In some embodiments, the subject in need thereof has, or is suspected of having, ischemic heart disease. In some embodiments, the subject in need thereof has a wound or damage to an organ.

In an embodiment, a pharmaceutical composition comprising at least one of the sulfono-γ-AA peptide of Formula 1, Formula 2, and Formula 3; and a pharmaceutically acceptable carrier is provided herein.

BRIEF DESCRIPTION OF DRAWINGS

This patent or application file contains at least one drawing executed in color. Copies of this patent or patent application publication with color drawing(s) will be provided by the Office upon request and payment of the necessary fee.

FIG. 2A shows the structure of sulfono-γ-AA peptide building block. "a" and "b" denote chiral side chain and sulfono side chain, respectively. FIG. 2B is a schematic representation of side chain distribution in a left-handed sulfono-γ-AA peptide helix scaffold. FIGS. 2C and 2D are crystal structures of sulfono-γ-AA peptide side view and top view, respectively.

FIG. 3A shows binding interaction of key residues on helix-α1 of VEGF-A (green) with VEGFR-2 (yellow), PDB code: 3V2A. FIG. 3B shows structures of helix-α1 of VEGF-A (green), sulfono-γ-AA peptide mimic V3 (magenta), and overlay of key binding residues.

FIG. 5A. Increased migration of HUVECs treated with V2 and QK. Marked inhibition of migration is observed in cells treated with V1 and V3. FIG. 5B Percentage of HUVECs migrating, compared to control, following treatments with VEGF mimics in the presence $VEGF_{165}$. Concentration of treatments: $VEGF_{165}$ (50 ng/mL), all other peptidic sequences (10 μM), control (no treatment). Results presented as mean±SD (n=3), *P<0.05, P<0.01, *P<0.001.

FIG. 6A. Migration of HUVECs following treatments with VEGF mimics in the presence of $VEGF_{165}$ observed at 0 and 24 h. FIG. 6B. Percentage of wound area remaining high (inhibition of migration) after 24 h in HUVECs treated with V1 and V3. However, V2 and QK, as compared to cells treated with $VEGF_{165}$ only, did not activate migration. Concentration of treatments: $VEGF_{165}$ (50 ng/mL), VEGF mimic sequences (10 μM), control (no treatment). Results presented as mean±SD (n=3), ***P<0.001.

FIG. 7A. Increased capillary tube formation in cells treated with QK and V2. FIG. 7B. Graphical representation of percentage count, compared to control, of capillary tube nodes of HUVECs for FIG. 7A. FIG. 7C. Decreased capillary tube formation in cells treated with V1 and V3. FIG. 7D. Graphical representation for FIG. 7C. $VEGF_{165}$ (50 ng/mL), VEGF mimic sequences (2 μM), negative control (no treatment). Results presented as mean±SD (n=3), *P<0.05, P<0.01, *P<0.001.

(FIG. 9C and FIG. 9D) Bar graph of relative fluorescence intensity of V2 and V3 compared to control in cells treated with anti-VEGFR-1 and anti-VEGFR-2 antibodies. Results presented as mean±SD (n=3), P<0.01, *P<0.001.

FIGS. 10A-10E. FIG. 10A. Superimposition of V3 (teal) with critical residues of helix-α1 (green) on the binding surface of VEGFR-2 (yellow). FIG. 10B. Binding interaction of key residues on helix-α1 of VEGF-A (green) with VEGFR-1 (bronze), PDB: 1 flt. FIG. 10C. Structures of helix-α1 of VEGF-A (green), sulfono-γ-AA peptide mimic V2 (magenta), and overlay of key binding residues. FIG. 10D. Superimposition of V2 (magenta) with critical residues of helix-α1 (green) on the binding surface of VEGFR-1 (bronze). FIG. 10E. Modulation of the angiogenic switch with sulfono-γ-AA peptide mimics of VEGF-A.

FIG. 12. Structures of Selected Sulfono-γ-AA Peptide Helical Mimics (V1-V5). Critical residues for binding are shown in red and pink. Binding affinity ($K_d$) of sequences to VEGFR-1 and VEGFR-2 as determined by SPR. The chemical structures of two reported peptides QK and MA are also included.

DETAILED DESCRIPTION OF THE INVENTION

Figure 1:
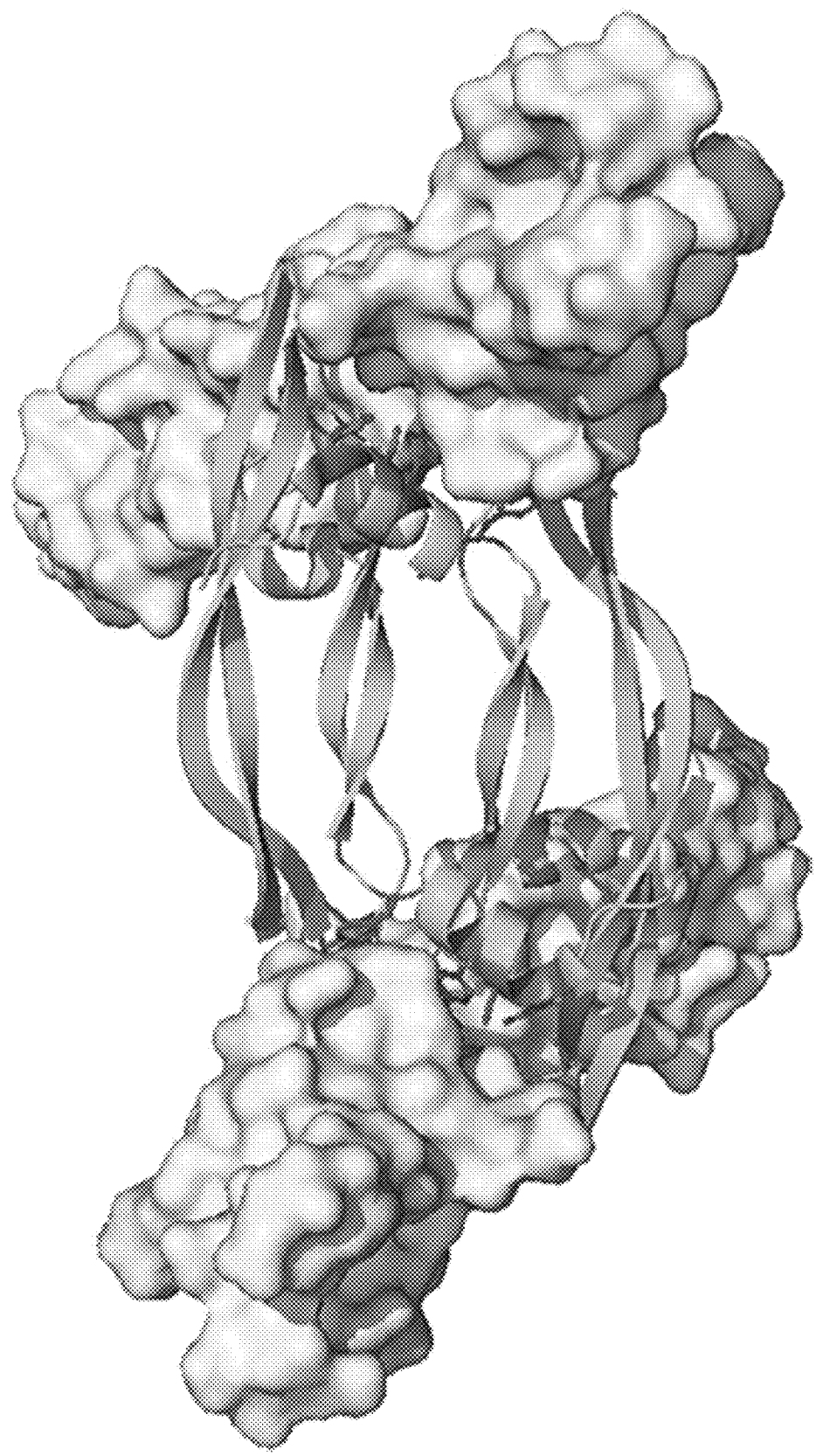
FIG. 1. Structure of VEGF-A/VEGFR-2 complex, Protein Data Bank (PDB): 3V2A. Homodimeric VEGF-A (green) binding to, and dimerization of, VEGFR-2 (yellow). Key binding residues on VEGF-A helix-α1 (Phe17, Met18, Tyr21, and Tyr25) are highlighted in red.
Figures 2A, 2B, 2C, 2D:
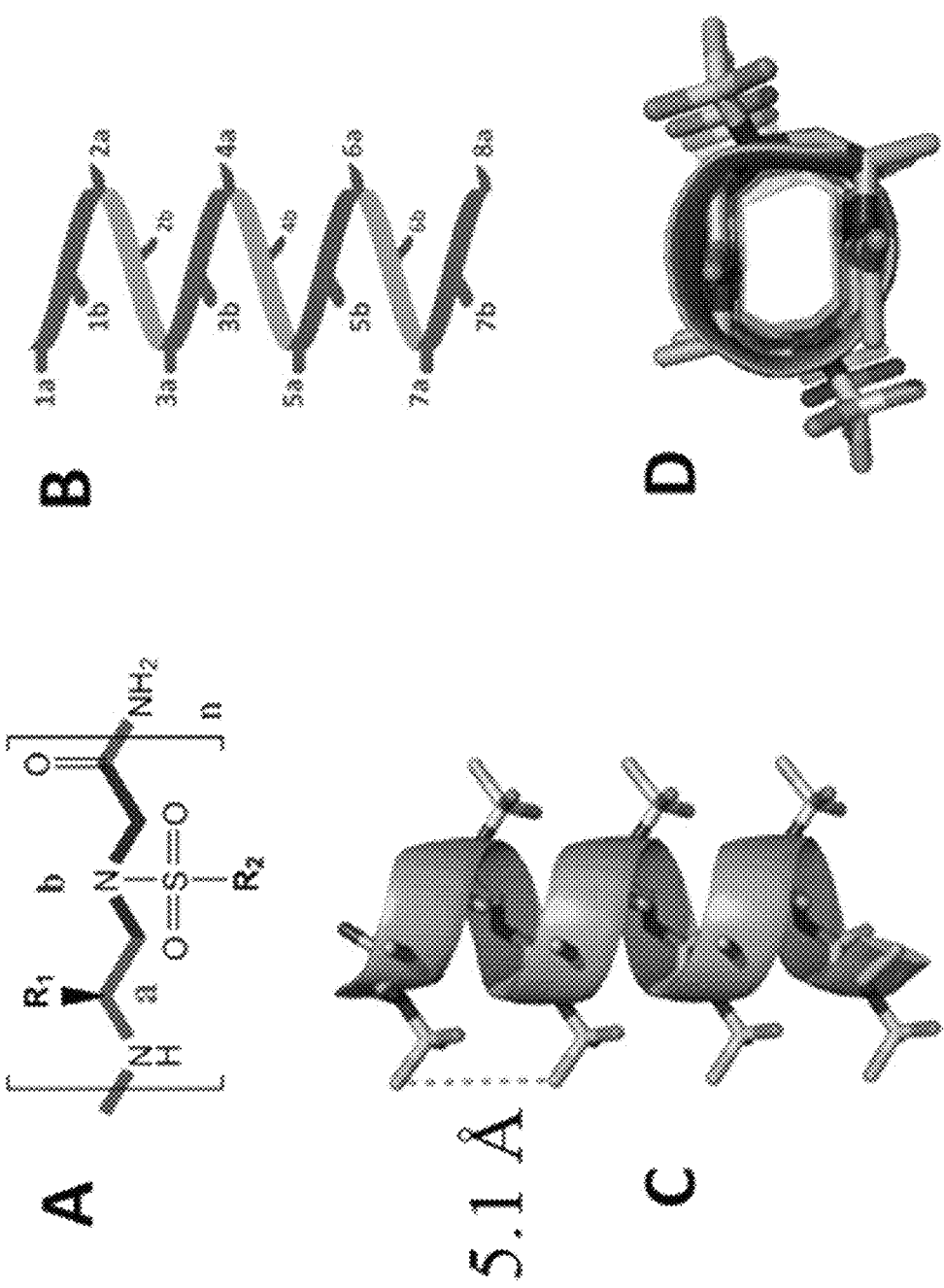
FIGS. 2A-2D.
Figures 3A, 3B:
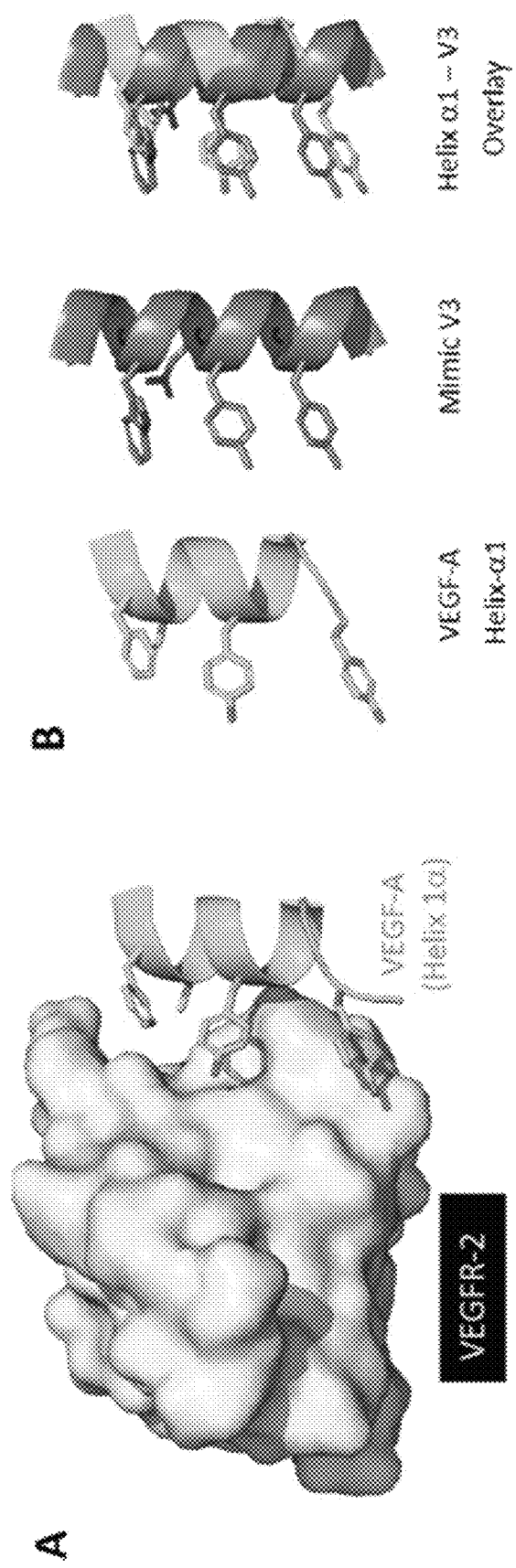
FIGS. 3A-3B.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are cited to disclose and describe the methods and/or materials in connection with which the publications are cited. All such publications and patents are herein incorporated by references as if each individual publication or patent were specifically and individually indicated to be incorporated by reference. Such incorporation by reference is expressly limited to the methods and/or materials described in the cited publications and patents and does not extend to any lexicographical definitions from the cited publications and patents. Any lexicographical definition in the publications and patents cited that is not also expressly repeated in the instant application should not be treated as such and should not be read as defining any terms appearing in the accompanying claims. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed. As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of molecular biology, microbiology, nanotechnology, chemistry, organic chemistry, biochemistry, pharmacology, and the like, which are within the skill of the art. Such techniques are explained fully in the literature.

Definitions

As used herein, "about," "approximately," and the like, when used in connection with a numerical variable, generally refers to the value of the variable and to all values of the variable that are within the experimental error (e.g., within the 95% confidence interval for the mean) or within +/−10% of the indicated value, whichever is greater.

As used herein, "additive effect" can refer to an effect arising between two or more molecules, compounds, substances, factors, or compositions that is equal to or the same as the sum of their individual effects.

As used herein, "administering" can refer to any administration route, including but not limited to administration that is oral, topical, intravenous, subcutaneous, transcutaneous, transdermal, intramuscular, intra-articular, parenteral, intra-arterial, intradermal, intraventricular, intracranial, intraperitoneal, intralesional, intranasal, rectal, vaginal, by inhalation, or via an implanted reservoir. The term "parenteral" includes subcutaneous, intravenous, intramuscular, intra-articular, intra-synovial, intrasternal, inter nasal, intrathecal, intrahepatic, intralesional, and intracranial injections or infusion techniques.

As used interchangeably herein, "biocompatible," "biocompatibility," and "biologically compatible" refer to materials that are, with any metabolites or degradation products thereof, generally non-toxic to the recipient, and cause no significant adverse effects to the recipient. Generally speaking, biocompatible materials are materials which do not elicit a significant inflammatory or immune response when administered to a patient. In some embodiments, a biocompatible material elicits no detectable change in one or more biomarkers indicative of an immune response. In some embodiments, a biocompatible material elicits no greater than a 10% change, no greater than a 20% change, or no greater than a 40% change in one or more biomarkers indicative of an immune response.

As used herein, "cancer" can refer to any disease within the collection of related diseases whose etiology and/or pathology involve abnormal cell growth and proliferation that can include invasion into surrounding and/or distant tissues. Cancerous tumors can be malignant or benign.

As used herein, "chemotherapeutic" refers to a chemical compound or agent used to treat, control, or cure a disease or symptoms thereof, particularly cancer.

As used herein, "composition" or "formulation" can refer to a combination of an active agent(s) and another compound or composition, inert (for example, a detectable agent or label) or active, such as an adjuvant.

As used herein, "a compound or peptide of formula (1), (2), (3), (4), (5), (6), (7), (8), (9), (10), (11), (12), (13), (14), and so forth and so on," or "a compound or peptide having a structure according to formula (1), (2), (3), (4), (5), (6), (7), (8), (9), (10), (11), (12), (13), (14), and so forth and so on" can include all or any sub-group of solvates, complexes, polymorphs, derivatives thereof (including but not limited to, radiolabeled derivatives (including deuterated derivatives where one or more H are replaced by D)), tautomers, stereoisomers, and optical isomers of the compound of the formulas listed above and salts thereof.

As used herein, "control" can refer to an alternative subject or sample used in an experiment for comparison purposes and included to minimize or distinguish the effect of variables other than an independent variable. A control can be positive or negative.

As used herein, "concentrated" used in reference to an amount of a molecule, compound, or composition, including, but not limited to, a chemical compound, polynucleotide, peptide, polypeptide, protein, antibody, or fragments thereof, that indicates that the sample is distinguishable from its naturally occurring counterpart in that the concentration or number of molecules per volume is greater than that of its naturally occurring counterpart.

As used herein, "derivative" can refer to any compound having the same or a similar core structure to the compound but having at least one structural difference, including substituting, deleting, and/or adding one or more atoms or functional groups. The term "derivative" does not mean that the derivative is synthesized from the parent compound either as a starting material or intermediate, although this may be the case. The term "derivative" can include salts, prodrugs, or metabolites of the parent compound. Derivatives include compounds in which free amino groups in the parent compound have been derivatized to form amine hydrochlorides, p-toluene sulfonamides, benzoxycarboamides, t-butyloxycarboamides, thiourethane-type derivatives, trifluoroacetylamides, chloroacetylamides, or formamides. Derivatives include compounds in which carboxyl groups in the parent compound have been derivatized to form salts, methyl and ethyl esters, or other types of esters or hydrazides. Derivatives include compounds in which hydroxyl groups in the parent compound have been derivatized to form O-acyl or O-alkyl derivatives. Derivatives include compounds in which a hydrogen bond donating group in the parent compound is replaced with another hydrogen bond donating group such as OH, NH, or SH. Derivatives include replacing a hydrogen bond acceptor group in the parent compound with another hydrogen bond acceptor group such as esters, ethers, ketones, carbonates, tertiary amines, imines, thiones, sulfones, tertiary amides, and sulfides. "Derivatives" also includes extensions of the replacement of the cyclopentane ring with saturated or unsaturated cyclohexane or other more complex, e.g., nitrogen-containing rings, and extensions of these rings with various side groups.

As used herein, "diluted" when used in reference to an amount of a molecule, compound, or composition including but not limited to, a chemical compound, polynucleotide, peptide, polypeptide, protein, antibody, or fragments thereof, can indicate that the sample is distinguishable from its naturally occurring counterpart in that the concentration or number of molecules per volume is less than that of its naturally occurring counterpart.

As used herein, "effective amount" or "pharmaceutically effective amount" is an amount sufficient to effect beneficial or desired results. An effective amount can be administered in one or more administrations, applications, or dosages. "Effective amount" can refer to an amount of a sulfono-γ-AA peptide provided herein (e.g. a compound or peptide according to Formula 1, Formula 2, or Formula 3 or a structural analogue thereof) that can reduce or increase angiogenesis, which can be measured using a suitable assay (including cell migration assay, wound healing assay, capillary tube formation assay, etc.) Structural analogues of a sulfono-γ-AA peptide provided herein are those structural analogues that carry the same backbone but can be substituted in one or more position. "Effective amount" can refer to an amount of a sulfono-γ-AA peptide provided herein that can reduce angiogenesis to treat a condition, such as a cancer or retinopathy, in a subject in need thereof. "Effective amount" can also refer to an amount of a sulfono-γ-AA peptide provided herein that can increase angiogenesis to treat a condition such as ischemic heart disease, or to repair a wound or organ damage in a subject in need thereof. "Effective amount" can refer to an amount of a sulfono-γ-AA peptide provided herein that can treat or prevent a condition, such as a cancer, retinopathy, ischemic heart disease, or a chronic wound. "Effective amount" can refer to an amount of a sulfono-γ-AA peptide provided herein that can treat or prevent or delay onset or symptoms of a cancer, retinopathy, ischemic heart disease, or a chronic wound in a subject having or suspected of having such. The "effective amount" can also refer to the least amount sufficient to effect beneficial or desired results, which are discussed above.

In some aspects, the subject can have a disease or disorder in which the disease or disorder is impacted positively or negatively by angiogenesis compared to a non-diseased control.

As used herein, "pharmaceutical formulation" or "pharmaceutical composition" can refer to the combination of an active agent, compound, or ingredient with a pharmaceutically acceptable carrier or excipient, making the composition suitable for diagnostic, therapeutic, or preventive use in vitro, in vivo, or ex vivo.

As used herein, "pharmaceutically acceptable" can refer to compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio, in accordance with the guidelines of agencies such as the Food and Drug Administration.

As used herein, "pharmaceutically acceptable carrier or excipient" refers to a carrier or excipient that is useful in preparing a pharmaceutical composition that is generally safe, non-toxic and neither biologically nor otherwise undesirable, and includes a carrier or excipient that is acceptable for veterinary use as well as human pharmaceutical use. A "pharmaceutically acceptable carrier or excipient" as used herein also includes both one and more than one such carrier or excipient. Pharmaceutically acceptable carriers include, but are not limited to, diluents, preservatives, binders, lubricants, disintegrators, swelling agents, fillers, stabilizers, and combinations thereof.

As used herein, "pharmaceutically acceptable salt" can refer to any salt derived from organic and inorganic acids of a compound described herein. Pharmaceutically acceptable salt also refers to a salt of a compound described having an acidic functional group, such as a carboxylic acid functional group, and a base. Pharmaceutically acceptable salt also includes hydrates of a salt of a compound described herein.

As used herein, "preventative," "preventing," "prevent" and the like refer to partially or completely delaying or precluding the onset or recurrence of a disorder or conditions and/or one or more of its attendant symptoms or barring a subject from acquiring or reacquiring a disorder or condition or reducing a subject's risk of acquiring or reacquiring a disorder or condition or one or more of its attendant symptoms.

As used interchangeably herein, "subject," "individual," or "patient," can refer to a vertebrate, preferably a mammal, more preferably a human. Mammals include, but are not limited to, murines, simians, humans, farm animals, sport animals, and pets. The term "pet" includes a dog, cat, guinea pig, mouse, rat, rabbit, ferret, and the like. The term farm animal includes a horse, sheep, goat, chicken, pig, cow, donkey, llama, alpaca, turkey, and the like.

As used herein, "separated" can refer to the state of being physically divided from the original source or population such that the separated compound, agent, particle, chemical compound, or molecule can no longer be considered part of the original source or population.

As used herein, "solvate" refers to a complex of variable stoichiometry formed by a solute (e.g. Formula 1, Formula 2, or Formula 3, or a salt thereof) and a solvent. Pharmaceutically acceptable solvates may be formed for crystalline compounds wherein solvent molecules are incorporated into the crystalline lattice during crystallization. The incorporated solvent molecules can be water molecules or non-aqueous molecules, such as but not limited to, ethanol, isopropanol, dimethyl sulfoxide, acetic acid, ethanolamine, and ethyl acetate molecules.

As used herein, the term "specific binding" can refer to non-covalent physical association of a first and a second moiety wherein the association between the first and second moieties is at least 2 times as strong, at least 5 times as strong as, at least 10 times as strong as, at least 50 times as strong as, at least 100 times as strong as, or stronger than the association of either moiety with most or all other moieties present in the environment in which binding occurs. Binding of two or more entities may be considered specific if the equilibrium dissociation constant, Kd, is $10^{-3}$ M or less, $10^{-4}$ M or less, $10^{-5}$ M or less, $10^{-6}$ M or less, $10^{-7}$ M or less, $10^{-8}$ M or less, $10^{-9}$ M or less, $10^{-10}$ M or less, $10^{-11}$ M or less, or $10^{-12}$ M or less under the conditions employed, e.g., under physiological conditions such as those inside a cell or consistent with cell survival. In some embodiments, specific binding can be accomplished by a plurality of weaker interactions (e.g., a plurality of individual interactions, wherein each individual interaction is characterized by a Kd of greater than $10^{-3}$ M). In some embodiments, specific binding, which can be referred to as "molecular recognition," is a saturable binding interaction between two entities that is dependent on complementary orientation of functional groups on each entity. Examples of specific binding interactions include aptamer-aptamer target interactions, antibody-antigen interactions, avidin-biotin interactions, ligand-receptor interactions, metal-chelate interactions, hybridization between complementary nucleic acids, etc.

The terms "sufficient" and "effective," as used interchangeably herein, can refer to an amount (e.g. mass, volume, dosage, concentration, and/or time period) needed to achieve one or more desired result(s). For example, a therapeutically effective amount refers to an amount needed to achieve one or more therapeutic effects.

As used herein, "synergistic effect," "synergism," or "synergy" can refer to an effect arising between two or more molecules, compounds, substances, factors, or compositions that that is greater than or different from the sum of their individual effects.

As used herein, "tangible medium of expression" can refer to a medium that is physically tangible and is not a mere abstract thought or an unrecorded spoken word. Tangible medium of expression includes, but is not limited to, words on a cellulosic or plastic material or data stored on a suitable device such as a flash memory or CD-ROM.

As used herein, "therapeutic", "treating", "treat" and the like can refer to include partially or completely delaying, alleviating, mitigating or reducing the intensity of one or more attendant symptoms of a disease or condition.

The term "alkyl" (or "lower alkyl") as used herein can include both "unsubstituted alkyls" and "substituted alkyls,"

the latter of which refers to alkyl moieties having one or more substituents replacing a hydrogen on one or more carbons of the hydrocarbon backbone. Such substituents include, but are not limited to, halogen, hydroxyl, carbonyl (such as a carboxyl, alkoxycarbonyl, formyl, or an acyl), thiocarbonyl (such as a thioester, a thioacetate, or a thioformate), alkoxyl, phosphoryl, phosphate, phosphonate, phosphinate, amino, amido, amidine, imine, cyano, nitro, azido, sulfhydryl, alkylthio, sulfate, sulfonate, sulfamoyl, sulfonamido, sulfonyl, heterocyclyl, aralkyl, or an aromatic or heteroaromatic moiety.

Unless the number of carbons is otherwise specified, "lower alkyl" as used herein can refer to an alkyl group, as defined above, but having from one to ten carbons in its backbone structure. Likewise, "lower alkenyl" and "lower alkynyl" have similar chain lengths.

It will be understood by those skilled in the art that the moieties substituted on the hydrocarbon chain can themselves be substituted, if appropriate. For instance, the substituents of a substituted alkyl may include halogen, hydroxy, nitro, thiols, amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), $-CF_3$, $-CN$ and the like. Cycloalkyls can be substituted in the same manner.

As used herein, "$C_{1-6}$alkyl" can refer to an alkyl group having any number of member atoms from 1 to 6 member atoms, such as for example 1 to 4 atoms. Other alkyl groups may have any number of member atoms as indicated by the numbers given in the formula, which, like the previous example, can refer to an alkyl group having any number of member atoms within the specified range of member atoms. Alkyl groups may be straight or branched. Representative branched alkyl groups have one, two, or three branches. Alkyl includes methyl, ethyl, propyl (n-propyl and isopropyl), butyl (n-butyl, isobutyl, and t-butyl), pentyl (n-pentyl, isopentyl, and neopentyl), and hexyl.

As used herein, "heterocyclic group" can refer to a non-aromatic ring and having the specified number of member atoms being saturated or having one or more degrees of unsaturation and, unless otherwise specified, containing one or more heteroatoms.

As used herein, "heteroaryl" can refer to an aromatic ring having the specified number of member atoms and, unless otherwise specified, containing one or more heteroatoms. Bicyclic and other polycyclic ring systems having a heteroaryl ring are described as fused systems.

The term "heteroalkyl," as used herein, can refer to straight or branched chain, or cyclic carbon-containing radicals, or combinations thereof, containing at least one heteroatom. Suitable heteroatoms include, but are not limited to, O, N, Si, P, Se, B, and S, wherein the phosphorous and sulfur atoms are optionally oxidized, and the nitrogen heteroatom is optionally quaternized. Heteroalkyls can be substituted as defined above for alkyl groups.

The term "heteroalkyl," as used herein, can refer to straight or branched chain, or cyclic carbon-containing radicals, or combinations thereof, containing at least one heteroatom. Suitable heteroatoms include, but are not limited to, O, N, Si, P, Se, B, and S, wherein the phosphorous and sulfur atoms are optionally oxidized, and the nitrogen heteroatom is optionally quaternized. Heteroalkyls can be substituted as defined above for alkyl groups.

As used herein, "alkoxyl" or "alkoxy," as used herein, can refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl is an ether or resembles an alkoxyl, such as can be represented by one of —O-alkyl, —O-alkenyl, and —O-alkynyl. The terms "aroxy" and "aryloxy", as used interchangeably herein, can be represented by —O-aryl or O-heteroaryl, wherein aryl and heteroaryl are as defined below. The alkoxy and aroxy groups can be substituted as described above for alkyl.

As used herein, "amine" and "amino" (and its protonated form) are art-recognized and refer to both unsubstituted and substituted amines, e.g., a moiety that can be represented by the general formula:

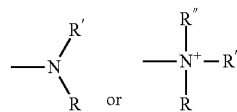

wherein R, R', and R" each independently represent a hydrogen, an alkyl, an alkenyl, $-(CH_2)_m-R_C$ or R and R' taken together with the N atom to which they are attached complete a heterocycle having from 4 to 8 atoms in the ring structure; $R_C$ represents an aryl, a cycloalkyl, a cycloalkenyl, a heterocycle or a polycycle; and m is zero or an integer in the range of 1 to 8. In some embodiments, only one of R or R' can be a carbonyl, e.g., R, R' and the nitrogen together do not form an imide. In other embodiments, the term "amine" does not encompass amides, e.g., wherein one of R and R' represents a carbonyl. In further embodiments, R and R' (and optionally R") each independently represent a hydrogen, an alkyl or cycloakly, an alkenyl or cycloalkenyl, or alkynyl. Thus, the term "alkylamine" as used herein means an amine group, as defined above, having a substituted (as described above for alkyl) or unsubstituted alkyl attached thereto, i.e., at least one of R and R' is an alkyl group.

As used herein, "amido" is art-recognized as an amino-substituted carbonyl and includes a moiety that can be represented by the general formula:

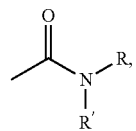

wherein R and R' are as defined above.

As used herein, "Aryl" can refer to $C_5$-$C_{10}$-membered aromatic, heterocyclic, fused aromatic, fused heterocyclic, biaromatic, or bihetereocyclic ring systems. Broadly defined, "aryl", as used herein, includes 5-, 6-, 7-, 8-, 9-, and 10-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine, pyrimidine, and the like. Those aryl groups having heteroatoms in the ring structure may also be referred to as "aryl heterocycles" or "heteroaromatics." The aromatic ring can be substituted at one or more ring positions with one or more substituents including, but not limited to, halogen, azide, alkyl, aralkyl, alkenyl, alkynyl, cycloalkyl, hydroxyl, alkoxyl, amino (or quaternized amino), nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —CF₃, —CN, and combinations thereof.

The term "aryl" can also include polycyclic ring systems having two or more cyclic rings in which two or more carbons are common to two adjoining rings (i.e., "fused rings") wherein at least one of the rings is aromatic, e.g., the other cyclic ring or rings can be cycloalkyls, cycloalkenyls, cycloalkynyls, aryls and/or heterocycles. Examples of heterocyclic rings include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4 aH carbazolyl, carbolinyl, chromanyl, chromenyl, cinnolinyl, decahydroquinolinyl, 2H,6H-1,5,2-dithiazinyl, dihydrofuro[2,3 b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, and xanthenyl. One or more of the rings can be substituted as defined above for "aryl."

As used herein, "aralkyl," can refer to an alkyl group substituted with an aryl group (e.g., an aromatic or heteroaromatic group).

As used herein, "aralkyloxy" can be represented by —O-aralkyl, wherein aralkyl is as defined above.

As used herein, "carbocycle," can refer to an aromatic or non-aromatic ring(s) in which each atom of the ring(s) is carbon.

As used herein, "heterocycle" or "heterocyclic" can refer to a monocyclic or bicyclic structure containing 3-10 ring atoms, and in some embodiments, containing from 5-6 ring atoms, wherein the ring atoms are carbon and one to four heteroatoms each selected from the following group of non-peroxide oxygen, sulfur, and N(Y) wherein Y is absent or is H, O, (C₁-C₁₀) alkyl, phenyl or benzyl, and optionally containing 1-3 double bonds and optionally substituted with one or more substituents. Examples of heterocyclic rings include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1,5,2-dithiazinyl, dihydrofuro[2,3 b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxepanyl, oxetanyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydropyranyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, and xanthenyl. Heterocyclic groups can optionally be substituted with one or more substituents at one or more positions as defined above for alkyl and aryl, for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, ether, alkylthio, sulfonyl, ketone, aldehyde, ester, a heterocyclyl, an aromatic or heteroaromatic moiety, —CF₃, —CN, or the like.

The term "carbonyl" is art-recognized and includes such moieties as can be represented by the general formula:

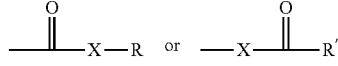

wherein X is a bond or represents an oxygen or a sulfur, and R and R' are as defined above. Where X is an oxygen and R or R' is not hydrogen, the formula represents an "ester". Where X is an oxygen and R is as defined above, the moiety is referred to herein as a carboxyl group, and particularly when R is a hydrogen, the formula represents a "carboxylic acid." Where X is an oxygen and R' is hydrogen, the formula represents a "formate." In general, where the oxygen atom of the above formula is replaced by sulfur, the formula represents a "thiocarbonyl" group. Where X is a sulfur and R or R' is not hydrogen, the formula represents a "thioester." Where X is a sulfur and R is hydrogen, the formula represents a "thiocarboxylic acid." Where X is a sulfur and R' is hydrogen, the formula represents a "thioformate." On the other hand, where X is a bond, and R is not hydrogen, the above formula represents a "ketone" group. Where X is a bond, and R is hydrogen, the above formula represents an "aldehyde" group.

As used herein, "heteroatom" as used herein can refer to an atom of any element other than carbon or hydrogen. Exemplary heteroatoms include, but are not limited to, boron, nitrogen, oxygen, phosphorus, sulfur, silicon, arsenic, and selenium.

As used herein, "nitro" can refer to —NO₂; the term "halogen" designates —F, —Cl, —Br, or —I; the term "sulfhydryl" refers to —SH; and the term "hydroxyl" refers to —OH.

As used herein, the term "sulfonyl" refers either to a functional group found primarily in sulfones or to a substituent obtained from a sulfonic acid by the removal of the hydroxyl group similarly to acyl groups. Sulfonyl groups have the general formula R—S(=O)2-R', where there are two double bonds between the sulfur and oxygen.

The term "substituted" as used herein, can refer to all permissible substituents of the compounds described herein. In the broadest sense, the permissible substituents include acyclic and cyclic, branched and unbranched, carbocyclic and heterocyclic, aromatic and nonaromatic substituents of organic compounds. Illustrative substituents include, but are not limited to, halogens, hydroxyl groups, or any other organic groupings containing any number of carbon atoms, e.g. 1-14 carbon atoms, and optionally include one or more heteroatoms such as oxygen, sulfur, or nitrogen grouping in linear, branched, or cyclic structural formats. Representative substituents include alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, amino acid, peptide, and polypeptide groups.

Heteroatoms, such as nitrogen, can have hydrogen substituents and/or any permissible substituents of organic compounds described herein which satisfy the valences of the heteroatoms. It is understood that "substitution" or "substituted" includes the implicit proviso that such substitution is in accordance with permitted valence of the substituted atom and the substituent, and that the substitution results in a stable compound, i.e., a compound that does not spontaneously undergo transformation such as by rearrangement, cyclization, elimination, etc.

As used herein, "suitable substituent" can refer to a chemically and pharmaceutically acceptable group, i.e., a moiety that does not significantly interfere with the preparation of or negate the efficacy of the inventive compounds. Such suitable substituents may be routinely chosen by those skilled in the art. Suitable substituents include but are not limited to the following: a halo, $C_1$-$C_6$ alkyl, $C_2$-$C_6$ alkenyl, $C_1$-$C_6$ haloalkyl, $C_1$-$C_6$ alkoxy, $C_1$-$C_6$ haloalkoxy, $C_2$-$C_6$ alkynyl, $C_3$-$C_8$ cycloalkenyl, ($C_3$-$C_8$ cycloalkyl)$C_1$-$C_6$ alkyl, ($C_3$-$C_8$ cycloalkyl)$C_2$-$C_6$ alkenyl, ($C_3$-$C_8$ cycloalkyl) $C_1$-$C_6$ alkoxy, $C_3$-$C_7$ heterocycloalkyl, ($C_3$-$C_7$ heterocycloalkyl) $C_1$-$C_6$ alkyl, ($C_3$-$C_7$ heterocycloalkyl)$C_2$-$C_6$ alkenyl, ($C_3$-$C_7$ heterocycloalkyl)$C_1$-$C_6$ alkoxyl, hydroxy, carboxy, oxo, sulfanyl, $C_1$-$C_6$ alkylsulfanyl, aryl, heteroaryl, aryloxy, heteroaryloxy, arylalkyl, heteroaralkyl, arylalkoxy, heteroaralkoxy, nitro, cyano, amino, $C_1$-$C_6$ alkylamino, di-($C_1$-$C_6$ alkyl)amino, carbamoyl, ($C_1$-$C_6$ alkyl)carbonyl, ($C_1$-$C_6$ alkoxy)carbonyl, ($C_1$-$C_6$ alkyl)aminocarbonyl, di-($C_1$-$C_6$ alkyl)aminocarbonyl, arylcarbonyl, aryloxycarbonyl, ($C_1$-$C_6$ alkyl)sulfonyl, and arylsulfonyl. The groups listed above as suitable substituents are as defined hereinafter except that a suitable substituent may not be further optionally substituted.

As used herein, "optionally substituted" can indicate that a group may be unsubstituted or substituted with one or more substituents as defined herein.

As used herein, "about" indicates ±5% of the reference value, in an embodiment. In another embodiment, "about" indicates ±10% of the reference value. In another embodiment, "about" indicates ±1% of the reference value.

Other compositions, compounds, methods, features, and advantages of the present disclosure will be or become apparent to one having ordinary skill in the art upon examination of the following drawings, detailed description, and examples. It is intended that all such additional compositions, compounds, methods, features, and advantages be included within this description, and be within the scope of the present disclosure.

The present invention has been described in terms of one or more preferred embodiments, and it should be appreciated that many equivalents, alternatives, variations, and modifications, aside from those expressly stated, are possible and within the scope of the invention.

Sulfono-γ-AA Peptides

Described herein are novel sulfono-γ-AA peptides that mimic vascular endothelial growth factor (VEGF), and bind to VEGF receptors (VEGF-R).

In an embodiment, the sulfono-γ-AA peptide has the chemical formula $C_{93}H_{165}N_{21}O_{29}S_8$, and the structure of Formula 1:

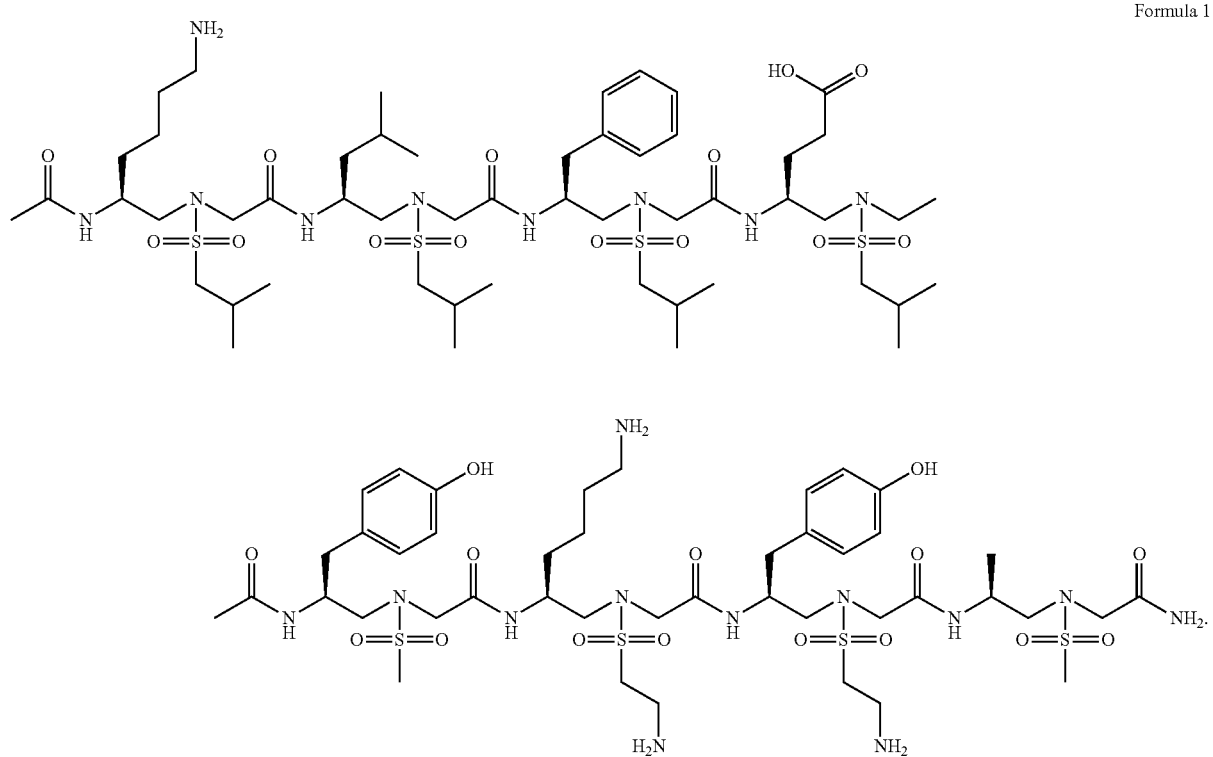

Formula 1

In an embodiment, the sulfono-γ-AA peptide has the chemical formula $C_{87}H_{151}N_{21}O_{31}S_8$, and the structure of Formula 2:

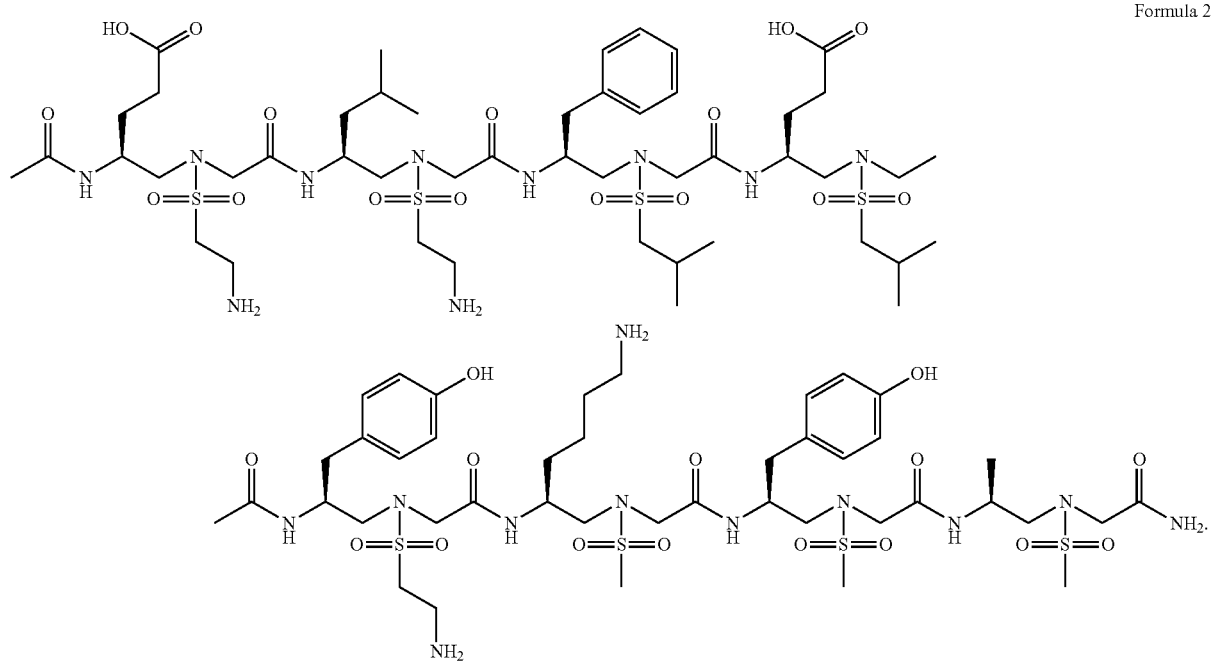

Formula 2

In an embodiment, the sulfono-γ-AA peptide has the chemical formula $C_{89}H_{152}N_{22}O_{31}S_8$, and the structure of Formula 3:

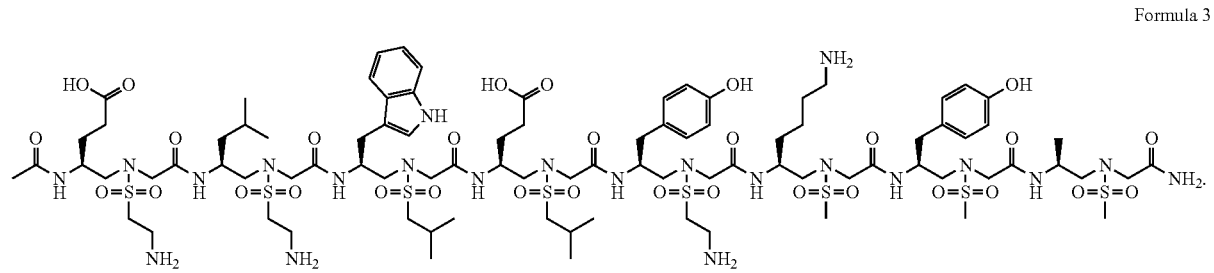 [SMILES: CC(=O)N[C@@H](CCC(=O)O)CN(CC(=O)N[C@@H](CC(C)C)CN(CC(=O)N[C@@H](Cc1c[nH]c2ccccc12)CN(CC(=O)N[C@@H](CCC(=O)O)CN(CC(=O)N[C@@H](Cc1ccc(O)cc1)CN(CC(=O)N[C@@H](CCCCN)CN(CC(=O)N[C@@H](Cc1ccc(O)cc1)CN(CC(=O)N[C@@H](C)CN(CC(N)=O)S(C)(=O)=O)S(C)(=O)=O)S(C)(=O)=O)S(=O)(=O)CCN)S(=O)(=O)CC(C)C)S(=O)(=O)CC(C)C)S(=O)(=O)CCN)S(=O)(=O)CCN]

Formula 3

Pharmaceutical Compositions of Sulfono-γ-AA Peptides

In an embodiment, provided herein are pharmaceutical compositions comprising the peptides of Formula 1, Formula 2, or Formula 3, or structural analogues thereof; and a pharmaceutically acceptable carrier.

In an embodiment, a pharmaceutical composition comprises at least one of the peptides of Formula 1, Formula 2, or Formula 3, or structural analogues thereof, and a pharmaceutically acceptable carrier.

In an embodiment, a pharmaceutical composition comprises both of the peptides of Formula 1, Formula 3, or structural analogues thereof, and a pharmaceutically acceptable carrier.

The peptides described herein can be provided to a subject in need thereof as an ingredient, such as an active ingredient, in a pharmaceutical composition. As such, also described are pharmaceutical formulations containing one or more of the peptides/compounds and salts thereof, or pharmaceutically acceptable salts thereof described herein. Suitable salts include, hydrobromide, iodide, nitrate, bisulfate, phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, camphorsulfonate, napthalenesulfonate, propionate, malonate, mandelate, malate, phthalate, and pamoate.

The pharmaceutical compositions or salts thereof can be administered to a subject in need thereof, a population of cells, and/or a population of cells in a subject in need thereof. In some embodiments, the subject in need thereof to which the pharmaceutical compositions comprising at least one of the peptides of Formula 1, Formula 3, or structural analogues thereof is administered has a disease or disorder in which reducing angiogenesis would reduce or prevent increased symptoms of such disease or disorder, e.g. cancer or retinopathy.

The pharmaceutical compositions or salts thereof can be administered to a subject in need thereof, a population of cells, and/or a population of cells in a subject in need thereof. In some embodiments, the subject in need thereof to which the pharmaceutical compositions comprising the peptide/compound of Formula 2, or a structural analogue thereof is administered has a disease or disorder in which increasing angiogenesis would reduce or prevent increased symptoms of such disease or disorder, e.g. ischemic heart disease. In some embodiments, the subject in need thereof is experiencing a wound or organ damage.

Pharmaceutically Acceptable Carriers and Auxiliary Ingredients and Agents

The pharmaceutical formulations containing an amount, such as an effective amount, least effective amount, and/or pharmaceutically effective amount of a compound described herein, or a derivative thereof can further include a pharmaceutically acceptable carrier. Suitable pharmaceutically acceptable carriers include, but are not limited to water, salt solutions, alcohols, gum arabic, vegetable oils, benzyl alcohols, polyethylene glycols, gelatin, carbohydrates such as lactose, amylose or starch, magnesium stearate, talc, silicic acid, viscous paraffin, perfume oil, fatty acid esters, hydroxy methylcellulose, and polyvinyl pyrrolidone, which do not deleteriously react with the active composition.

The pharmaceutical formulations can be sterilized, and if desired, mixed with auxiliary agents, such as lubricants, preservatives, stabilizers, wetting agents, emulsifiers, salts for influencing osmotic pressure, buffers, coloring, flavoring and/or aromatic substances, and the like which do not deleteriously react with the active compound.

In addition to the effective amount of a compound and/or derivative thereof, the pharmaceutical formulations can also include an effective amount of auxiliary active agents, including but not limited to, antisense or RNA interference molecules, chemotherapeutics, or antineoplasic agents, hormones, antibiotics, antivirals, immunomodulating agents, antinausea, pain modifying compounds (such as opiates), anti-inflammatory agents, antipyretics, antibiotics, and/or antibodies or fragments thereof.

Effective amounts of the Sulfono-γ-AA Peptide and Auxiliary Active Agents

In some embodiments, the effective amount, least effective amount, and/or pharmaceutically effective amount of the sulfono-γ-AA peptide having a Formula according to Formula 1, Formula 3, or structural analogues thereof can reduce characteristics of angiogenesis, e.g. cell migration and capillary tube formation in a subject in need thereof or a population of cells. In some embodiments, the effective amount, least effective amount, and/or pharmaceutically effective amount of the sulfono-γ-AA peptide having a Formula according to Formula 2, or a structural analogue thereof can increase characteristics of angiogenesis, e.g. cell migration and capillary tube formation in a subject in need thereof or a population of cells.

In some embodiments, the effective amount, least effective amount, and/or pharmaceutically effective amount of the sulfono-γ-AA peptide having a Formula according to Formula 1, Formula 3, or structural analogues thereof can reduce characteristics of angiogenesis in a subject having or suspected of a cancer or retinopathy. In some embodiments, the effective amount, least effective amount, and/or pharmaceutically effective amount of the sulfono-γ-AA peptide having a Formula according to Formula 2, or a structural analogue thereof can increase characteristics of angiogenesis in a subject having or suspected of having ischemic heart disease, a wound, or organ damage.

The effective amount, least effective amount, and/or pharmaceutically effective amount of the sulfono-γ-AA peptide that can have a structure according to Formula 1, Formula 2, Formula 3, or structural analogues thereof contained in the pharmaceutical composition/formulation can range from about 0.001 micrograms to about 1000 grams, about 0.01 micrograms to about 100 grams, about 0.1 micrograms to about 10 grams, or about 1 microgram to about 1 gram, about 10 micrograms to about 100 mg, 100 micrograms to about 10 mg, or about 1 mg to about 5 mg. In some embodiments, the effective concentration can range from about 1 pM to about 100 nM, about 10 pM to about 10 nM, or about 100 pM, to about 1 nM.

In embodiments where there is an auxiliary active agent contained in the compound or derivative thereof pharmaceutical formulation, the effective amount of the auxiliary active agent will vary depending on the auxiliary active agent. In some embodiments, the effective amount of the auxiliary active agent can range from 0.001 micrograms to about 1000 grams. In other embodiments, the effective amount of the auxiliary active agent can range from about 0.01 IU to about 1000 IU. In further embodiments, the effective amount of the auxiliary active agent can range from 0.001 mL to about 1000 mL. In yet other embodiments, the effective amount of the auxiliary active agent can range from about 1% w/w to about 50% w/w of the total pharmaceutical formulation. In additional embodiments, the effective amount of the auxiliary active agent can range from about 1% v/v to about 50% v/v of the total pharmaceutical formulation. In still other embodiments, the effective amount of the auxiliary active agent can range from about 1% w/v to about 50% w/v of the total pharmaceutical formulation.

The auxiliary active agent can be included in the pharmaceutical formulation or can exist as a stand-alone compound or pharmaceutical formulation that can be administered contemporaneously or sequentially with the compound, derivative thereof, or pharmaceutical formulation thereof. In embodiments where the auxiliary active agent is a stand-alone compound or pharmaceutical formulation, the effective amount of the auxiliary active agent can vary depending on the auxiliary active agent used. In some of these embodiments, the effective amount of the auxiliary active agent can range from 0.001 micrograms to about 1000 grams. In other embodiments, the effective amount of the auxiliary active agent can range from about 0.01 IU to about 1000 IU. In further embodiments, the effective amount of the auxiliary active agent can range from 0.001 mL to about 1000 mL. In yet other embodiments, the effective amount of the auxiliary active agent can range from about 1% w/w to about 50% w/w of the total auxiliary active agent pharmaceutical formulation. In additional embodiments, the effective amount of the auxiliary active agent can range from about 1% v/v to about 50% v/v of the total pharmaceutical formulation. In still other embodiments, the effective amount of the auxiliary active agent can range from about 1% w/v to about 50% w/v of the total auxiliary agent pharmaceutical formulation.

Dosage Forms

In some embodiments, the pharmaceutical formulations described herein can be in a dosage form. The dosage forms can be adapted for administration by any appropriate route. Appropriate routes include, but are not limited to, oral (including buccal or sublingual), rectal, intraocular, inhaled, intranasal, topical (including buccal, sublingual, or transdermal), vaginal, parenteral, subcutaneous, intramuscular, intravenous, internasal, and intradermal. Such formulations can be prepared by any method known in the art.

Dosage forms adapted for oral administration can discrete dosage units such as capsules, pellets or tablets, powders or granules, solutions, or suspensions in aqueous or non-aqueous liquids; edible foams or whips, or in oil-in-water liquid emulsions or water-in-oil liquid emulsions. In some embodiments, the pharmaceutical formulations adapted for oral administration also include one or more agents which flavor, preserve, color, or help disperse the pharmaceutical formulation. Dosage forms prepared for oral administration can also be in the form of a liquid solution that can be delivered as a foam, spray, or liquid solution.

The oral dosage form can be administered to a subject in need thereof. The oral dosage form can be administered to a subject in need thereof, a population of cells, and/or a population of cells in a subject in need thereof. Where appropriate, the dosage forms described herein can be microencapsulated. The dosage form can also be prepared to prolong or sustain the release of any ingredient. In some embodiments, the sulfono-γ-AA peptide/compound of Formula 1, Formula 2, or Formula 3 or structural analogues thereof, the auxiliary active ingredient, and/or the pharmaceutically acceptable salt thereof can be an ingredient whose release is delayed. Suitable methods for delaying the release of an ingredient include, but are not limited to, coating or embedding the ingredients in material in polymers, wax, gels, and the like. Delayed release dosage formulations can be prepared as described in standard references such as "Pharmaceutical dosage form tablets," eds. Liberman et. al. (New York, Marcel Dekker, Inc., 1989), "Remington—The science and practice of pharmacy", 20th ed., Lippincott Williams & Wilkins, Baltimore, MD, 2000, and "Pharmaceutical dosage forms and drug delivery systems", 6th Edition, Ansel et al., (Media, P A: Williams and Wilkins, 1995). These references provide information on excipients, materials, equipment, and processes for preparing tablets and capsules and delayed release dosage forms of tablets and pellets, capsules, and granules. The delayed release can be anywhere from about an hour to about 3 months or more.

Examples of suitable coating materials include, but are not limited to, cellulose polymers such as cellulose acetate phthalate, hydroxypropyl cellulose, hydroxypropyl methylcellulose, hydroxypropyl methylcellulose phthalate, and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides.

Coatings may be formed with a different ratio of water soluble polymer, water insoluble polymers, and/or pH dependent polymers, with or without water insoluble/water soluble non polymeric excipient, to produce the desired release profile. The coating is either performed on the dosage form (matrix or simple) which includes, but is not limited to, tablets (compressed with or without coated beads), capsules (with or without coated beads), beads, particle compositions, "ingredient as is" formulated as, but not limited to, suspension form or as a sprinkle dosage form.

Where appropriate, the dosage form described herein can be a liposome. In embodiments, the peptide/compound, derivative thereof, auxiliary active ingredient, and/or pharmaceutically acceptable salt thereof are incorporated into a liposome. In some embodiments, the composition is integrated into the lipid membrane of the liposome. In other embodiments, the composition is contained in the aqueous phase of the liposome. In embodiments where the dosage form is a liposome, the pharmaceutical formulation is thus a liposomal formulation.

Dosage forms adapted for topical administration can be formulated as ointments, creams, suspensions, lotions, powders, solutions, pastes, gels, sprays, aerosols, or oils. In some embodiments for treatments of the eye or other external tissues, for example the mouth or the skin, the pharmaceutical formulations are applied as a topical ointment or cream. When formulated in an ointment, the composition may be formulated with a paraffinic or water-miscible ointment base. In other embodiments, the active ingredient can be formulated in a cream with an oil-in-water cream base or a water-in-oil base. Dosage forms adapted for topical administration in the mouth include lozenges, pastilles, and mouth washes.

Dosage forms adapted for nasal or inhalation administration include aerosols, solutions, suspension drops, gels, or dry powders. In some embodiments, the composition in a dosage form adapted for inhalation is in a particle-size-reduced form that is obtained or obtainable by micronization. In some embodiments, the particle size of the size reduced (e.g. micronized) compound or salt or solvate thereof, is defined by a D50 value of about 0.5 to about 10 microns as measured by an appropriate method known in the art. Dosage forms adapted for administration by inhalation also include particle dusts or mists. Suitable dosage forms wherein the carrier or excipient is a liquid for administration as a nasal spray or drops include aqueous or oil solutions/suspensions of an active ingredient, which may be generated by various types of metered dose pressurized aerosols, nebulizers, or insufflators. In some embodiments, the aerosol formulations are arranged so that each metered dose of aerosol contains a predetermined amount of an active ingredient, such as the one or more of the compounds described herein. The nasal/inhalation formulations can be administered to a subject in need thereof.

In some embodiments, the dosage forms are aerosol formulations suitable for administration by inhalation. In some of these embodiments, the aerosol formulation contains a solution or fine suspension of a peptide or composition described herein and a pharmaceutically acceptable aqueous or non-aqueous solvent. Aerosol formulations can be presented in single or multi-dose quantities in sterile form in a sealed container. For some of these embodiments, the sealed container is a single dose or multi-dose nasal or an aerosol dispenser fitted with a metering valve (e.g. metered dose inhaler), which is intended for disposal once the contents of the container have been exhausted. Where the aerosol dosage form is contained in an aerosol dispenser, the dispenser contains a suitable propellant under pressure, such as compressed air, carbon dioxide, or an organic propellant, including but not limited to a hydrofluorocarbon. The aerosol formulation dosage forms in other embodiments are contained in a pump-atomizer. The pressurized aerosol formulation can also contain a solution or a suspension of a peptide or composition described herein, an auxiliary active ingredient, and/or pharmaceutically acceptable salt thereof. In further embodiments, the aerosol formulation also contains co-solvents and/or modifiers incorporated to improve, for example, the stability and/or taste and/or fine particle mass characteristics (amount and/or profile) of the formulation. Administration of the aerosol formulation can be once daily or several times daily, for example 2, 3, 4, or 8 times daily, in which 1, 2, or 3 doses are delivered each time. The aerosol formulations can be administered to a subject in need thereof.

For some dosage forms suitable and/or adapted for inhaled administration, the pharmaceutical formulation is a dry powder inhalable formulation. In addition to a peptide or composition described herein, such a dosage form can contain a powder base such as lactose, glucose, trehalose, manitol, and/or starch. In some of these embodiments, the peptide or composition is in a particle-size reduced form. In further embodiments, a performance modifier, such as L-leucine or another amino acid, cellobiose octaacetate, and/or metals salts of stearic acid, such as magnesium or calcium stearate.

Dosage forms adapted for parenteral administration and/or adapted for injection can include aqueous and/or non-aqueous sterile injection solutions, which can contain antioxidants, buffers, bacteriostats, solutes that render the composition isotonic with the blood of the subject, and aqueous and non-aqueous sterile suspensions, which can include suspending agents and thickening agents. The dosage forms adapted for parenteral administration can be presented in a single-unit dose or multi-unit dose containers, including but not limited to sealed ampoules or vials. The doses can be lyophilized and re-suspended in a sterile carrier to reconstitute the dose prior to administration. Extemporaneous injection solutions and suspensions can be prepared in some embodiments, from sterile powders, granules, and tablets. The parenteral formulations can be administered to a subject in need thereof.

For some embodiments, the dosage form contains a predetermined amount of a peptide/compound of Formula 1, Formula 2, Formula 3, or structural analogues thereof, auxiliary active ingredient, and/or pharmaceutically acceptable salt thereof per unit dose. In other embodiments, the predetermined amount of the compound and/or derivative thereof can be an appropriate fraction of the effective amount of the active ingredient. Such unit doses may therefore be administered once or more than once a day (e.g. 1, 2, 3, 4, 5, 6, or more times per day). Such pharmaceutical formulations may be prepared by any of the methods well known in the art.

Methods of Making the Sulfono-γ-AA Peptides

The peptides/compounds and derivatives thereof can be synthesized via many methods generally known to those of ordinary skill in the art. The present disclosure is not intended to be limited by the particular methods of synthesizing the compounds described herein. The skilled artisan will recognize additional methods of synthesizing the compounds described herein.

Methods of Using the Pharmaceutical Formulations

Any amount of the pharmaceutical formulations described herein can be administered to a subject in need thereof one or more times per day, week, month, or year. In some embodiments, the pharmaceutical formulation administered contains an effective amount, a least effective amount, and/or a pharmaceutically effective amount of the peptide/compound of Formula 1, Formula 2, Formula 3, or structural analogues thereof. For example, the pharmaceutical formulations can be administered in a daily dose. This amount may be given in a single dose per day. In other embodiments, the daily dose may be administered over multiple doses per day, in which each containing a fraction of the total daily dose to be administered (sub-doses). In some embodiments, the amount of doses delivered per day is 2, 3, 4, 5, or 6. In further embodiments, the compounds, formulations, or salts thereof are administered one or more times per week, such as 1, 2, 3, 4, 5, or 6 times per week. In other embodiments, the compounds, formulations, or salts thereof are administered one or more times per month, such as 1 to 5 times per month. In still further embodiments, the compounds, formulations, or salts thereof are administered one or more times per year, such as 1 to 11 times per year. a neurodegenerative disease.

In embodiments where more than one of compounds, formulations, additional therapeutic agents, salts thereof, or pharmaceutically acceptable salts thereof are administered to a subject in need thereof sequentially; the sequential administration may be close in time or remote in time. For example, administration of the second compound, formulation, or other therapeutic agent can occur within seconds or minutes (up to about 1 hour) after administration of the first agent (close in time). In other embodiments, administration of the second compound, formulation, or other therapeutic agent occurs at some other time that is more than an hour after administration of the first agent.

The amount of pharmaceutical formulations described herein can be administered in an amount ranging from about 0.01 mg to about 1000 mg per day, as calculated as the free or unsalted compound having a structure according to Formula 1 or structural analogue thereof. The amount can also be a concentration of about 0.1 μM to about 50 μM or about 0.1 μM to about 200 μM.

The pharmaceutical formulations provided herein can be administered in combinations with or include one or more other auxiliary agents. Suitable auxiliary agents include, but are not limited to antisense or RNA interference molecules, chemotherapeutics, anti-neoplasic agents, hormones, antibiotics, antivirals, immunomodulating agents, anti-nausea, pain modifying compounds (such as opiates), anti-inflammatory agents, antipyretics, antibiotics, and/or antibodies or fragments thereof. The compound(s), and/or formulation(s), and/or additional therapeutic agent(s) can be administered simultaneously or sequentially by any convenient route in separate or combined pharmaceutical formulations. The additional therapeutic agents can be provided in their optically pure form or a pharmaceutically acceptable salt thereof Kits The pharmaceutical compositions/formulations provided herein can be presented as a combination kit. As used herein, the terms "combination kit" or "kit of parts" refers to the compounds, or pharmaceutical formulations and additional components that are used to package, sell, market, deliver, and/or administer the combination of elements or a single element, such as the active ingredient, contained therein. Such additional components include but are not limited to, packaging, syringes, blister packages, bottles, and the like. When one or more of the components (e.g. active agents) contained in the kit are administered simultaneously, the combination kit can contain the active agents in a single pharmaceutical formulation (e.g. a tablet) or in separate pharmaceutical formulations.

When the agents are not administered simultaneously, the combination kit can contain each agent in separate pharmaceutical formulations. The separate pharmaceutical formulations can be contained in a single package or in separate packages within the kit.

In some embodiments, the combination kit also includes instructions printed on or otherwise contained in a tangible medium of expression. The instructions can provide information regarding the content of the compound or pharmaceutical formulations contained therein, safety information regarding the content of the compound(s) or pharmaceutical formulation(s) contained therein, information regarding the dosages, indications for use, and/or recommended treatment regimen(s) for the compound(s) and/or pharmaceutical formulations contained therein. In some embodiments, the instructions can provide directions for administering the compounds, pharmaceutical formulations, or salts thereof to a subject in need thereof. In some aspects, the instructions can provide directions for administering the compounds, pharmaceutical formulations, or salts thereof to a subject having a disease or disorder in which working memory is impaired. In some aspects, the instructions can provide directions for administering the compounds, pharmaceutical formulations, or salts thereof to a subject having a disease or disorder in which cell viability (for example neuronal or spleen) is impaired. Suitable assays to assay working memory and cellular viability are known in the art. Other suitable assays will be appreciated by those of ordinary skill in the art. the instructions can provide directions for administering the compounds, pharmaceutical formulations, or salts thereof to a subject having a disease or disorder of the nervous system.

EXAMPLES

Example 1

Introduction

Angiogenesis, formation of new blood vessels from the existing vascular network, is a hallmark of cancer cells that leads to tumor vascular proliferation and metastasis. This process is mediated through the binding interaction of VEGF-A with VEGF receptors. However, the balance between pro-angiogenic and anti-angiogenic effect after ligand binding yet remains elusive and is therefore challenging to manipulate.

The binding interface of VEGF-A, residues (8-109), consists of two monomers linked with two disulfide bridges and two binding interfaces located opposite each other on each monomer. The crystal structure of VEGF-A bound to VEGFR-2 (3V2A) and alanine mutagenesis studies reveal that the VEGF N-terminal helix-α1 (residues 16-25) is a major binding interface for VEGF-VEGFR protein-protein interaction (PPI), in which residues Phe17, Met18, Tyr21, and Tyr25 make up the focal points of this PPI (FIG. 1).[31] For instance, alanine mutagenesis of Phe17 results in a 90-fold decrease in binding, delineating Phe17 as one of the most important residues on helix-α1 for the binding interaction.[31,32] A peptide QK, designed based on helix-α1, has been shown to have good binding affinity to VEGFR and activated angiogenesis.[33] Another peptide, MA, directly reproducing VEGF al helix 17-25, also demonstrated binding to VEGF receptors.[34] Interestingly, with differences of only two amino acid residues in the whole peptide sequence compared with QK, MA was capable of inhibiting angiogenesis.[34] The inventors speculated that the contradictory effect of these two peptides on angiogenesis was due to the different conformations adopted by VEGFR upon binding of these peptides. Although the molecular mechanism remains elusive, their effectiveness in regulating angiogenesis renders them potential candidates for future exploration. However, it is known that peptides of natural amino acids fall short in stability toward proteolytic enzymes, hence generally have low therapeutic potentials.[35]

As protein-protein interactions mediate virtually all biological processes and represent unparalleled potential targets for novel therapeutics, tremendous efforts have been undertaken in recent years toward effective PPI modulations.[36-38] Peptides and peptidomimetics offer exceptional prospects of mimicking protein domains essential for PPIs, with the latter offering unique advantages with respect to stability and bioavailability.[39,40] Some notable peptidomimetics developed so far include peptoids,[41,42] β-peptides,[43,44] α/β-peptides,[45-48] azapeptides,[49,50] oligoureas,[51,52] and others.[53-55] α/β-Peptides derived from Z domain peptides were particularly shown to bind to VEGFR and to have more resistance to proteases than α-peptides.[46]

γ-AA peptides are a unique class of peptidomimetics with exceptional stability, diversity, and protein domain mimicking capability.[56-58] The inventors have previously reported crystal structures of sulfono-γ-AA peptides adopting a left-handed helix capable of multiface recognition and binding interactions toward target proteins (FIG. 2) due to their similarity to an α-helix.[59-64] Their helical propensity is even superior to the α-helix, possibly due to the synergy of both intramolecular hydrogen bonding and the curved nature of sulfonamido moieties forcing the formation of helical turns. Together with other remarkable features including chemodiversity and resistance to enzymatic degradation, helical sulfono-γ-AA peptides may enable targeting of a wide array of therapeutically relevant PPIs.

Herein, the inventors report rationally designed sulfono-γ-AA peptide based peptidomimetics of VEGF-A. The inventors designed a few unnatural sulfono-γ-AA peptide foldamers to mimic the helical binding domain of VEGF-A: helix-α1 (16-25). These helical mimics were designed based on the X-ray crystal structure of VEGFR-2/VEGF-A (3V2A) and the alanine mutagenesis data to mimic the three-dimensional spatial orientation of the key binding residues: Phe17, Met18, Tyr21, and Tyr25.[65] These helical mimics were shown to bind VEGFR1 and VEGFR2 with high affinity and specificity. Cell-based studies demonstrated that these sulfono-γ-AA peptide mimics of VEGF-A could effectively downregulate and, with a subtle change of a side chain, upregulate angiogenesis. On the basis of the results, the inventors hypothesized that the inverse angiogenesis signaling was due to the selective binding of helical mimetics toward either VEGFR1 or VEGFR2, respectively. Moreover, these helical mimetic sequences demonstrate exceptional proteolytic stability, highlighting their potential as molecular probes to unravel mechanisms of angiogenesis and therapeutic agents targeting angiogenesis.

Results

Design of Sulfono-γ-AA Peptide Mimics of VEGF.

The design of VEGF-mimicking sulfono-γ-AA peptides was based on the positioning of the key binding residues (Phe17, Met18, Tyr21, and Tyr25) on the helical binding domain, helix-α1 of VEGF-A, featured on the crystal structure of the VEGFR-2/VEGF-A complex (FIG. 3A, PDB: 3V2A). Phe17, Tyr21, and Tyr25 are positioned on the same face of the helical binding domain (FIG. 3B). As shown in FIG. 2B, these functional groups could be reproduced by the side chains at 3a, 5a, and 7a positions in sulfono-γ-AA peptides, respectively. The additional residue Met18 could be mimicked with a hydrophobic and relatively sized sulfono isobutyl group at position 4b. An overlay of a sulfono-γ-AA peptide V3 (FIG. 12) with the helical domain of VEGFR2 shows that the designed side chains on the positions overlap with Phe17, Met18, Tyr21, and Tyr25 very well (FIG. 3B). To this end, a series of sulfono-γ-AA peptides (V1-V4) were designed and synthesized along with a negative control sulfono-γ-AA peptide bearing alanine-like side chains (V5) (FIG. 12).

Binding Assays.

Surface plasmon resonance (SPR) assays were carried out to determine the binding affinities of the VEGF mimic sequences toward the extracellular domains of VEGFR-1 and VEGFR-2 (FIGS. 13 and 14). Excitingly, V1, V2, and V3 demonstrated good binding affinities toward VEGFRs. Particularly, with only one residue difference at the position 3a, V2 and V3 displayed remarkable selectivity for VEGFR1 and VEGFR2, revealing submicromolar binding affinity to VEGFR-1 and VEGFR-2, respectively. As expected, V4, which lacks a critical binding residue at position 3a to mimic F17 in VEGF-A-helix-α1 and V5, with all residues replaced with alanine, had no detectable binding. The binding studies demonstrated that sulfono-γ-AA peptides could mimic VEGF-A-helix-α1 and exhibit good binding specificity and affinity toward VEGFRs.

Circular Dichroism (CD) Measurements.

Figure 4:
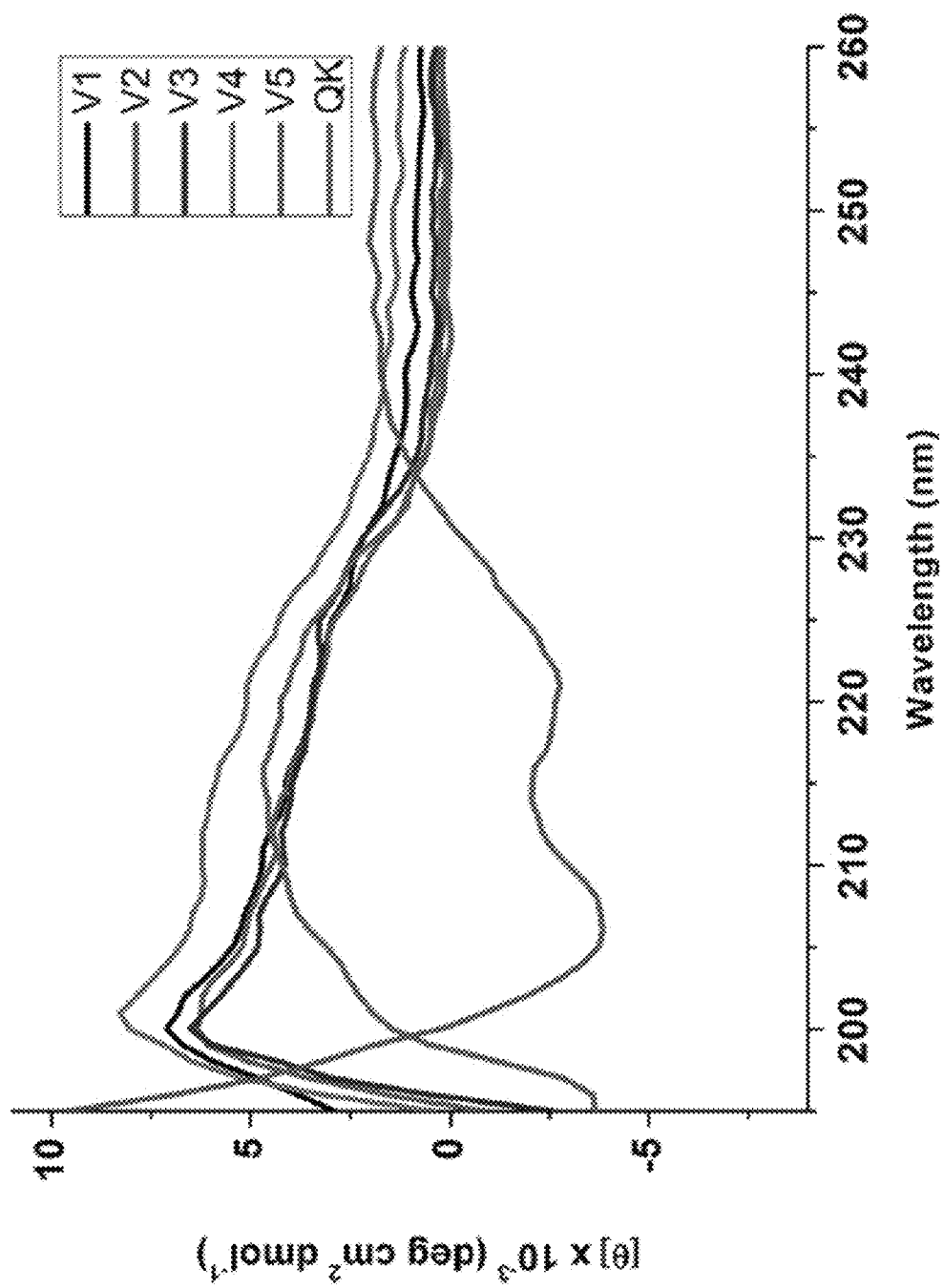
FIG. 4. CD spectra of sulfono-γ-AA peptides V1-V5 and QK measured at 100 μM, room temperature in PBS buffer.

CD studies were next conducted to assess the helicity of the VEGF-mimicking sulfono-γ-AA peptides. The studies were carried out in PBS buffer and monitored between 190 and 260 nm. In line with the inventors' previous reports,[60] sulfono-γ-AA peptides V1-V5 adopted a left-handed helical conformation with a Cotton effect maximum between 200 and 215 nm. For comparison, the reference peptide QK, an agonist reported by D'Andrea et al.,[33] was also synthesized and included as a control. Indeed, QK exhibited a characteristic double minimum Cotton effect, confirming a right-handed helix conformation, consistent with previous reports (FIG. 4).

In Vitro Angiogenesis Assays.

Activation of VEGFR-2 leads to endothelial cell proliferation, migration, and vascular formation.[66] To assess the effect of the VEGF mimics on the VEGF signaling pathway, the inventors conducted in vitro angiogenesis assays and examined the effect of these helix-mimicking sequences on cellular responses mediated through the activation of VEGFR-2. To ascertain that the observed effects were the result of the sulfono-γ-AA peptides interacting with VEGFR-2, pVEGR-2 and a key VEGF downstream signal (Akt) were monitored with Western blotting.

Cell Migration Assay.

Figure 5A:
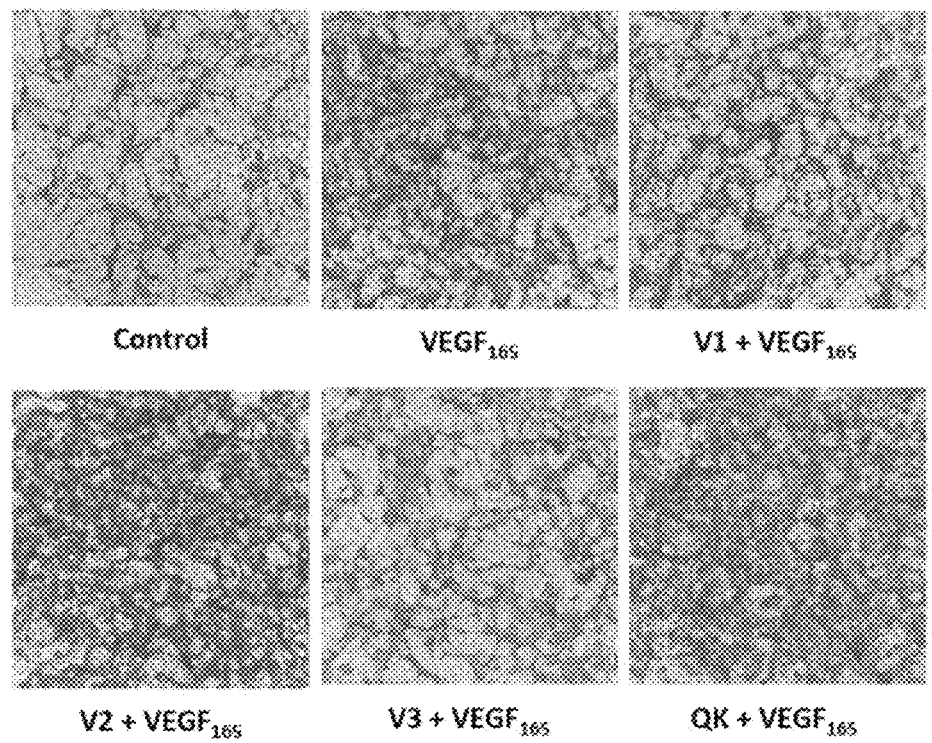
FIGS. 5A-5B. Transwell migration assay of HUVECs following treatment with VEGF mimics in the presence of $VEGF_{165}$.
Figure 5B:
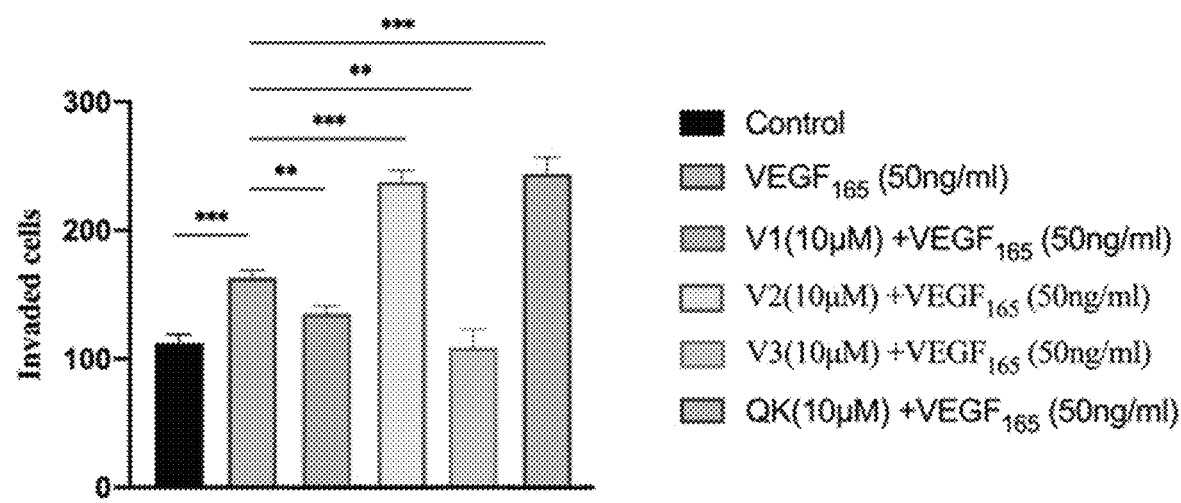

Endothelial cell migration is an essential component of angiogenesis mediated by the VEGF pathway and can be used to assess the effect of drugs on the VEGF pathway. A Transwell migration assay was used to test the effect of the mimic sequences on the migration of human umbilical endothelial cells (HUVECs). In the presence of $VEGF_{165}$, the number of HUVECs migrating was significantly lowered by V1 and V3, suggesting both sequences inhibited VEGF-stimulated VEGFR2 signaling, possibly because these sequences mimicked VEGF helix-α1 and blocked the binding of VEGF to VEGFR2. However, intriguingly, V2 markedly increased the number of HUVECs migrating. It was noted that QK also had a strong migration-stimulating effect, in line with its previously reported pro-angiogenic effect.[33] The results suggested that V2, similar to QK, could somehow enhance VEGFR2 signaling (FIG. 5). Given the findings that V2 has a much stronger binding affinity for VEGFR1 than VEGFR2 (FIG. 12), the inventors speculated that this stimulatory effect may be due to its specific binding to VEGFR1, the decoy receptor. It is plausible that inhibition of VEGF-A binding to VEGFR-1 leads to an increased level of VEGF-A to bind and activate VEGFR-2, an indirect activation of the main angiogenic receptor.67

Wound Healing Assay.

Figures 6A, 6B:
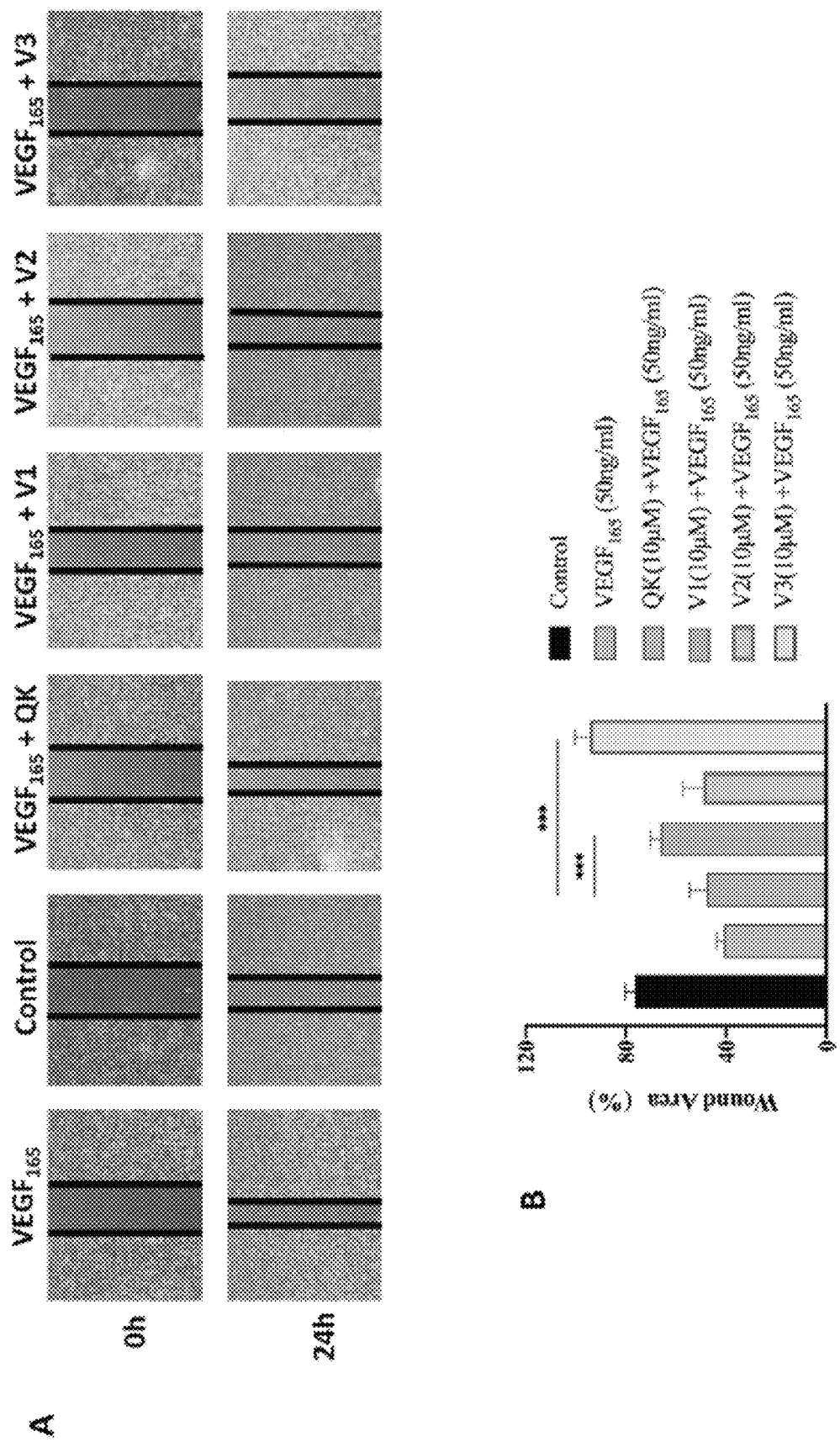
FIGS. 6A-6B. Wound healing assay.

Wound healing is facilitated by the VEGF pathway's effect on cell migration and proliferation.14 The effect of the helical mimic sequences on cell migration and invasion was tested on HUVECs in the presence of $VEGF_{165}$ using a scratch-wound motility assay. Consistent with the cell migration assay, the results (FIG. 6) show marked prevention of cell migration by V1 and V3 upon stimulation with VEGF, in which V3 virtually completely blocked wound motility at 10 μM, consistent with its strongest binding affinity toward VEGFR2. However, V2 and QK did not exhibit inhibition of migration in this assay.

Capillary Tube Formation Assay.

Figures 7A, 7B, 7C, 7D:
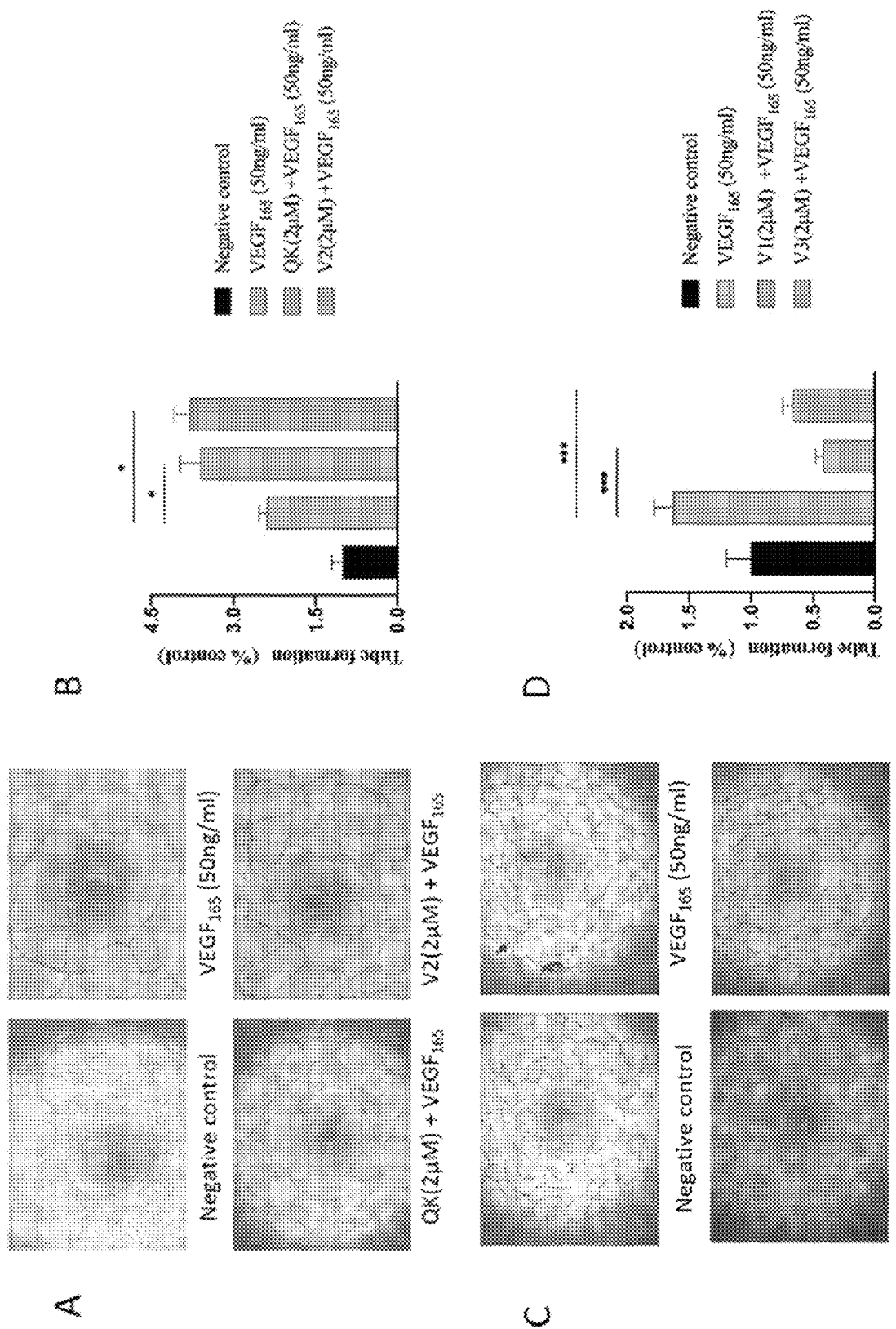
FIGS. 7A-7D. Formation of capillary tube structures of HUVECs following treatment with VEGF mimics in the presence of $VEGF_{165}$ observed after 24 h.

The ultimate effect of angiogenesis is the formation of vasculature that can support healing, survival, and proliferation. Next, the inventors used HUVECs to investigate the effect of the AA peptide sequences on the formation of capillary-like tube structures in vitro in the presence of $VEGF_{165}$. Again, similar to findings from previous assays, the results show strong stimulation of tube formation in response to V2 and QK (FIGS. 7A and 7B) in the presence of VEGF 165, with the stimulatory effects significantly higher as compared to cells treated with only $VEGF_{165}$. In contrast, substantial inhibition of capillary tube formation is observed in cells treated with V1 and V3 in the presence of $VEGF_{165}$ (FIGS. 7C and 7D).

Western Blot Analysis.

Figures 8A, 8B, 8C, 8D, 8E:
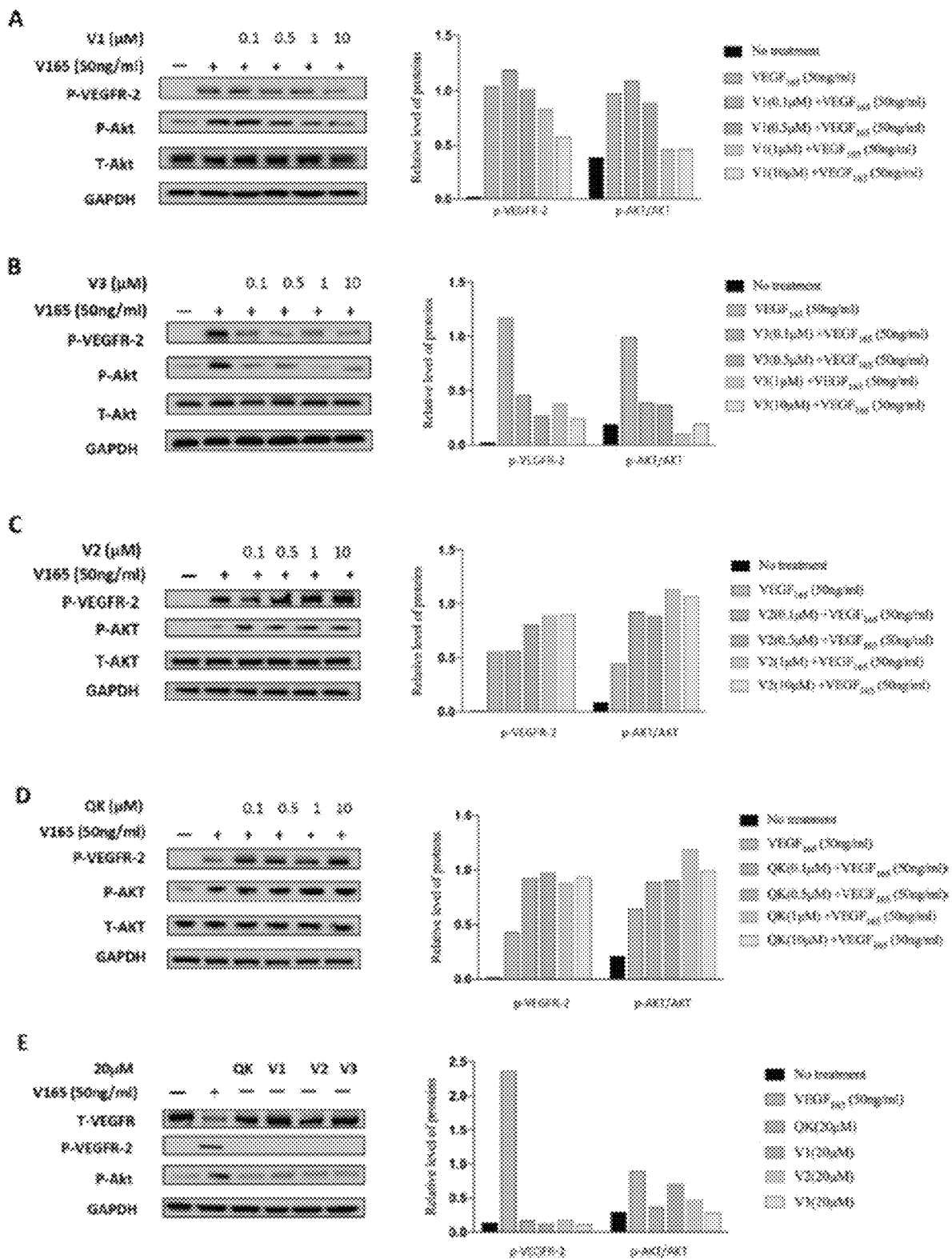
FIGS. 8A-8E. Western blot data on the levels on phosphorylation of VEGFR-2 and Akt in HUVEC lysates following treatment with (FIG. 8A) V1 (0.1, 0.5, 1, 10 μM), (FIG. 8B) V3 (0.1, 0.5, 1, 10 μM), (FIG. 8C) V2 (0.1, 0.5, 1, 10 μM), and (FIG. 8D) QK (0.1, 0.5, 1, 10 μM) and (FIG. 8E) QK, V1, V2, and V3 (20 μM) with or without VEGF 165.

The effect of VEGF-mimicking sequences on VEGF-A-mediated activation of Akt, a key VEGF downstream signal,[68] and VEGFR-2 was then examined by Western blot (FIG. 8). V1 (FIG. 8A) and V3 (FIG. 8B) exhibited dose-dependent inhibition of phosphorylation of VEGFR-2 (P-VEGFR-2) and Akt (P-AKT), with V3 particularly showing potent inhibition even at concentrations as low as 100 nM. On the contrary, V2 (FIG. 8C) and QK (FIG. 8D) increased the levels of phosphorylation of VEGFR-2 and Akt in a dose-dependent manner. However, the activation of the VEGF pathway by V2 and QK is dependent on the presence of VEGF-A (FIG. 8E). In the absence of VEGF-A stimulation, none of the sequences demonstrated activation of VEGFR signaling. The results of the Western blot analysis of VEGFR-2- and VEGF-dependent pathways were congruent with the other in vitro angiogenesis assays, suggesting activation of angiogenesis signaling by V2 is due to its specific binding to the decoy receptor VEGFR-1.

Immunofluorescence Assay.

Figures 9A, 9B, 9C, 9D:
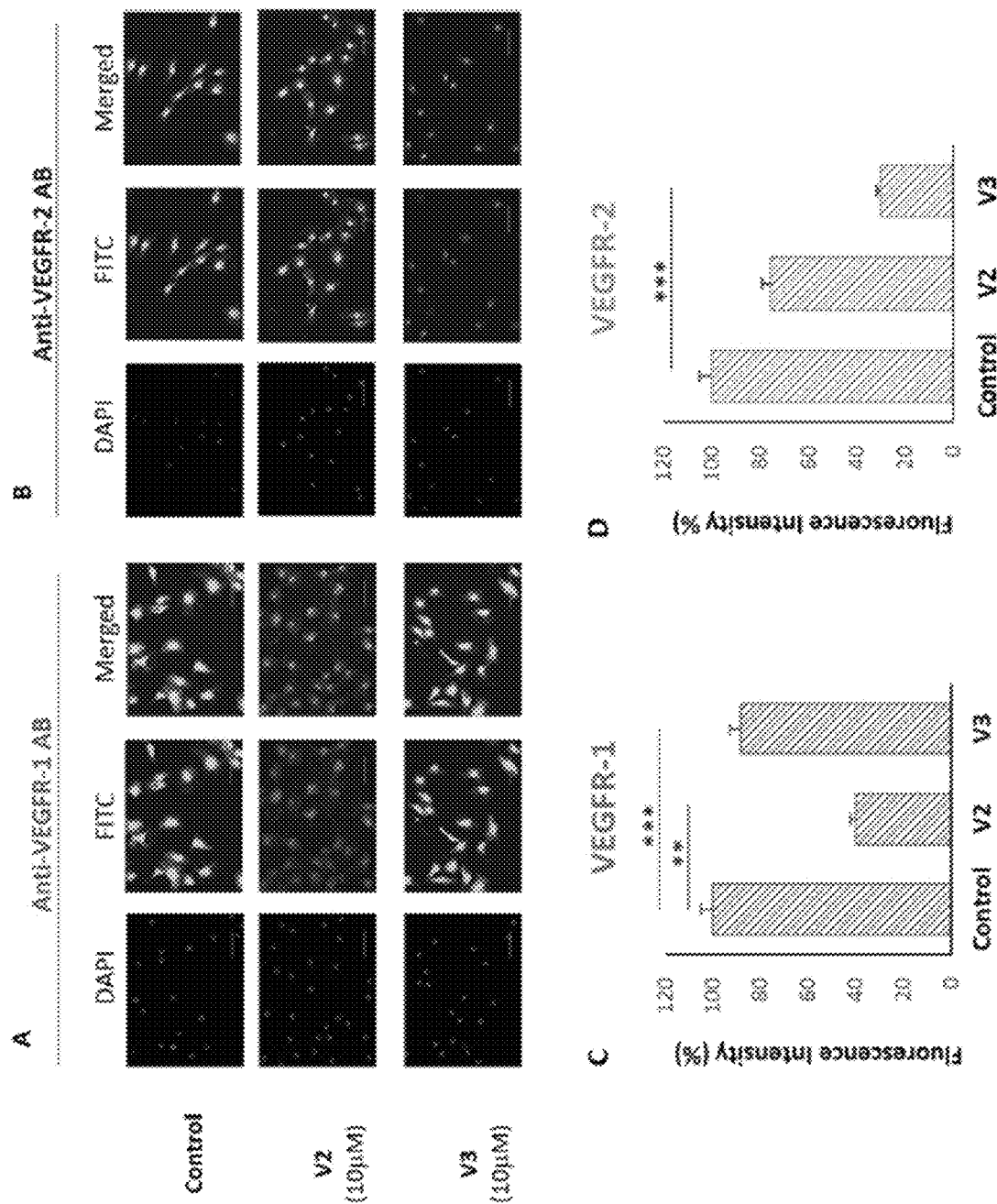
FIGS. 9A-9D. Characterization of binding profiles of V2 and V2 toward VEGFR-1 and VEGFR-2 with immunofluorescence. HUVECs treated with no drug (control), V2, and V3, stained with anti-VEGFR-1 (FIG. 9A) and anti-VEGFR-1 (FIG. 9B) antibody, and detected by FITC-labeled goat anti-rabbit IgG secondary antibody followed by DAPI counterstain.

On the basis of the assays conducted, the inventors speculated that distinct cell signaling and angiogenic response are due to the sequences V2 and V3 binding to different VEGFR subtypes. To further characterize the binding profiles of V2 and V3 to VEGFR-1 and VEGFR-2, immunofluorescence studies were carried out using HUVECs and antibodies specific to each receptor. Cells treated with V2 and V3 (10 μM) were fixed and treated with anti-VEGFR-1 and anti-VEGFR-2 antibodies, followed by FITC-labeled secondary antibody and a DAPI counterstain. Cells treated with V2 had markedly lower fluorescence when incubated with anti-VEGFR-1 antibody (FIGS. 9A and 9C) and a negligible reduction in fluorescence when incubated with anti-VEGFR-2 antibody (FIGS. 9B and 9D). On the other hand, V3-treated cells exhibited a significant reduction of fluorescence when incubated with anti-VEGFR-2 antibody (FIGS. 9B and 9D) but showed almost no effect on intensity of fluorescence in cells incubated with anti-VEGFR-1 antibody (FIGS. 9A and 9C). The findings further demonstrated that V2 binds to VEGFR-1 more tightly than VEGFR-2, whereas V3 binds more specifically to VEGFR-2 over VEGFR-1 on cells.

Discussion

Angiogenesis has profound physiological and structural effects that are implicated in the invasive nature of cancer cells. Being a central process to the metastatic pathway and a hallmark of cancer cells, angiogenesis has garnered tremendous interest in anticancer drug development efforts.[6,69] Besides in cancer, inhibition of amplified angiogenesis also has therapeutic applications in retinopathy. On the other hand, stimulation of angiogenesis has demonstrated therapeutic benefits in ischemic heart disease, organ repair, and wound healing.[4,5] In this regard, the controlled inhibition and activation effects on angiogenic cellular responses is very exciting.

In this study, the inventors used sulfono-γ-AA peptides-based helical foldamers to mimic a critical binding domain on VEGF-A (helix-α1). Recently sulfono-γ-AA peptides have been successfully employed as a new helical framework to design helical domain mimetics and modulate a range of medicinally relevant PPIs, owing to their similarity to mimic α-helix, and reproduce the functionalities on multiple faces of the α-helix. The current design was based on the crystal structure of VEGF-A bound to VEGFR-2. As the most critical residues of VEGF-A, Phe17, Met18, Tyr21, and Tyr25 are involved in binding with VEGFR-2, a few sulfono-γ-AA peptides were designed to reproduce these functionalities using the side chains at 3a, 4b, 5a, and 7a, respectively. For side chains of sulfono-γ-AA peptides not directly involved in the recognition of VEGFR2, the inventors employed a negatively charged Glu side chain and a positively charged Lys side chain at positions 4a and 6a, respectively, in the hope of establishing a salt bridge to stabilize the helical scaffold, as well as enhancing the solubility. Other positions were accommodated with a few common hydrophobic or hydrophilic side chains. The design was very effective, as V1, V2, and V3 all demonstrated good binding affinity toward VEGFR-1 and VEGFR-2. Particularly, V2 showed good selectivity for the binding of VEGFR1, whereas V3 revealed a higher selectivity for VEGFR2. V4, which lacks a critical side chain to mimic F17 and, V5, bearing alanine-like side chains (similar to alanine mutagenesis), did not exhibit any binding activity. CD studies also suggested that the mimic sequences adopt stable left-handed helices as anticipated. The peptide QK, as previously reported, was synthesized and demonstrated significant α-helical folding propensity as well. The results demonstrated that sulfono-γ-AA peptides could be successfully designed to mimic VEGF N-terminal helix-α1.

Among these sulfono-γ-AA peptide foldamers, in vitro angiogenesis assays show that V3 is the most potent inhibitor of angiogenesis; however V2 is a potent activator of angiogenesis. The complete reversal of the effects of these helical mimics to be either pro- or anti-angiogenic is very intriguing because their only difference is the phenyl side chain at the position 3a in V2 vs an indole side chain at the same position in V3. In previous reports, QK and MA peptides, which are derived from the same helix domain of VEGF-A, also demonstrated a counteracting effect in angiogenesis, with differences of only two amino acid residues.'" The contradictory effect was attributed to the different receptor conformation upon binding to these two peptides.34 Based on the results, including binding specificity of V2 and V3 toward VEGFR1 and VEGFR2, respectively, and cell-based studies such as cell migration, Western blotting, and immunofluorescence, the inventors hypothesized an alternative mechanism of angiogenesis modulation. The sulfono-γ-AA peptide-based VEGF-mimicking sequences mimic only a small portion of VEGF-A (helix-α1) and cannot achieve the same overall binding interaction and receptor dimerization as VEGF-A required for receptor activation; thus it is unlikely that the proangiogenic effects observed with V2 and QK are the results of direct binding activation. Western blot assays also show that none of the sequences activate VEGFR-2 and Akt in the absence of VEGF-A (FIG. 8E), indicating that the proangiogenic effects observed are likely due to VEGF-A. It is well known that VEGFR-2 is the main receptor responsible for VEGF-A-mediated angiogenic effects; however, VEGFR-1 is largely believed to be a decoy receptor for circulating VEGF-A, although it may be involved in angiogenesis under certain conditions.[18-21] Moreover, VEGF-A binds more strongly to VEGFR-1, and it was expected that developing a VEGF mimic targeting VEGFR-2 selectively would require some modifications. Based on the binding affinity studies, which reveal a higher affinity of V2 toward VEGFR-1, the "decoy" receptor, and a selective binding of V3 toward VEGFR-2, the main angiogenic receptor, the inventors hypothesize that the pro-angiogenic effect of V2 is the result of selective/higher binding of V2 to VEGFR-1, which would increase the levels of VEGF-A available to bind and activate the main angiogenic receptor, VEGFR-2. This is indeed consistent with previous findings, in which protein ligands specific for VEGFR-1 led to activation of VEGFR-2-mediated signaling.[67]

Figure 15:
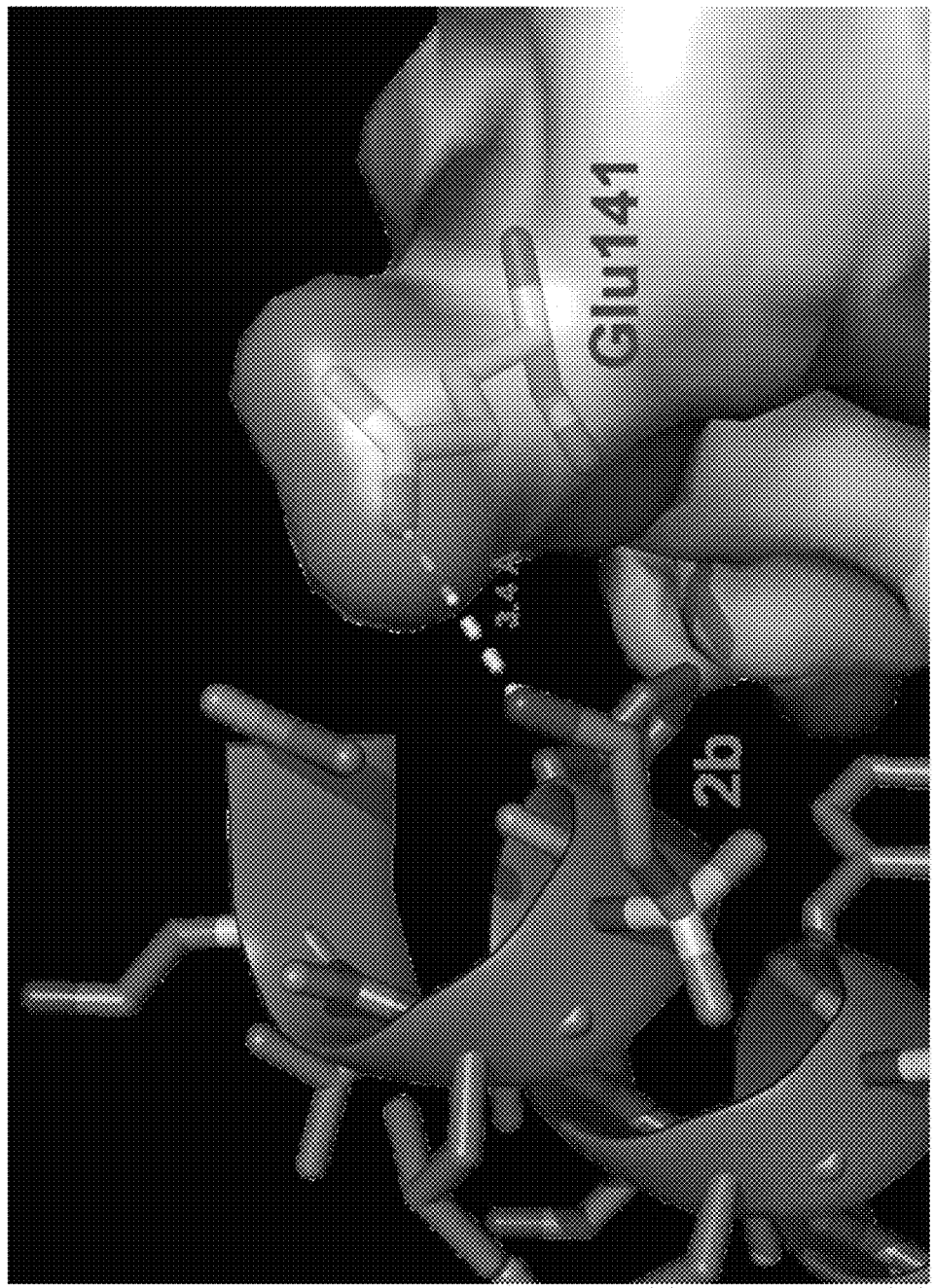
FIG. 15. Salt bridge formed between the side chain 2a of V2 and Glu141 of VEGFR1.

In order to gain insight into the binding selectivity of V2 and V3, the inventors next conducted computational modeling. Crystal structures of VEGF-A bound to VEGFR-1 (PDB: 1FLT) and VEGFR-2 (PDB: 3V2A) exhibit some subtle but probably crucial differences in the binding surfaces of the receptors; notably the hydrophobic pocket interacting with VEGF Phe17 is much smaller in VEGFR-1 and would be less accommodating to larger groups (FIGS. 10B-D). The indole group replacing the phenyl group on V3 would be presumably too big for this pocket; however this pocket is much larger in VEGFR-2, and this larger indole group of V3 would be expected to produce a more favorable interaction (FIG. 10A). This might explain the possible selectivity of V2 and V3 to VEGFR-1 and VEGFR-2 respectively. The modeling could also rationalize the different binding affinities of V1 and V2, which bear same critical binding groups, but V1 exhibited a much weaker binding capability toward VEGFR1. As shown in FIG. 10C, sulfono-γ-AA peptides form longer helices than the helical domain of VEGF-A. When binding to VEGFR1, the N-terminus of the helix has to tilt away from the binding site slightly to avoid direct clash with the top edge of the binding site (FIG. 10D), which may weaken the interaction of V1 with VEGFR1. In contrast, the positively charged side chain at position 2b of V2 could form an electrostatic interaction with the negatively charged Glu141 of VEGFR1 at the edge, which instead could enhance the binding (FIG. 15). However, the binding site on VEGFR2 is not as protruding as the one on VEGFR1 (FIG. 10A), and as a result, the side chains on 2b are much less relevant. Next, immunofluorescence studies further verified the selective binding activities at the cellular level. In this study V2 demonstrated a much stronger inhibition of anti-VEGFR-1 antibody than anti-VEGFR-2 antibody, whereas V3 had near complete selectivity toward inhibition of anti-VEGFR-2 antibody, without significant inhibition of anti-VEGFR-1 antibody. This investigation further supports that the selectivity of V2 and V3 for either VEGFR-1 or VEGFR-2 leads to pro- and antiangiogenic effects, respectively. A healthy level of angiogenesis is maintained through a set of pro-angiogenic and antiangiogenic factors, a process termed as angiogenic switch.[70] Having control of this process gives a tremendous opportunity to intervene in several disease conditions that are caused due to imbalances in angiogenesis (FIG. 10E). In this regard, the pro-angiogenic and anti-angiogenic activities of V2 and V3, respectively, offer a dynamic control of the angiogenic switch.

Figure 11:
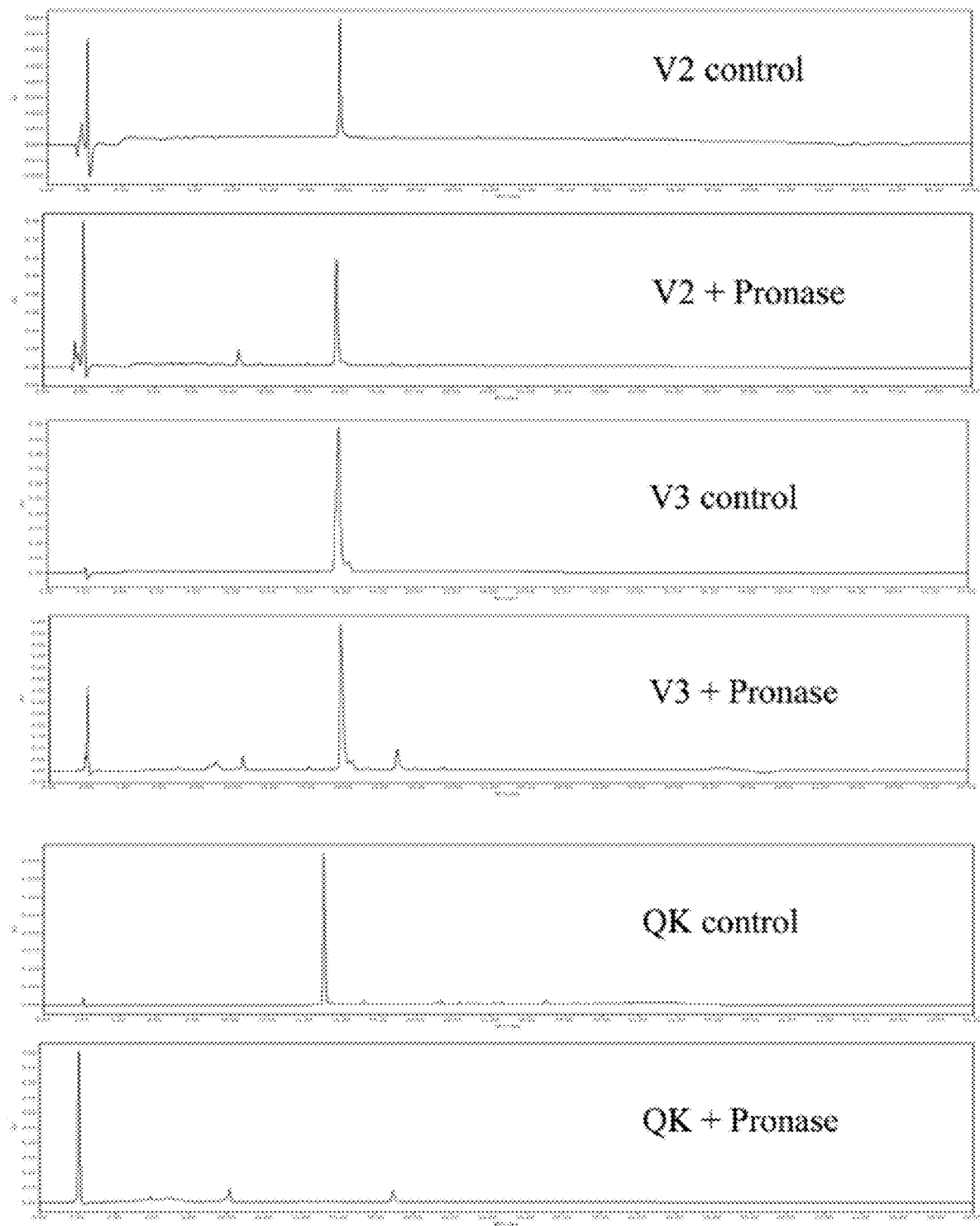
FIG. 11. Stability studies of VEGF-A mimics. HPLC traces of indicated control sequences and sequences incubated in Pronase for 24 h.
Figure 13:
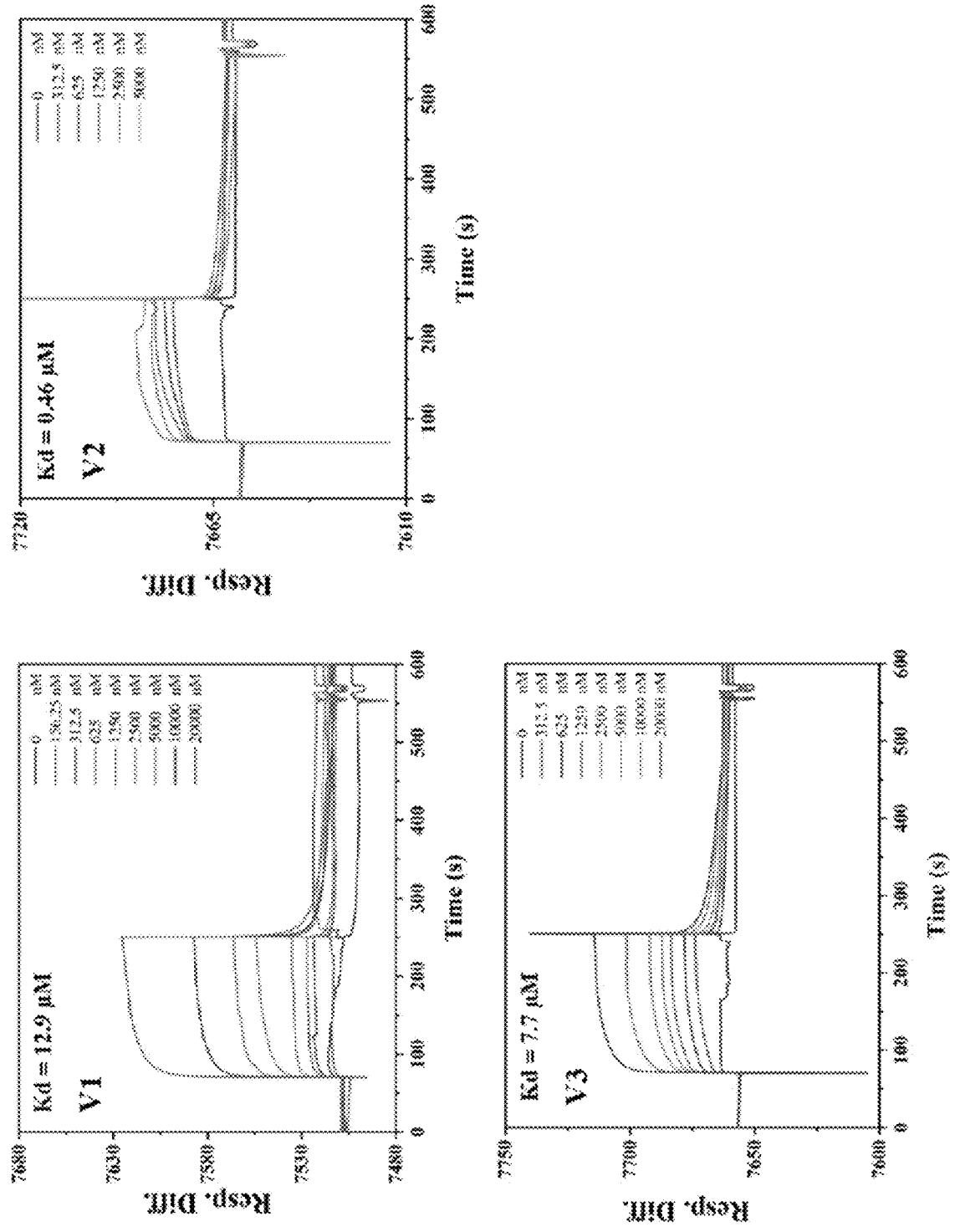
FIG. 13. Binding kinetics of V1, V2 and V3 with VEGFR-1 as determined with SPR.
Figure 14:
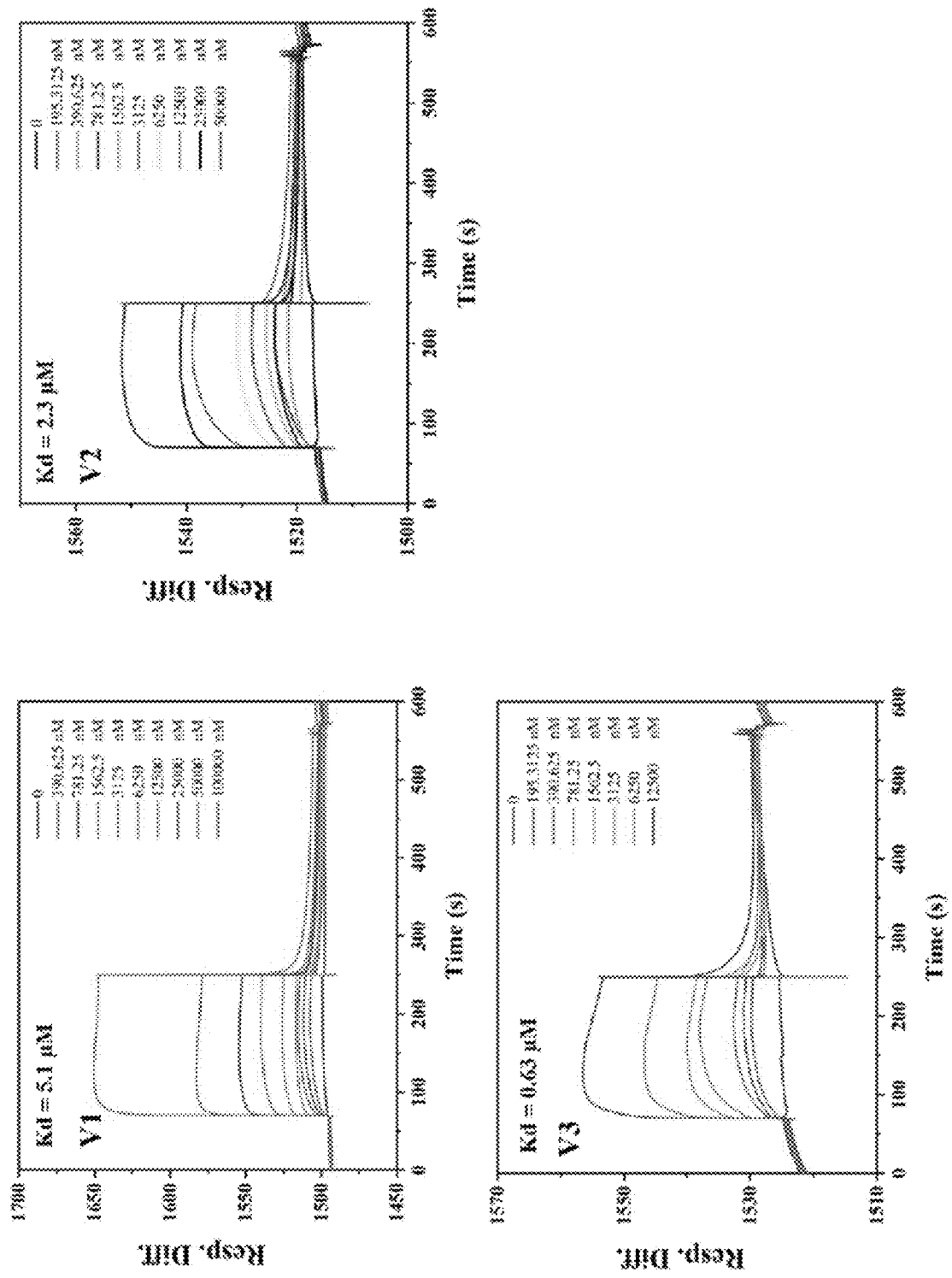
FIG. 14. Binding kinetics of V1, V2 and V3 with VEGFR-2 as determined with SPR.

One of the major bottlenecks in the development of peptide-based molecular probes or drug candidates is their inherent susceptibility to degradation with proteolytic enzymes. Next, the inventors assessed the stability of the lead mimics V2 and V3 and the control model peptide QK in Pronase, a broad-specificity mixture of proteases extracted from *Streptomyces griseus*. The sequences were incubated in Pronase for 24 h and analyzed with HPLC (FIG. 11). The sulfono-γ-AA peptide mimics (V2 and V3) were remarkably stable and did not exhibit any noticeable degradation. However, QK, bearing natural amino acid residues, was completely degraded.

CONCLUSION

The inventors have successfully designed unprecedented unnatural helical foldameric mimetics of a critical binding domain of VEGF-A (helix-α1). Cell-based angiogenesis assays show that these mimicking sequences could be either pro- or anti-angiogenic and upregulate or downregulate angiogenesis, thus effectively modulating the angiogenic switch. The inventors believe the distinct angiogenesis signaling is due to the specific binding of helical mimetics toward VEGFR-1 or VEGFR-2, respectively. Targeting VEGFR-1 specifically (V2) is expected to free more VEGF from VEGFR-1 binding and shift the dial for VEGFR-2 interaction, leading to amplified angiogenesis. Specific binding to VEGFR-2 (V3), on the contrary, would be capable of inhibiting VEGF-A/VEGFR-2 PPI and therefore block the angiogenesis signaling pathway. Therefore, V2 and V3 represent promising unnatural peptidomimetics for the intervention of disease conditions arising due to angiogenic imbalances and could be used as a tool for chemical biology. Moreover, the study further manifested the versatility of sulfono-γ-AA peptides to mimic protein helical domains. This is a remarkable feat for helical sulfono-γ-AA peptides considering the significance of helices in PPIs, where 62% of multiprotein complexes in the Protein Data Bank involve a helix at the interface.[71]

References for Example 1

(1). Sherwood L M; Parris E E; Folkman J Tumor angiogenesis: therapeutic implications. N. Engl. J. Med. 1971, 285 (21), 1182-6. [PubMed: 4938153]

(2). Shubik P Vascularization of tumors: a review. J. Cancer Res. Clin. Oncol. 1982, 103 (3), 211-26. [PubMed: 6181069]

(3). Folkman J Role of angiogenesis in tumor growth and metastasis. Semin. Oncol. 2002, 29, 15-18.

(4). Gupta K; Zhang J Angiogenesis: a curse or cure? Postgrad. Med. J. 2005, 81 (954), 236. [PubMed: 15811887]

(5). Carmeliet P; Jain R K Angiogenesis in cancer and other diseases. Nature 2000, 407 (6801), 249-57. [PubMed: 11001068]

(6). Hanahan D; Weinberg R A Hallmarks of cancer: the next generation. Cell 2011, 144 (5), 646-74. [PubMed: 21376230]

(7). Klagsbrun M; Moses M A Molecular angiogenesis. Chem. Biol. 1999, 6 (8), R217-R224. [PubMed: 10421764]

(8). Ferrara N; Davis-Smyth T The biology of vascular endothelial growth factor. Endocr. Rev. 1997, 18 (1), 4-25. [PubMed: 9034784]

(9). Leung D W; Cachianes G; Kuang W J; Goeddel D V; Ferrara N Vascular endothelial growth factor is a secreted angiogenic mitogen. Science 1989, 246 (4935), 1306-9. [PubMed: 2479986]

(10). Karamysheva A F Mechanisms of angiogenesis. Biochemistry (Moscow) 2008, 73 (7), 751. [PubMed: 18707583]

(11). Ferrara N Vascular endothelial growth factor: molecular and biological aspects. Curr. Top. Microbiol. Immunol. 1999, 237, 1-30. [PubMed: 9893343]

(12). Dvorak H F; Brown L F; Detmar M; Dvorak A M Vascular permeability factor/vascular endothelial growth factor, microvascular hyperpermeability, and angiogenesis. Am. J. Pathol. 1995, 146 (5), 1029-1039. [PubMed: 7538264]

(13). Neufeld G; Tessler S; Gitay-Goren H; Cohen T; Levi B Z Vascular endothelial growth factor and its receptors. Prog. Growth Factor Res. 1994, 5 (1), 89-97. [PubMed: 7515293]

(14). Byrne A M; Bouchier-Hayes D J; Harmey J H Angiogenic and cell survival functions of vascular endothelial growth factor (VEGF). J. Cell Mol. Med. 2005, 9 (4), 777-94. [PubMed: 16364190]

(15). Dias S; Shmelkov S V; Lam G; Rafii S VEGF(165) promotes survival of leukemic cells by Hsp90-mediated induction of Bcl-2 expression and apoptosis inhibition. Blood 2002, 99 (7), 2532-40. [PubMed: 11895790]

(16). Lashkari K; Rahimi N; Dayanir V Receptor Chimeras Indicate That the Vascular Endothelial Growth Factor Receptor-1 (VEGFR-1) Modulates Mitogenic Activity of VEGFR-2 in Endothelial Cells*. J. Biol. Chem. 2000, 275 (22), 16986-16992. [PubMed: 10747927]

(17). Felix J; Savvides S N Mechanisms of immunomodulation by mammalian and viral decoy receptors: insights from structures. Nat. Rev. Immunol. 2017, 17 (2), 112. [PubMed: 28028310]

(18). Shibuya M Vascular endothelial growth factor receptor-1 (VEGFR-1/Flt-1): a dual regulator for angiogenesis. Angiogenesis 2006, 9 (4), 225-30. [PubMed: 17109193]

(19). Ferrara N; Gerber H-P; LeCouter J The biology of VEGF and its receptors. Nat. Med. 2003, 9 (6), 669-676. [PubMed: 12778165]

(20). Hiratsuka S; Minowa O; Kuno J; Noda T; Shibuya M Flt-1 lacking the tyrosine kinase domain is sufficient for normal development and angiogenesis in mice. Proc. Natl. Acad. Sci. U.S.A. 1998, 95 (16), 9349-54. [PubMed: 9689083]

(21). Ho V C; Fong G H Vasculogenesis and Angiogenesis in VEGF Receptor-1 Deficient Mice. Methods Mol. Biol. 2015, 1332, 161-76. [PubMed: 26285753]

(22). Brem H; Folkman J Inhibition of tumor angiogenesis mediated by cartilage. Journal of Experimental Medicine 1975, 141 (2), 427.

(23). Langer R; Conn H; Vacanti J; Haudenschild C; Folkman J Control of tumor growth in animals by infusion of an angiogenesis inhibitor. Proc. Natl. Acad. Sci. U.S.A. 1980, 77 (7), 4331-5. [PubMed: 6159628]

(24). Gimbrone M A Jr.; Cotran R S; Leapman S B; Folkman J Tumor growth and neovascularization: an experimental model using the rabbit cornea. J. Natl. Cancer Inst. 1974, 52 (2), 413-27. [PubMed: 4816003]

(25). Gimbrone M A Jr.; Leapman S B; Cotran R S; Folkman J Tumor dormancy in vivo by prevention of neovascularization. J. Exp. Med. 1972, 136 (2), 261-76. [PubMed: 5043412]

(26). Folkman J; Hochberg M Self-regulation of growth in three dimensions. J. Exp. Med. 1973, 138 (4), 745-53. [PubMed: 4744009]

(27). Cohen M H; Gootenberg J; Keegan P; Pazdur R FDA drug approval summary: bevacizumab plus FOLFOX4 as second-line treatment of colorectal cancer. Oncologist 2007, 12 (3), 356-61. [PubMed: 17405901]

(28). Cook K M; Figg W D Angiogenesis Inhibitors: Current Strategies and Future Prospects. CA Cancer J. Clin. 2010, 60 (4), 222-243. [PubMed: 20554717]

(29). Eskens FALM Angiogenesis inhibitors in clinical development; where are we now and where are we going? Br. J. Cancer 2004, 90, 1. [PubMed: 14710197]

(30). Ronca R; Benkheil M; Mitola S; Struyf S; Liekens S Tumor angiogenesis revisited: Regulators and clinical implications. Med. Res. Rev. 2017, 37 (6), 1231-1274. [PubMed: 28643862]

(31). Brozzo M S; Bjelić S; Kisko K; Schleier T; Leppänen V M; Alitalo K; Winkler F K; Ballmer-Hofer K Thermodynamic and structural description of allosterically regulated VEGFR-2 dimerization. Blood 2012, 119 (7), 1781. [PubMed: 22207738]

(32). Muller Y A; Li B; Christinger H W; Wells J A; Cunningham B C; De Vos A M Vascular Endothelial Growth Factor: Crystal Structure and Functional Mapping of the Kinase Domain Receptor Binding Site. Proc. Natl. Acad. Sci. U.S.A. 1997, 94 (14), 7192-7197. [PubMed: 9207067]

(33). D'Andrea L D; Iaccarino G; Fattorusso R; Sorriento D; Carannante C; Capasso D; Trimarco B; Pedone C Targeting angiogenesis: structural characterization and biological properties of a de novo engineered VEGF mimicking peptide. Proc. Natl. Acad. Sci. U.S.A. 2005, 102 (40), 14215-20. [PubMed: 16186493]

(34). Basile A; Del Gatto A; Diana D; Di Stasi R; Falco A; Festa M; Rosati A; Barbieri A; Franco R; Arra C Characterization of a designed vascular endothelial growth factor receptor antagonist helical peptide with antiangiogenic activity in vivo. J. Med. Chem. 2011, 54 (5), 1391-1400. [PubMed: 21280635]

(35). Fosgerau K; Hoffmann T Peptide therapeutics: current status and future directions. Drug Dis. Today 2015, 20 (1), 122-128.

(36). Ivanov A A; Khuri F R; Fu H Targeting protein-protein interactions as an anticancer strategy. Trends Pharmacol. Sci. 2013, 34 (7), 393-400. [PubMed: 23725674]

(37). Ryan D P; Matthews J M Protein-protein interactions in human disease. Curr. Opin. Struc. Biol. 2005, 15 (4), 441-446.

(38). Schaefer M H; Lopes T J; Mah N; Shoemaker J E; Matsuoka Y; Fontaine J F; Louis-Jeune C; Eisfeld A J; Neumann G; Perez-Iratxeta C; Kawaoka Y; Kitano H; Andrade-Navarro M A Adding protein context to the human protein-protein interaction network to reveal meaningful interactions. PLoS Comput. Biol. 2013, 9 (1), No. e1002860.

(39). Akram O N; DeGraff D J; Sheehan J H; Tilley W D; Matusik R J; Ahn J M; Raj G V Tailoring peptidomimetics for targeting protein-protein interactions. Mol. Cancer Res. 2014, 12 (7), 967-78. [PubMed: 24642350]

(40). Pelay-Gimeno M; Glas A; Koch O; Grossmann T N Structure-Based Design of Inhibitors of Protein-Protein Interactions: Mimicking Peptide Binding Epitopes. Angew. Chem., Int. Ed. Engl. 2015, 54 (31), 8896-927. [PubMed: 26119925]

(41). Lee K J; Bang G; Kim Y W; Shin M H; Lim H-S Design and synthesis of a DNA-encoded combinatorial library of bicyclic peptoids. Biorg. Med. Chem. 2021, 48, 116423.

(42). Rzeigui M; Traikia M; Jouffret L; Kriznik A; Khiari J; Roy O; Taillefumier C Strengthening Peptoid Helicity through Sequence Site-Specific Positioning of Amide cis-Inducing NtBu Monomers. J. Org. Chem. 2020, 85 (4), 2190-2201. [PubMed: 31873018]

(43). Arvidsson P I; Frackenpohl J; Ryder N S; Liechty B; Petersen F; Zimmermann H; Camenisch G P; Woessner R; Seebach D On the antimicrobial and hemolytic activities of amphiphilic beta-peptides. ChemBioChem. 2001, 2 (10), 771-3. [PubMed: 11948860]

(44). Cheng R P; Gellman S H; DeGrado W F beta-Peptides: from structure to function. Chem. Rev. 2001, 101 (10), 3219-32. [PubMed: 11710070]

(45). Checco J W; Kreitler D F; Thomas N C; Belair D G; Rettko N J; Murphy W L; Forest K T; Gellman S H Targeting diverse protein-protein interaction interfaces with α/β-peptides derived from the Z-domain scaffold. Proc. Natl. Acad. Sci. U.S.A. 2015, 112 (15), 4552-4557. [PubMed: 25825775]

(46). Checco J W; Gellman S H Iterative non-proteinogenic residue incorporation yields α/β-peptides with a helix-loop-helix tertiary structure and high affinity for VEGF. Chembiochem 2017, 18 (3), 291. [PubMed: 27897370]

(47). Gibadullin R; Randall C J; Sidney J; Sette A; Gellman S H Backbone Modifications of HLA-A2-Restricted Antigens Induce Diverse Binding and T Cell Activation Outcomes. J. Am. Chem. Soc. 2021, 143 (17), 6470-6481. [PubMed: 33881854]

(48). Outlaw V K; Cheloha R W; Jurgens E M; Bovier F T; Zhu Y; Kreitler D F; Harder O; Niewiesk S; Porotto M; Gellman S H; Moscona A Engineering Protease-Resistant Peptides to Inhibit Human Parainfluenza Viral Respiratory Infection. J. Am. Chem. Soc. 2021, 143 (15), 5958-5966. [PubMed: 33825470]

(49). Gante J Azapeptides. Synthesis 1989, 21 (06), 405-413.

(50). Sabatino D; Proulx C; Pohankova P; Ong H; Lubell W D Structure-Activity Relationships of GHRP-6 Azapeptide Ligands of the CD36 Scavenger Receptor by Solid-Phase Submonomer Azapeptide Synthesis. J. Am. Chem. Soc. 2011, 133 (32), 12493-12506. [PubMed: 21692501]

(51). Yoo S H; Li B; Dolain C; Pasco M; Guichard G, Chapter Three—Urea based foldamers. In Methods Enzymol., Petersson E J, Ed. Academic Press: 2021; Vol. 656, pp 59-92. [PubMed: 34325800]

(52). Cussol L; Mauran-Ambrosino L; Buratto J; Belorusova A Y; Neuville M; Osz J; Fribourg S; Fremaux J; Dolain C; Goudreau S R; Rochel N; Guichard G Structural Basis for α-Helix Mimicry and Inhibition of Protein-Protein Interactions with Oligourea Foldamers. Angew. Chem., Int. Ed. 2021, 60 (5), 2296-2303.

(53). Maity D; Hamilton A D The helical supramolecular assembly of oligopyridylamide foldamers in aqueous media can be guided by adenosine diphosphates. Chem. Commun. 2021, 57 (73), 9192-9195.

(54). Fletcher J M; Homer K A; Bartlett G J; Rhys G G; Wilson A J; Woolfson D N De novo coiled-coil peptides as scaffolds for disrupting protein-protein interactions. Chem. Sci. 2018, 9 (39), 7656-7665. [PubMed: 30393526]

(55). Jedhe G S; Arora P S In Methods in Enzymology; Petersson E J, Ed.; Academic Press: 2021; Vol. 656, Chapter 1, pp 1-25. [PubMed: 34325784]

(56). Bolarinwa O; Nimmagadda A; Su M; Cai J Structure and Function of AApeptides. Biochemistry 2017, 56 (3), 445-457. [PubMed: 28029249]

(57). Shi Y; Teng P; Sang P; She F; Wei L; Cai J γ-AApeptides: Design, Structure, and Applications. Acc. Chem. Res. 2016, 49 (3), 428-441. [PubMed: 26900964]

(58). Sang P; Shi Y; Huang B; Xue S; Odom T; Cai J Sulfono-γ-AApeptides as Helical Mimetics: Crystal Structures and Applications. Acc. Chem. Res. 2020, 53 (10), 2425-2442. [PubMed: 32940995]

(59). Wu H; Qiao Q; Hu Y; Teng P; Gao W; Zuo X; Wojtas L; Larsen R W; Ma S; Cai J Sulfono-γ-AApeptides as a New Class of Nonnatural Helical Foldamer. Chem.—Eur. J 2015, 21 (6), 2501-2507. [PubMed: 25504756]

(60). She F; Teng P; Peguero-Tejada A; Wang M; Ma N; Odom T; Zhou M; Gjonaj E; Wojtas L; van der Vaart A; Cai J De Novo Left-Handed Synthetic Peptidomimetic Foldamers. Angew. Chem., Int. Ed. 2018, 57 (31), 9916-9920.

(61). Sang P; Shi Y; Lu J; Chen L; Yang L; Borcherds W; Abdulkadir S; Li Q; Daughdrill G; Chen J; Cai J α-Helix-Mimicking Sulfono-γ-AApeptide Inhibitors for p53-MDM2/MDMX Protein-Protein Interactions. J. Med. Chem. 2020, 63, 975. [PubMed: 31971801]

(62). Sang P; Zhou Z; Shi Y; Lee C; Amso Z; Huang D; Odom T; Nguyen-Tran V; Shen W; Cai J The Activity of Sulfono-γ-AApeptide Helical Foldamers That Mimic GLP-1. Sci. Adv 2020, 6, No. eaaz4988.

(63). Sang P; Zhang M; Shi Y; Li C; Abdulkadir S; Li Q; Ji H; Cai J Inhibition of β-catenin/B Cell Lymphoma 9 Protein-protein Interaction using α-helix-mimicking Sulfono-γ-AApeptide Inhibitors. Proc. Natl. Acad. Sci. U.S.A. 2019, 116, 10757. [PubMed: 31088961]

(64). Shi Y; Sang P; Lu J; Higbee P; Chen L; Yang L; Odom T; Daughdrill G; Chen J; Cai J Rational Design of Right-Handed Heterogeneous Peptidomimetics as Inhibitors of Protein-Protein Interactions. J. Med. Chem. 2020, 63 (21), 13187-13196. [PubMed: 33140956]

(65). Muller Y A; Christinger H W; Keyt B A; de Vos A M The crystal structure of vascular endothelial growth factor (VEGF) refined to 1.93 A resolution: multiple copy flexibility and receptor binding. Structure 1997, 5 (10), 1325-1338. [PubMed: 9351807]

(66). Lohela M; Bry M; Tammela T; Alitalo K VEGFs and receptors involved in angiogenesis versus lymphangiogenesis. Curr. Opin. Cell Biol. 2009, 21 (2), 154-165. [PubMed: 19230644]

(67). Anisimov A; Leppänen V-M; Tvorogov D; Zarkada G; Jeltsch M; Holopainen T; Kaijalainen S; Alitalo K The basis for the distinct biological activities of vascular endothelial growth factor receptor-1 ligands. Sci. Signal 2013, 6 (282), No. ra52-ra52.

(68). Dellinger M T; Brekken R A Phosphorylation of Akt and ERK1/2 Is Required for VEGF-A/VEGFR2-Induced Proliferation and Migration of Lymphatic Endothelium. PLoS One 2011, 6 (12), No. e28947.

(69). Zetter P B Angiogenesis and Tumor Metastasis. Annu. Rev. Med 1998, 49 (1), 407-424. [PubMed: 9509272]

(70). Bergers G; Benjamin L E Tumorigenesis and the angiogenic switch. Nat. Rev. Cancer 2003, 3 (6), 401-410. [PubMed: 12778130]

(71). Bullock B N; Jochim A L; Arora P S Assessing Helical Protein Interfaces for Inhibitor Design. J. Am. Chem. Soc. 2011, 133 (36), 14220-14223. [PubMed: 21846146]

Example 2

1. Synthesis of Sulfono-γ-AA Peptide Building Blocks 1.1 General Information

All chemicals and solvents were purchased from Sigma-Aldrich, Fisher Scientific or Oakwood and used as supplied. Fmoc protected amino acids were purchased from Chem-Impex International. Varian Unity Inova 400 Mhz NMR spectrometer was used to acquire $^1$H-NMR at 400 MHz and $^{13}$C-NMR at 100 MHz using TMS as the internal standard. Mass analysis was conducted on an Agilent LC-MS SQ G1956A mass spectrometer.

1.2 Synthesis

Figure 16:
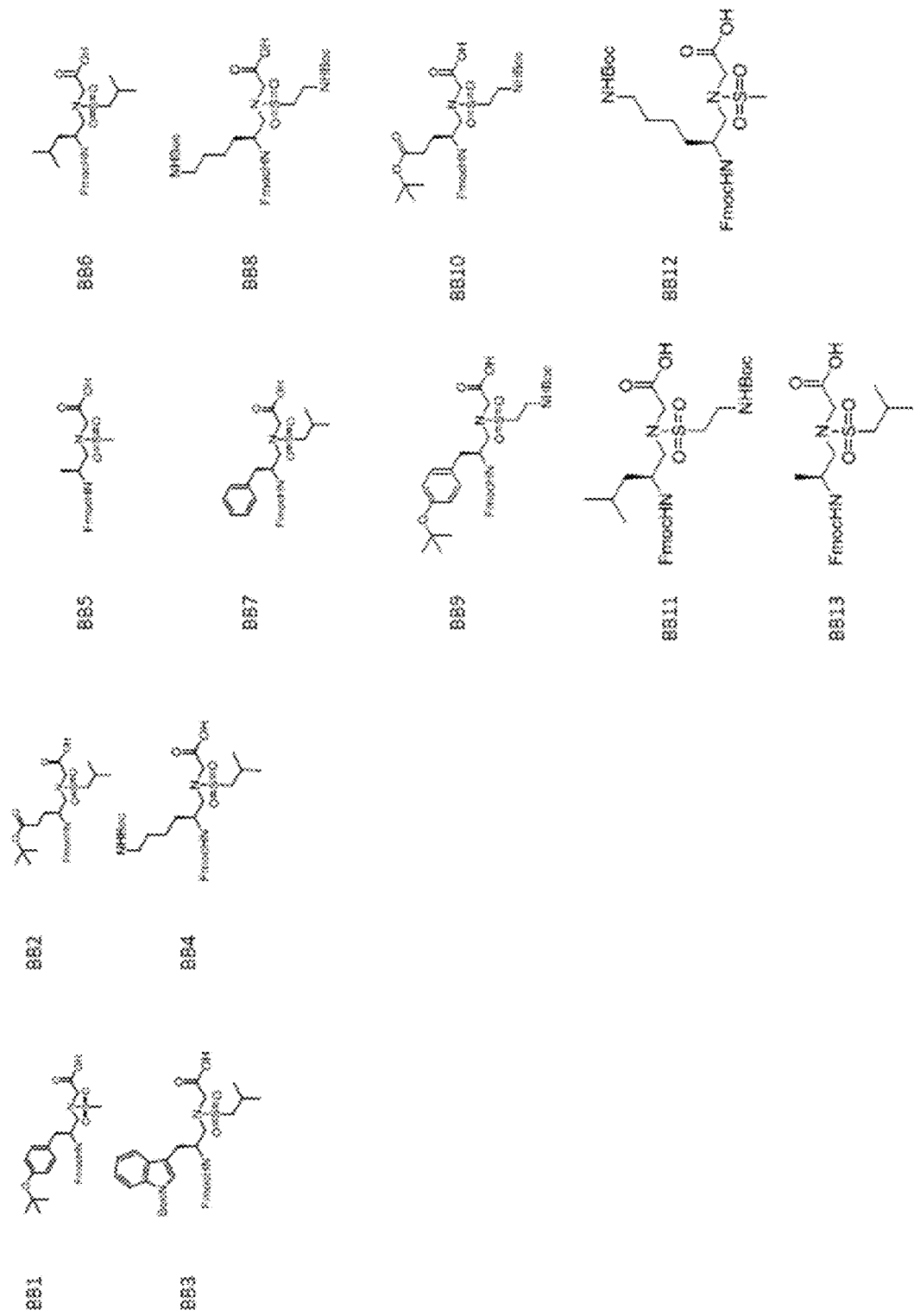
FIG. 16. Structure of sulfono-γ-AA peptide building blocks.
Figure 17:
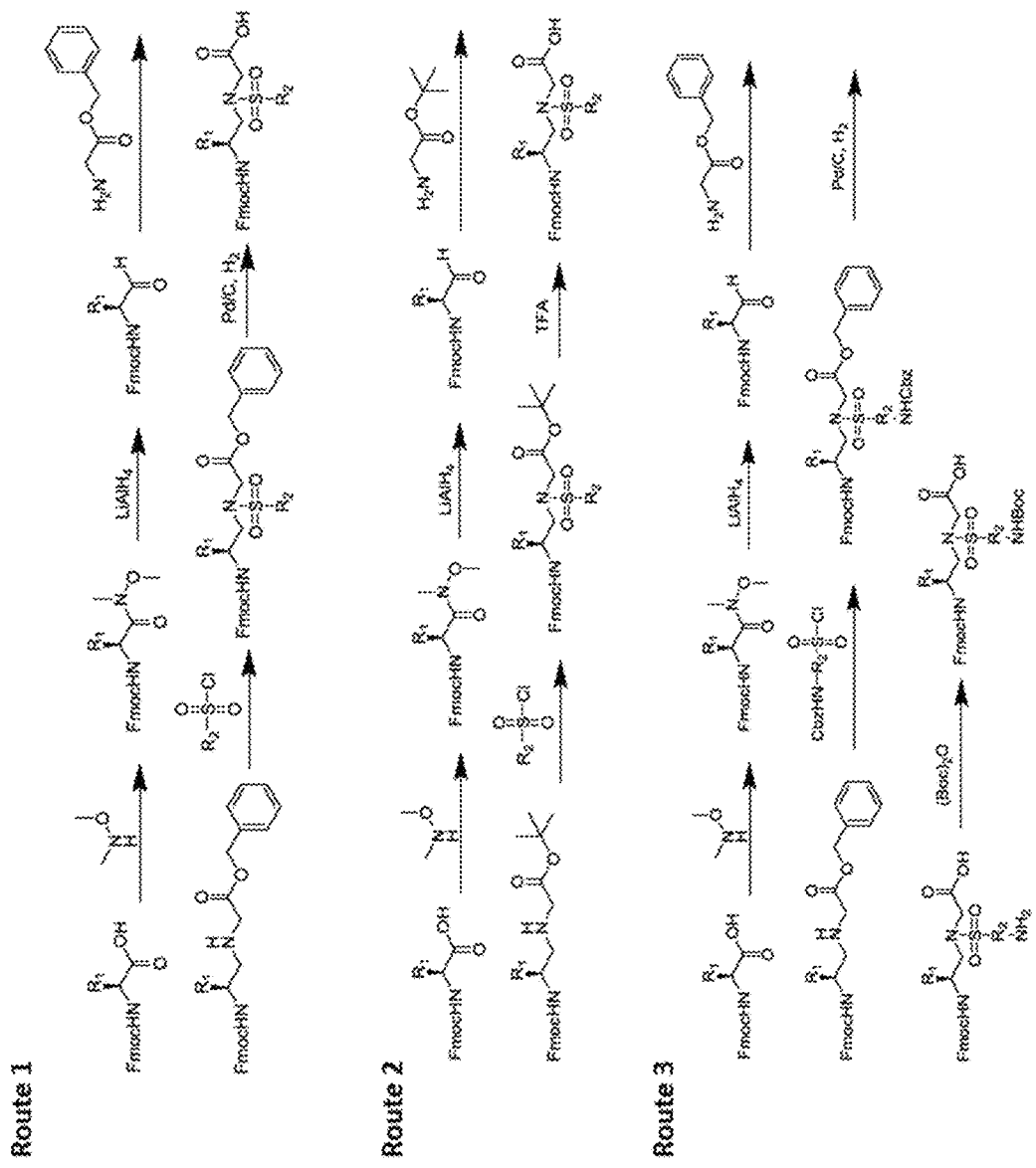
FIG. 17. General routes of synthesis of sulfono-γ-AA peptide building blocks.

The sulfono-γ-AA peptide building blocks (FIG. 16) were synthesized from Fmoc protected amino acids based on previously reported method.[1-6] Depending on the protecting groups utilized, the building blocks were synthesized via one of the three routes outlined in FIG. 17 (Scheme Si). Building blocks BB1-5 and BB12 were synthesized with route 1, BB6-8 and BB13 were synthesize using route 2, and BB9-11 were synthesized using route 3.

1.3 Characterization of Sulfono-γ-A Peptide Building Blocks

BB1: (S)—N-(2-((((9H-fluoren-9-yl)methoxy)carbonyl) amino)-3-(4-(tert-butoxy)phenyl)propyl)-N-(methylsulfonyl)glycine. $^1$H NMR (400 MHz, DMSO) δ 7.89 (d, J=7.5 Hz, 2H), 7.69 (d, J=3.4 Hz, 1H), 7.61 (t, J=40.5 Hz, 1H), 7.37 (dt, J=34.4, 7.4 Hz, 2H), 7.21 (d, J=9.1 Hz, 1H), 4.33 (dd, J=6.7, 3.2 Hz, 2H), 4.21 (t, J=6.7 Hz, 1H), 3.96 (s, 2H), 3.64 (dd, J=10.4, 6.7 Hz, 1H), 3.37 (dd, J=13.9, 6.9 Hz, 1H), 3.26 (dd, J=14.4, 5.6 Hz, 1H), 3.13 (dd, J=14.4, 8.4 Hz, 1H), 2.94 (s, 3H), 2.54-2.45 (m, 1H), 2.25-2.07 (m, 2H), 1.72 (dd, J=7.5, 3.6 Hz, 1H), 1.38 (s, 9H). $^{13}$C NMR (101 MHz, DMSO) δ 171.08, 155.87, 153.25, 144.00, 140.83, 133.39, 129.77, 127.73, 127.15, 123.53, 120.21, 115.02, 77.60, 65.47, 51.42, 48.62, 46.75, 37.09, 28.52, 27.13. HRMS (ESI) (M+H)$^{+1}$ Calc. for $C_{31}H_{36}N_2O_7S$: 580.2243, found: 581.2312 (M+H)$^+$, 1161.4545 (2M+H).

BB7: (S)—N-(2-((((9H-fluoren-9-yl)methoxy)carbonyl) amino)-3-phenylpropyl)-N-(isobutyl sulfonyl) glycine. $^1$H NMR (600 MHz, DMSO) δ 7.87 (d, J=7.5 Hz, 1H), 7.62 (d, J=7.5 Hz, 1H), 7.41 (td, J=7.3, 3.6 Hz, 1H), 7.35 (dd, J=24.2, 8.3 Hz, 1H), 7.31-7.22 (m, 3H), 7.18-7.14 (m, 1H), 4.22 (dd, J=10.0, 6.9 Hz, 1H), 4.14 (dt, J=17.8, 7.0 Hz, 1H), 4.04 (dd, J=56.1, 18.6 Hz, 1H), 3.93-3.88 (m, 1H), 3.34 (ddd, J=22.6, 14.3, 6.9 Hz, 1H), 3.03-2.96 (m, 1H), 2.90 (dd, J=13.6, 3.9 Hz, 1H), 2.62 (dd, J=13.5, 10.0 Hz, 1H), 2.14-2.06 (m, 1H), 0.98 (dd, J=9.5, 6.8 Hz, 3H). $^{13}$C NMR (151 MHz, DMSO) δ 171.10, 158.67, 158.41, 155.82, 143.93, 143.86, 140.79, 138.77, 129.27, 128.15, 127.70, 127.13, 126.12, 125.35, 125.29, 125.01, 120.18, 116.17, 114.26, 65.43, 58.92, 52.44, 51.70, 51.44, 51.24, 48.43, 46.77, 37.63, 24.34, 22.27, 22.25. HRMS (ESI) (M+H)$^{+1}$ Calc. for $C_{30}H_{34}N_2O_6S$: 550.2138, found: 551.2208 (M+H)$^+$, 1101.4345 (2M+H)$^+$.

BB9:(S)—N-(2-((((9H-fluoren-9-yl)methoxy)carbonyl) amino)-3-(4-(tert-butoxy)phenyl)propyl)-N-((2-((tert-butoxycarbonyl)amino)ethyl)sulfonyl)glycine. $^1$H NMR (600 MHz, DMSO) δ 8.08 (s, 1H), 7.92-7.83 (m, 2H), 7.65 (t, J=6.7 Hz, 2H), 7.42 (dd, J=9.2, 5.7 Hz, 3H), 7.34 (d, J=7.2 Hz, 3H), 7.16 (d, J=8.3 Hz, 2H), 7.05 (dd, J=20.8, 7.5 Hz, 1H), 6.98 (t, J=5.2 Hz, 1H), 6.82-6.74 (m, 2H), 6.69 (dd, J=8.2, 5.2 Hz, 1H), 4.29-4.10 (m, 5H), 4.03 (d, J=18.6 Hz, 1H), 3.58-3.51 (m, 1H), 3.48-3.41 (m, 1H), 3.36 (s, 2H), 3.32-3.22 (m, 4H), 2.86 (dd, J=13.1, 10.4 Hz, 1H), 2.57 (dd, J=14.8, 8.4 Hz, 1H), 1.53 (s, 1H), 1.38 (s, 6H), 1.24 (d, J=23.0 Hz, 2H), 1.16 (s, 8H). $^{13}$C NMR (151 MHz, DMSO) δ 170.93, 170.78, 158.97, 158.73, 158.49, 158.25, 155.76, 155.36, 153.18, 143.84, 143.76, 140.72, 133.24, 133.07, 130.03, 129.66, 127.60, 127.02, 125.23, 123.39, 120.05, 116.78, 114.93, 114.85, 78.08, 77.46, 65.44, 51.33, 51.21, 48.46, 46.67, 36.96, 34.78, 33.76, 28.40, 28.13, 27.00. HRMS (ESI) (M+H)$^{+1}$ Calc. for $C_{37}H_{47}N_3O_9S$: 709.3033, found: 710.3110 (M+H)$^+$.

Other building blocks are characterized in the inventors' previous works.[7-10]

2. Preparation of VEGF Mimic γ-AA Peptide Sequences 2.1 General Information

VEGF mimic sequences were synthesized using sulfono-γ-AA peptide building blocks on 0.6 mmol/g, 200-400 mesh solid support rink-amide resin (Chem-Impex International). All peptides were analyzed and purified on a Waters Breeze 2 HPLC with an analytical column (1 mL/min) and a preparative column (16 mL/min). A linear gradient of 5-100% acetonitrile in water (0.1% TFA) for 50 min, followed by 100% acetonitrile for 10 min was used. Purified sequences were lyophilized on a Labconco freeze drying system. Masses of final VEGF mimic γ-AA peptide sequences were confirmed with High-resolution MS (HRMS) on Agilent 6540 LC/QTOF or with MALDI on Applied Biosystems 4700 Proteomics Analyzer.

2.2 Synthesis

Figure 18:
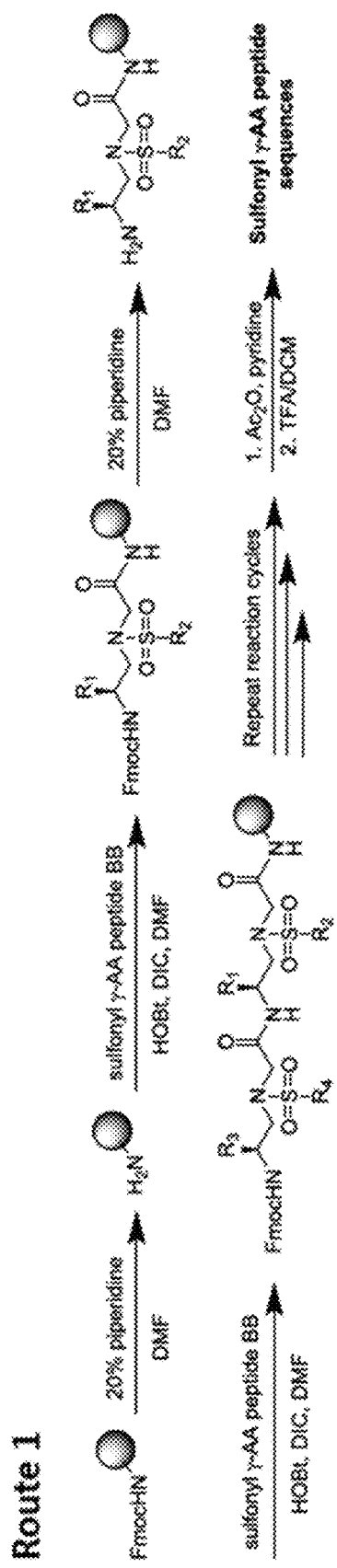
FIG. 18. General solid phase synthesis routes used to prepare VEGF-mimicking sulfono-γ-AA peptide sequences.

Solid phase peptide synthesis of VEGF mimic sulfono-γ-AA peptide sequences was carried out on 100 mg Fmoc-Rink Amide MBHA resin (0.6 mmol/g, 200-400 mesh) under room temperature and atmospheric pressure as outlined by route 1 in FIG. 18 (Scheme S$_2$). The resin was first swollen by soaking in DMF for 30 min followed by deprotection of Fmoc group by shaking in 20% piperidine/DMF (15 min×2) and washed with DCM 3x and DMF 3x. Sulfono-building blocks were coupled to the resin by adding a solution of the building block (2 equiv.), HOBt (4 equiv.) and DIC (4 equiv.) in 2 mL DMF and shaking for 4 h. The resin was then washed with DCM 3x and DMF 3x and treated with 20% piperidine/DMF (15 min×2) to remove the Fmoc protecting group. Following the same coupling procedure, a total of 8 sulfono-γ-AA peptide building blocks were coupled to the resin. The N-terminus of the sulfono-γ-AA peptide sequences were acetylated by acetic anhydride (1 ml) in pyridine (2 ml) (15 min×2) and cleaved from the resin by treating with 1:1 TFA/DCM (4 mL, 2 h). The cleavage solution was collected, and the resin was washed with 1:1 TFA/DCM 3x. The wash solutions were combined with the cleavage solution and dried under vacuum to give the crude product. Crude sequences were analyzed and purified on a Waters HPLC system with a linear gradient of 5-100% acetonitrile in water (0.1% TFA) for 50 min at a flow rate of 1 mL/min for analytical scale and 16 mL/min for preparative scale. VEGF mimic sulfono-γ-AA peptide sequences were obtained at >95% purity after prep-HPLC purification.

2.3 HPLC Traces and HRMS Spectrum

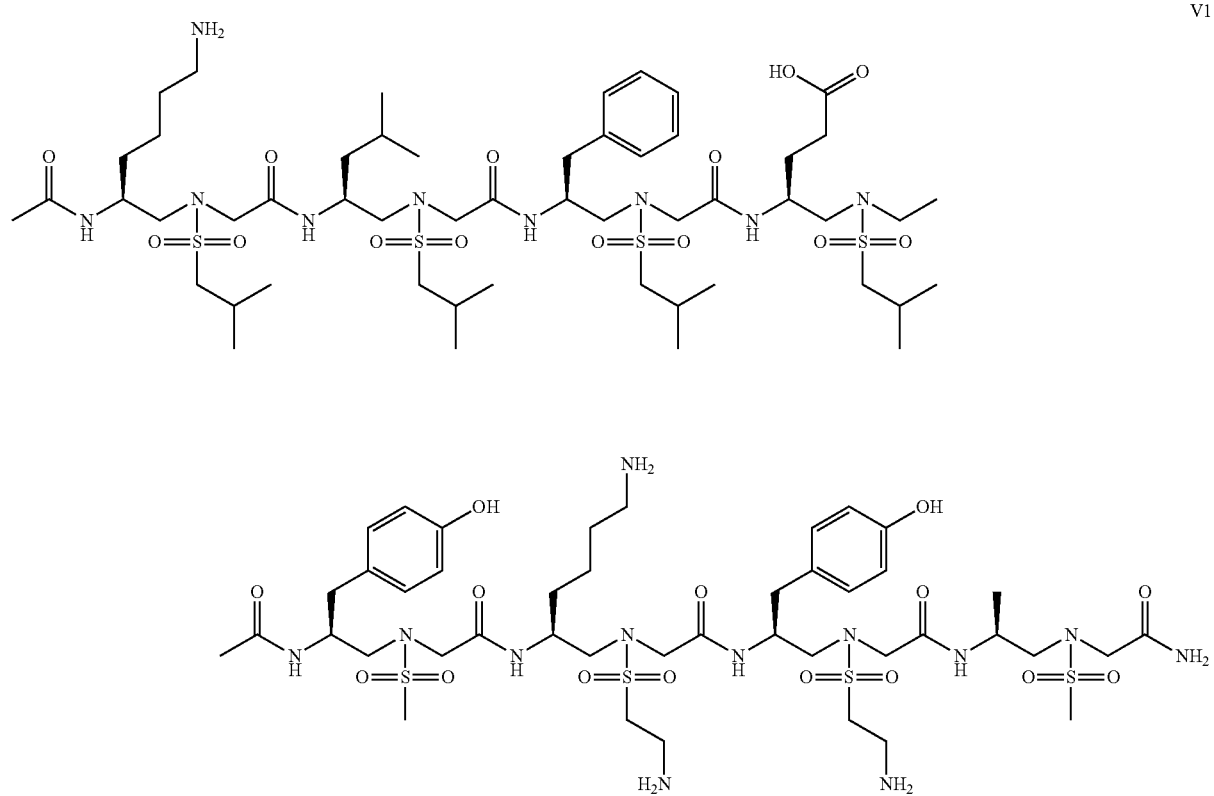

Figure 19:
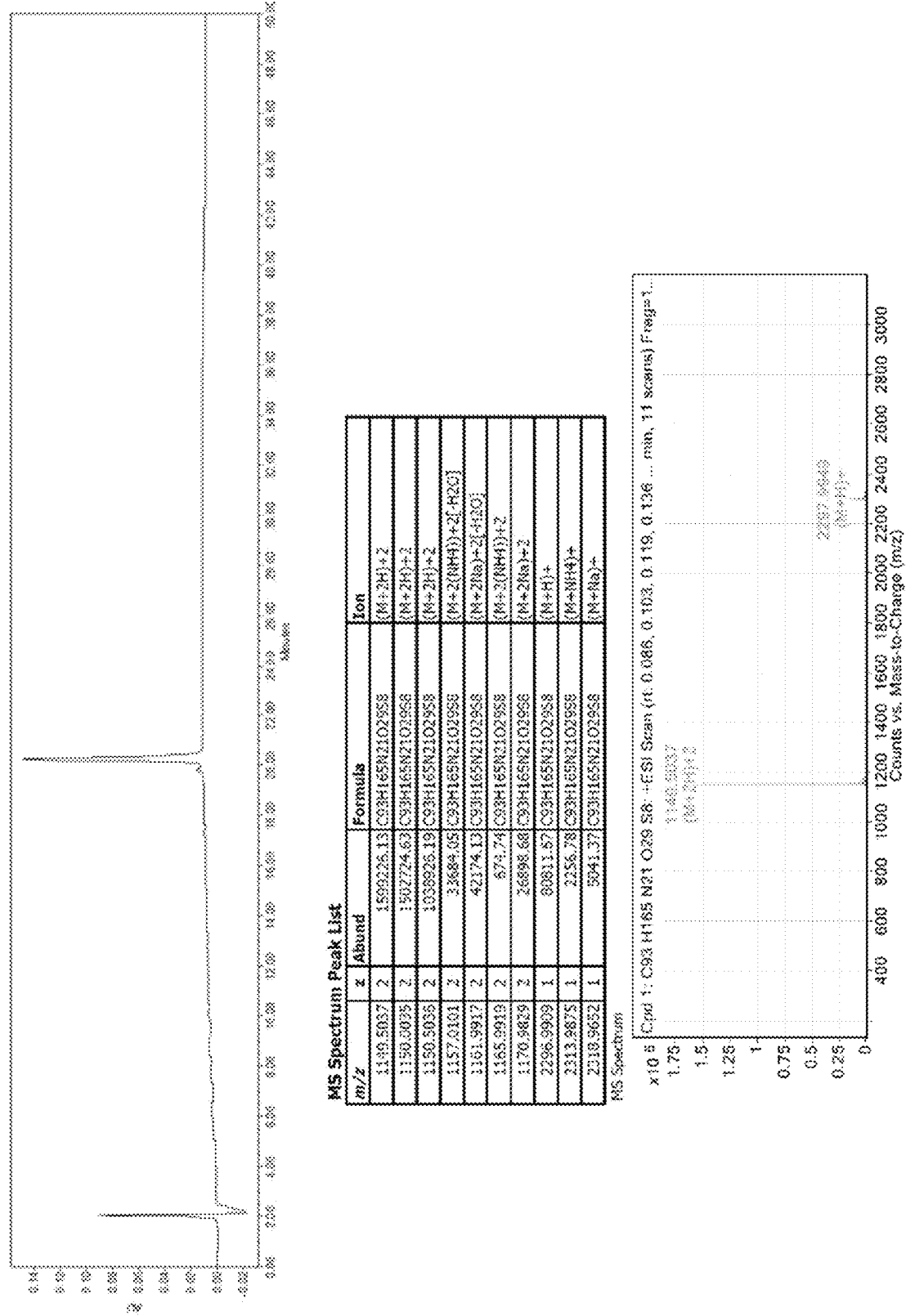
FIG. 19. HPLC Traces and HRMS Spectrum for sulfono-γ-AA peptide V1.
Figure 20:
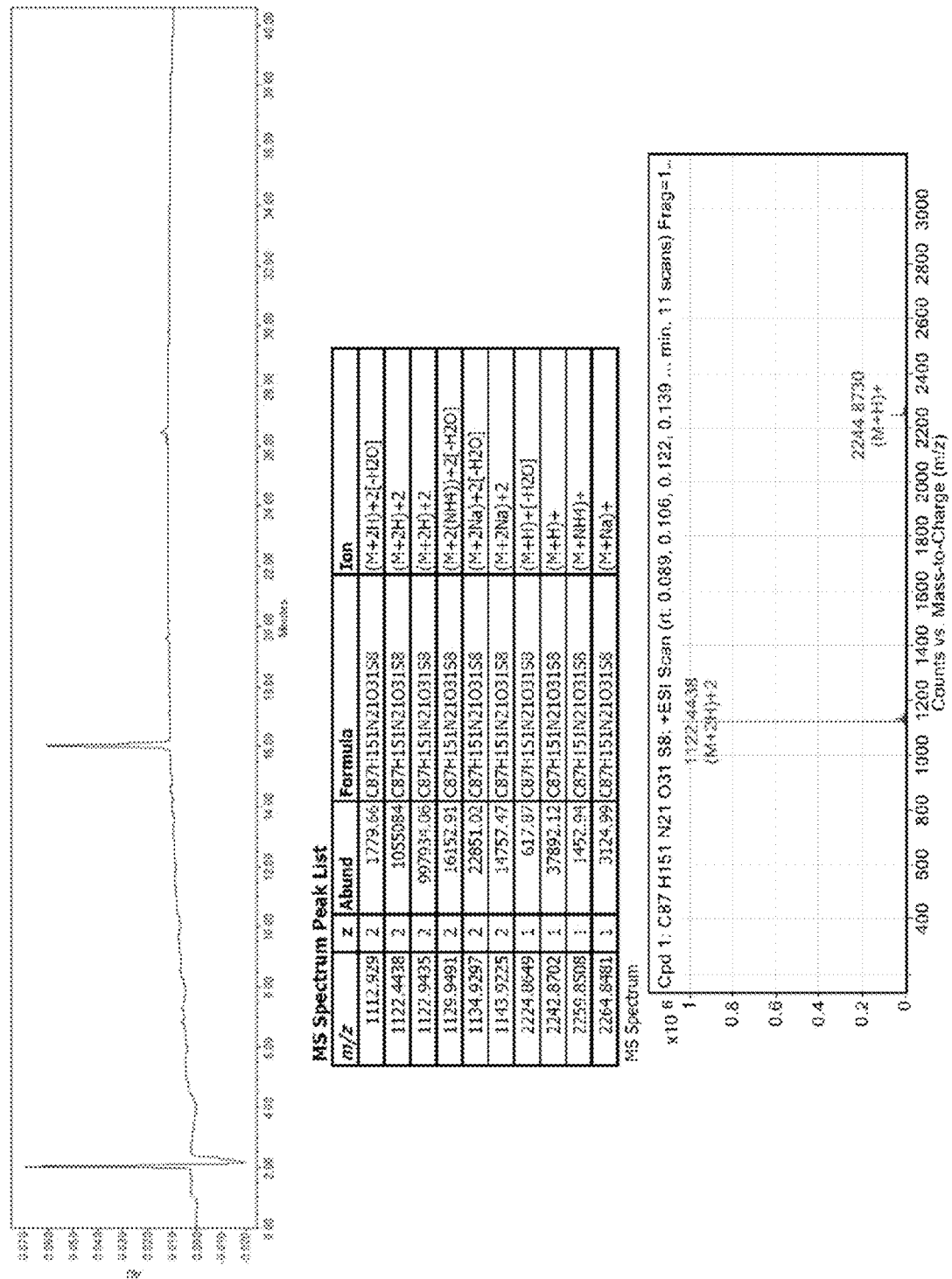
FIG. 20. HPLC Traces and HRMS Spectrum for sulfono-γ-AA peptide V2.
Figure 21:
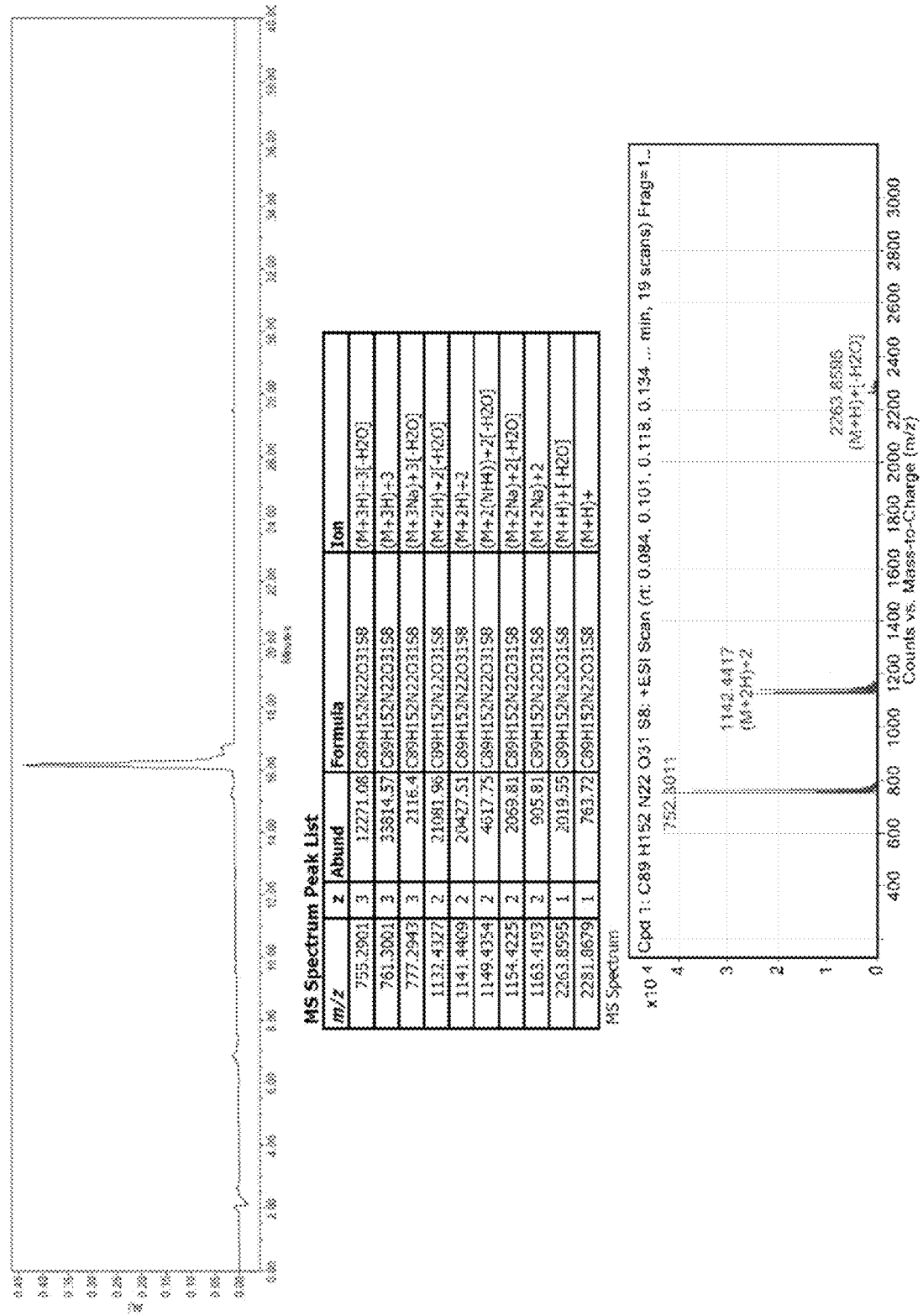
FIG. 21. HPLC Traces and HRMS Spectrum for sulfono-γ-AA peptide V3.
Figure 22:
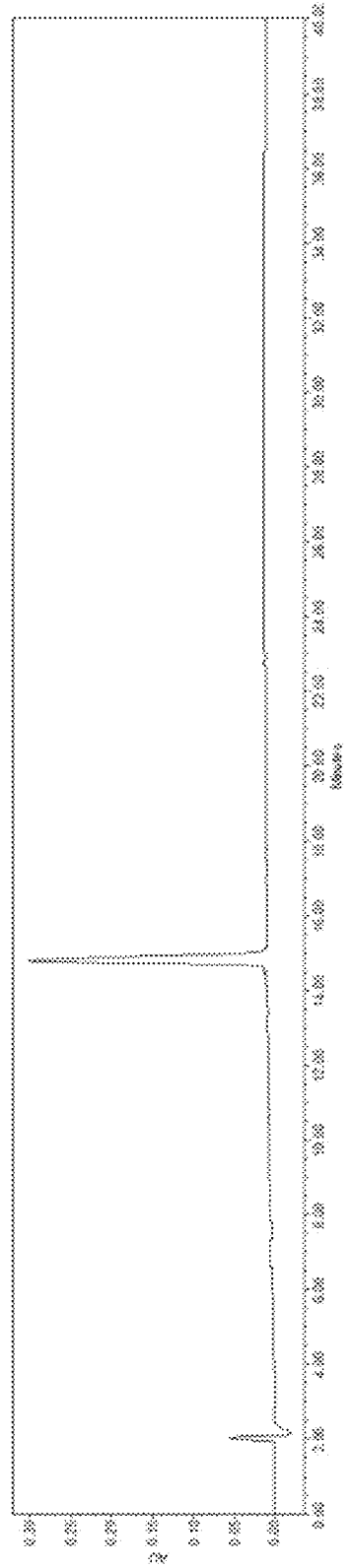
FIG. 22. HPLC Traces and HRMS Spectrum for sulfono-γ-AA peptide V4.
Figure 22:
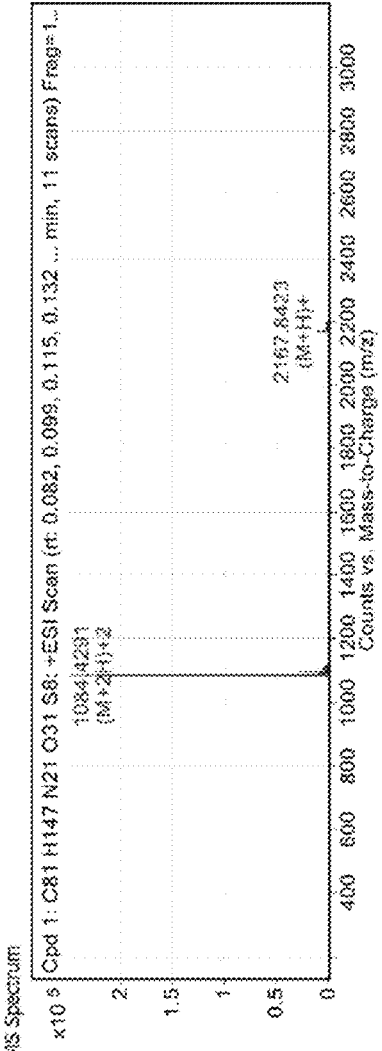
Figure 23:
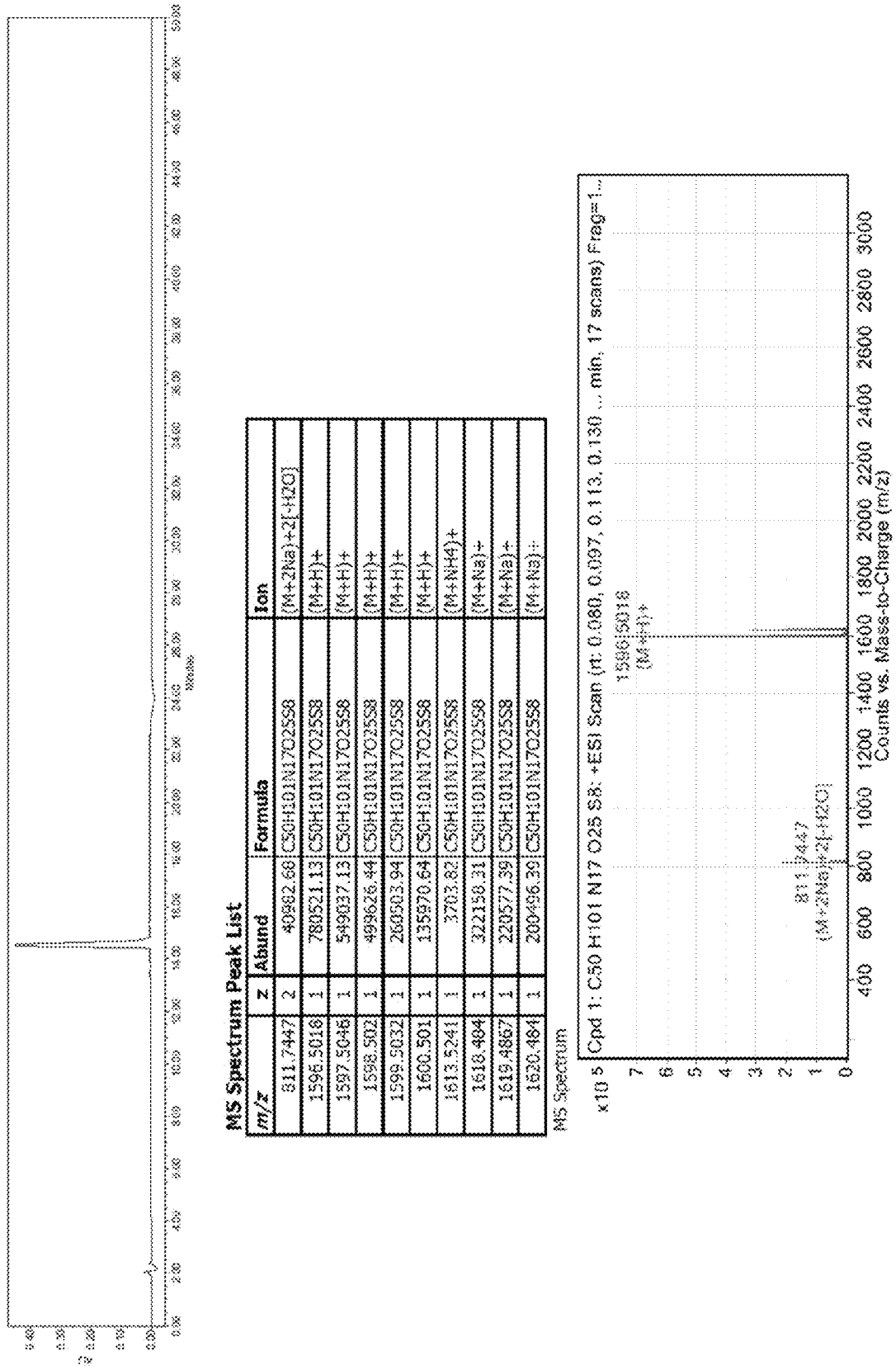
FIG. 23. HPLC Traces and HRMS Spectrum for sulfono-γ-AA peptide V5.
Figure 24:
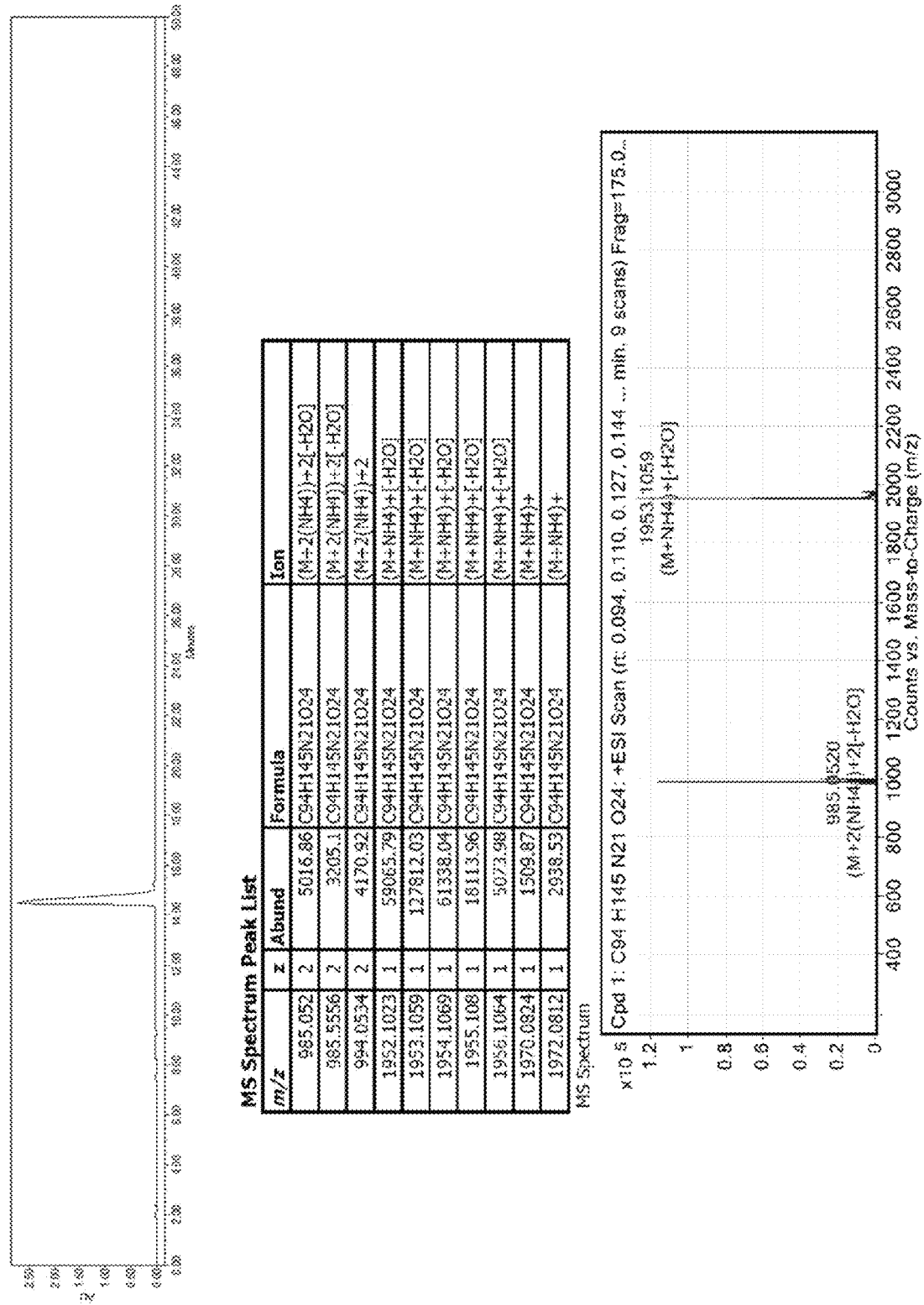
FIG. 24. HPLC Traces and HRMS Spectrum for QK.
Figure 25:
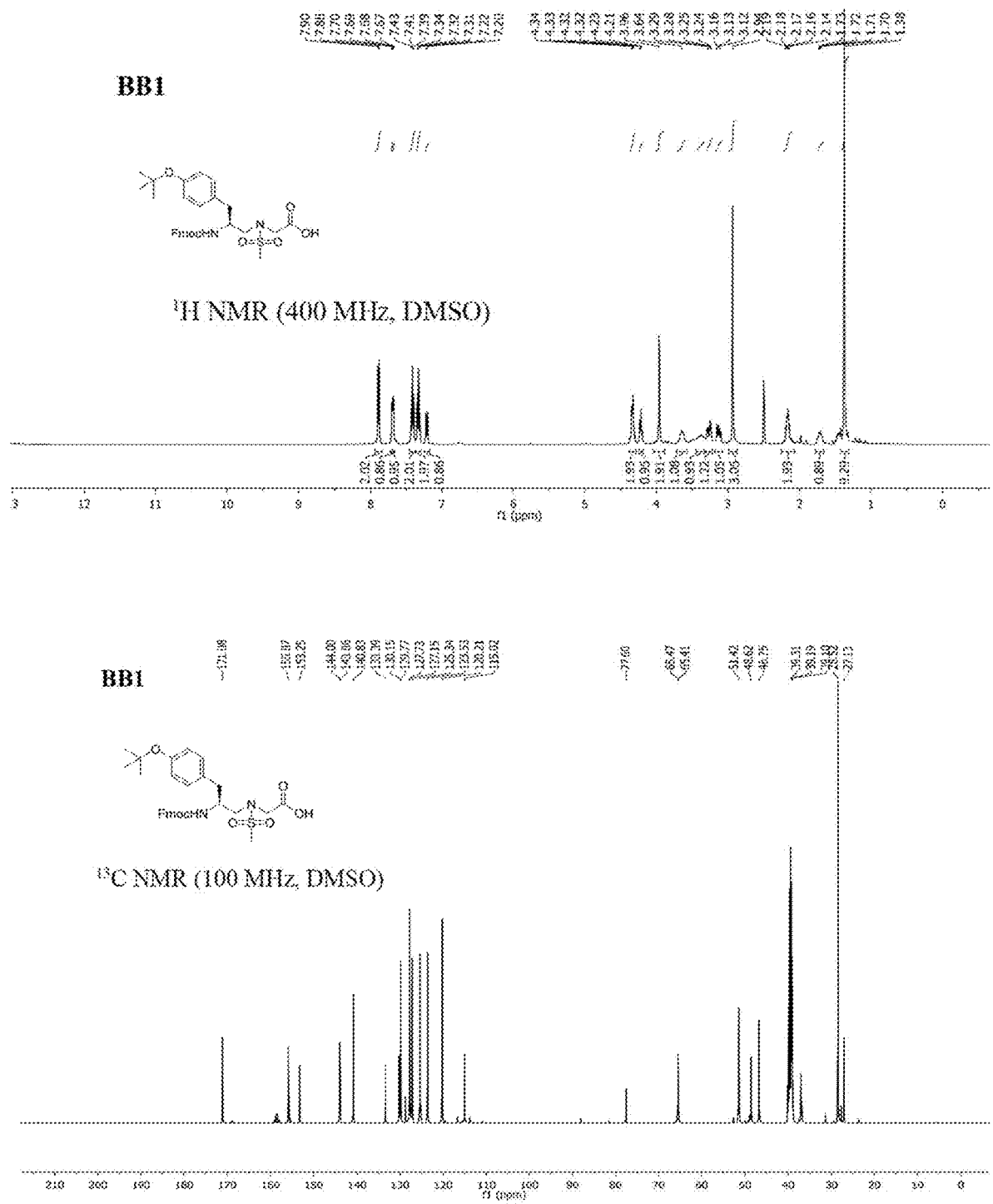
FIG. 25. 1H and 13C NMR spectra of sulfono-γ-AA peptide building block BB1.
Figure 26:
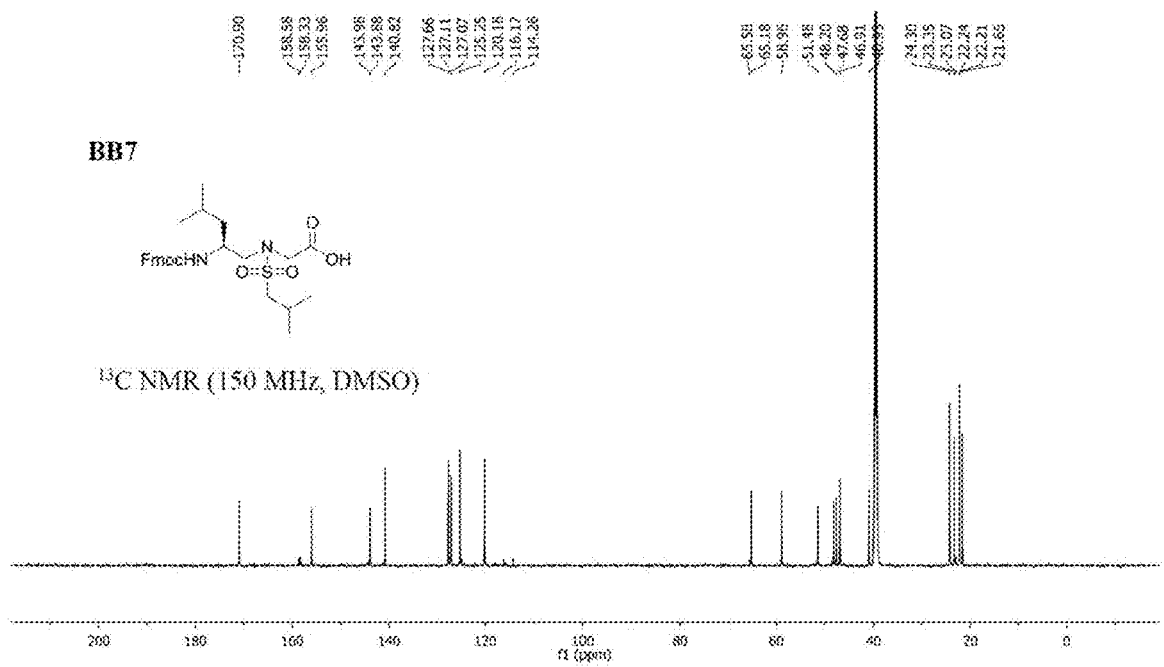
FIG. 26. 1H and 13C NMR spectra of sulfono-γ-AA peptide building block BB7.
Figure 26:
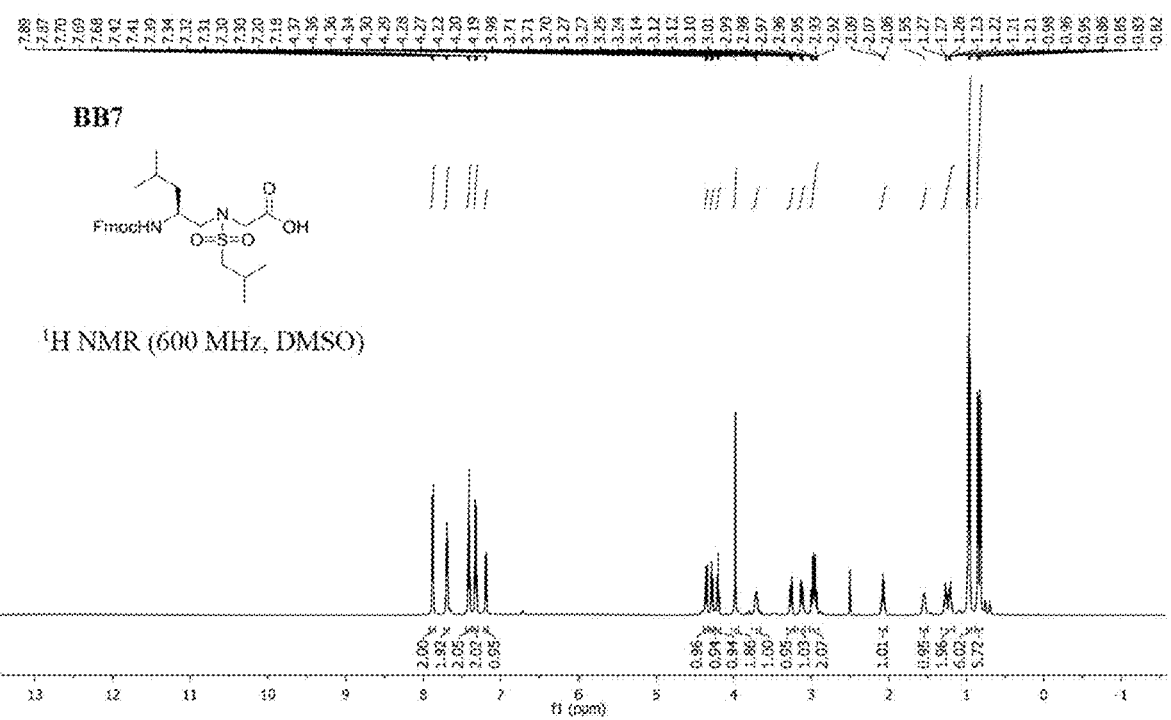
Figure 27:
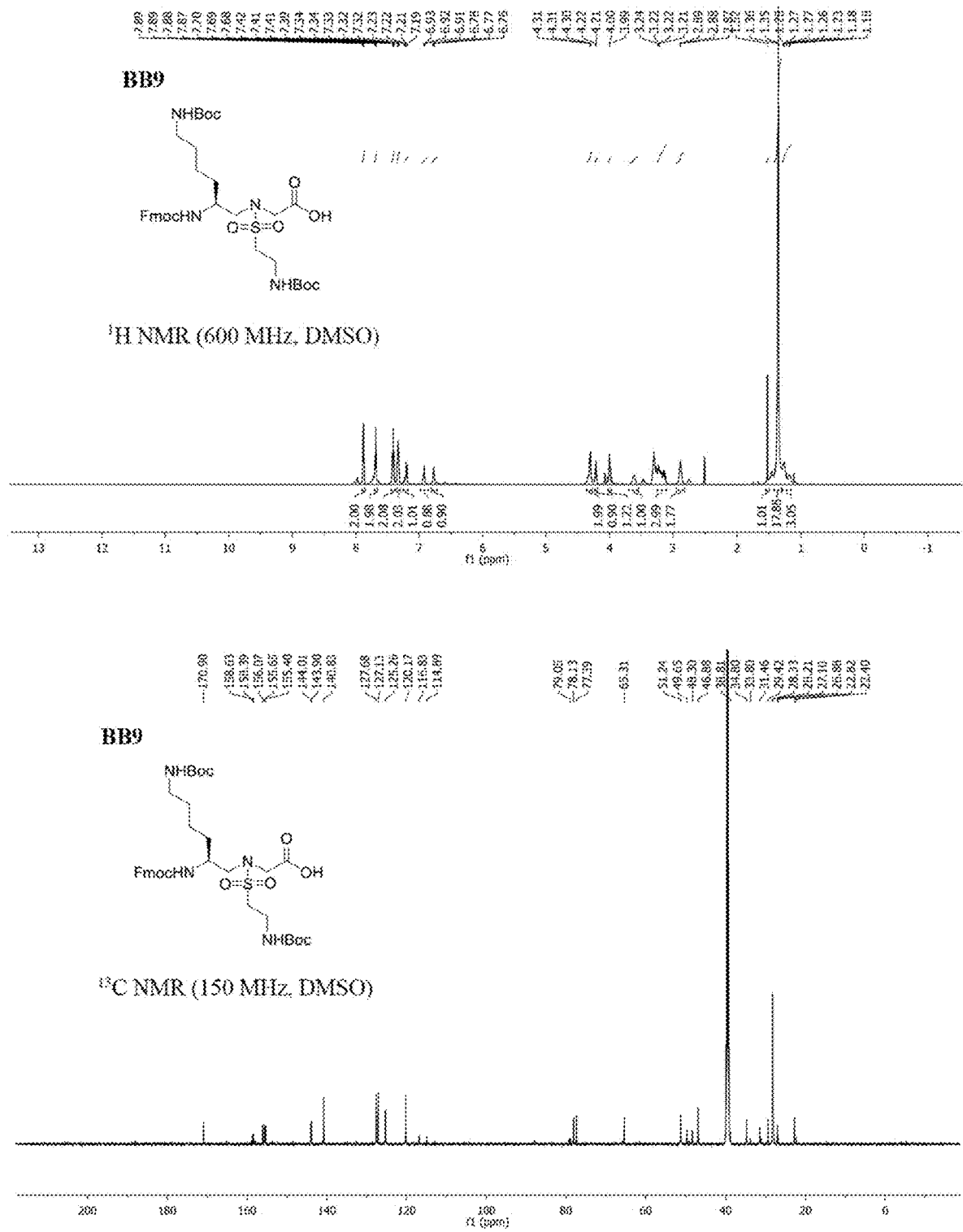
FIG. 27. 1H and 13C NMR spectra of sulfono-γ-AA peptide building block BB9.

HRMS (ESI) (M+H)$^{+1}$ Calc. for $C_{93}H_{165}N_{21}O_{29}S_8$: 2295.9848, found: 1149.5037 (M+2H)$^{+2}$, 2296.9909 (M+H)$^{+1}$, Purity 98.8% (FIG. 19).
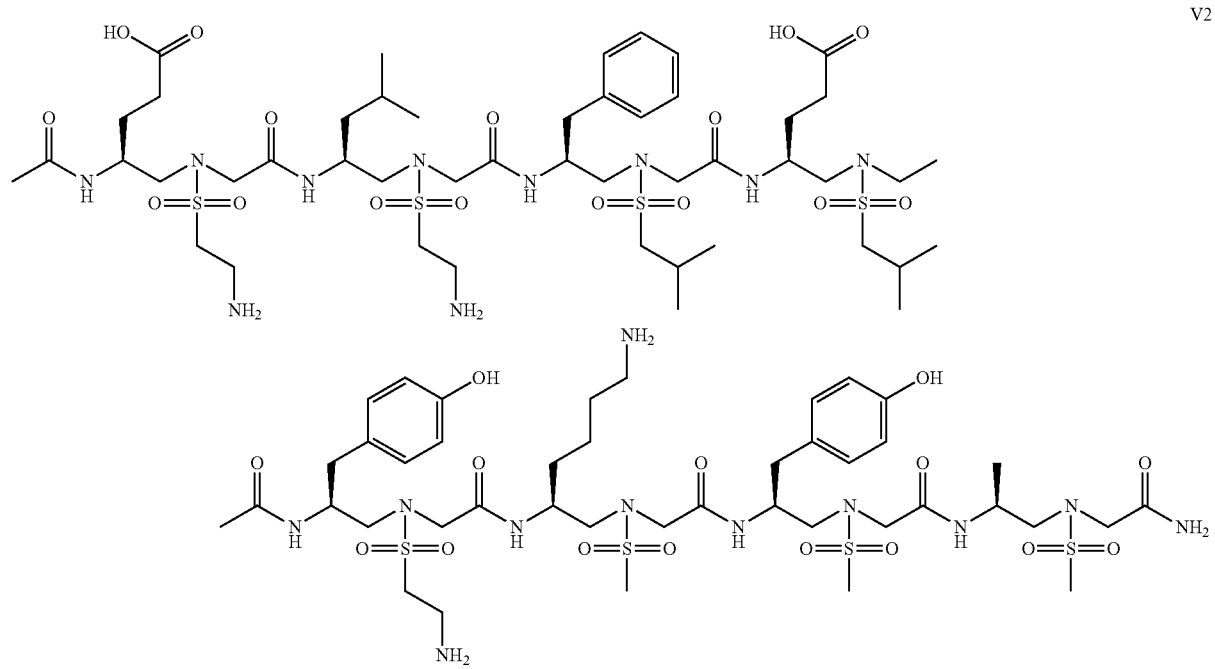
V2
HRMS (ESI) (M+H)$^{+1}$ Calc. for $C_{87}H_{151}N_{21}O_{31}S_8$: 2241.8651, found: 1122.9435 (M+2H)$^{+2}$, 2242.8702 (M+H)$^{+1}$, Purity 99.0%
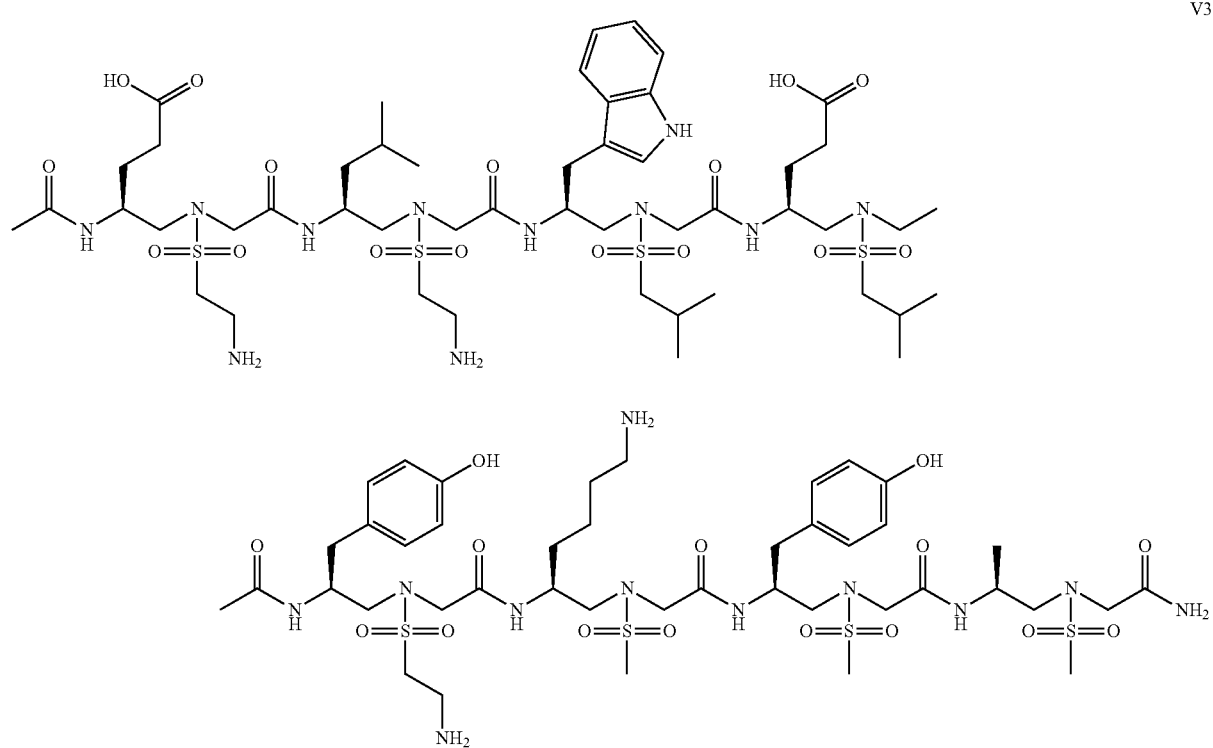
V3

HRMS (ESI) (M+H)$^{+1}$ Calc. for $C_{89}H_{152}N_{22}O_{31}S_8$: 2280.8760, found: 761.3001 (M+3H)$^{+3}$, 1141.4409 (M+2H)$^{+2}$, 2281.8679 (M+H)$^{+1}$, Purity 97.4%

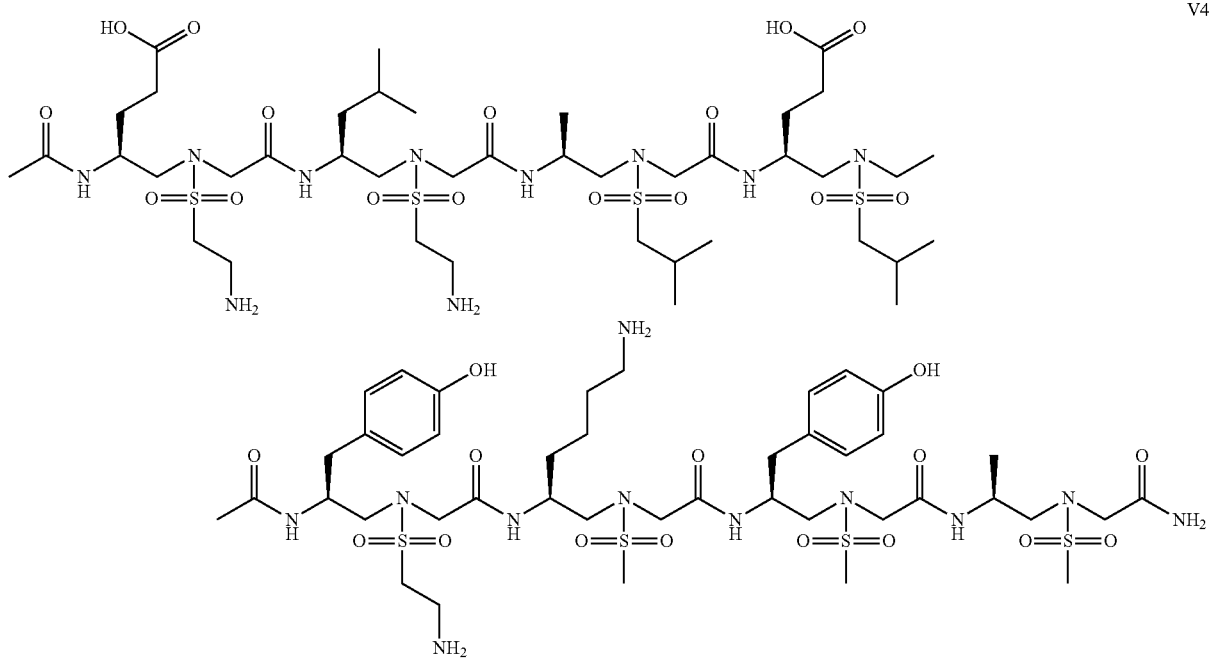

V4

HRMS (ESI) (M+H)$^{+1}$ Calc. for $C_{81}H_{147}N_{21}O_{31}S_8$: 2165.8338, found: 1084.4291 (M+2H)$^{+2}$, 2166.8381 (M+H)$^{+1}$, Purity 99.2%

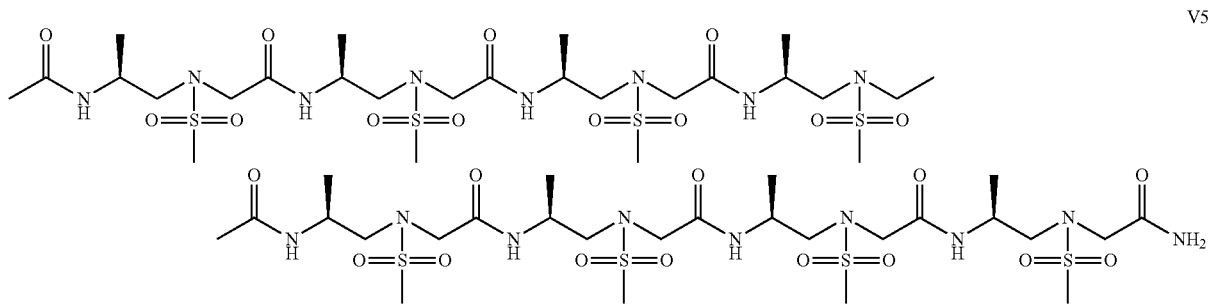

V5

HRMS (ESI) (M+H)$^{+1}$ Calc. for C50H101N17O25S8: 1595.4920, found: 1596.5018 (M+H)$^{+1}$, Purity 99.1%

Ac-KLTWQELYQLKYKGI(QK)  (SEQ ID NO: 1)

HRMS (ESI) (M+H)$^{+1}$ Calc. for C94H145N21O24: 1952.0771, found: 985.0520 (M+2H)$^{+2}$, 1953.1059 (M+H)$^{+1}$, Purity 99.1%

3. Circular Dichroism

Circular Dichroism (CD) spectra of samples were measured in PBS at 100 µM concentrations using an Aviv 215 spectrometer in a 1 mm path quartz cuvette. An average of 3 scans for each sample run was taken thrice and averaged. A PBS sample was measured the same was as a blank and subtracted from average sample readings. The equation below was used to calculate molar ellipticity [θ].

[θ]=θobs/(n×1×c×10)

θobs=measured ellipticity in millidegrees; n=number of side chains; 1=path length in centimeter (0.1 cm); c=concentration of samples (M).

4. Surface Plasmon Resonance Assay

Binding kinetics of VEGF mimics to VEGFR-1 were measured by surface plasmon resonance (SPR) using a Biacore T200 (General Electric Co.). VEGF-1 protein extracellular domain (Met 1-Asn 756) (FLT1-3809H, Creative BioMart USA) was covalently coupled to CMS chip following manufacturer's instructions. Samples were prepared in RBS-EP+ buffer (pH 7.4) at different concentration and flowed over the sensor chip to interact with the immobilized protein, followed by the running buffer. The dissociation data was collected, and a different concentration was assayed after redundant samples were removed from the protein by treating with KCl (1 M). The final binding kinetics was obtained by fitting using the T200 software with a one-to-one binding model. Binding affinities of mimic sequences to VEGFR-2 were measured using VEGFR-2 extracellular domain (Met 1-Glu 764) (KDR-6966H, Creative BioMart USA) in a similar fashion.

5. In Vitro Angiogenesis Assays 5.1 Cell Migration Assay

Cell migration assay was performed in triplicates on Transwell permeable support, 8.0 μm pore (Corning, USA). Serum starved $5 \times 10^4$ human umbilical endothelial cells (HUVECs) in endothelial basal medium (EBM) (Endothelial Cell Growth Medium BulletKit, Lonza Catalog: CC-3124, USA) were seeded on the permeable support and allowed to migrate through the membrane that was placed in the Transwell containing 500 μL of endothelial cell growth medium (EGM), 1% FBS with or without 50 ng/mL $VEGF_{165}$ (Bon Opus Biosciences) and mimic sequences. Following the incubation of the Transwell for 12 h, cells on the top surface of the membrane were removed with cotton swaps. Migrated cells at the bottom of the membrane were fixed with 4% paraformaldehyde and stained with Crystal Violet at 37° C. for 20 min and 10 min respectively and counted with Nikon Inverted Microscope ECLIPSE Ti-U.

5.2 Wound Healing

HUVEC cells ($10^5$) were seeded on a 12 well tissue culture plate and allowed to grow for 12 h. The attached cells were then scratched with a sterile 200 mL pipette tip and treated with mimic sequences (10 μM) and/or $VEGF_{165}$ (50 ng/mL) in serum free medium. Plates were incubated at 37° C. and 5% CO2 and cell migration was observed with a Nikon Inverted Microscope ECLIPSE Ti-U at 0 and 24 h. The wound widths were measured by ImageJ (version 1.50).

5.3 Capillary Tube Formation Assay

Nutrient starved HUVECs, for 24 h in 0.5% FBS (sEBM) endothelial basal medium (EBM), were harvested and resuspended in 10% FBS (mEGM) endothelial growth medium. Cells were then seeded in 48 well plate coated with basement membrane extract (BME). To prepare the plates, Costar48 well culture plates were coated with basement membrane (Corning Matrigel Basement Membrane Matrix LDEV-free, 354234) and incubated for 30 min at 37° C. $5 \times 10^4$ cells were seeded in each well and treated with VEGF mimic sequences and/or $VEGF_{165}$, or left untreated. Formation or lack thereof of tube-like structures was monitored over a 24 h period with a Nikon Inverted Microscope ECLIPSE Ti-U.

5.4 Western Blot Assay

HUVECs ($1 \times 10^6$) were starved for 24 h and treated with a V1, V2, V3 and QK in the presence or absence of VEGF-A165 at 37° C. for 24 h. Cells were then lysed with a lysis buffer containing Protease and Phosphatase Inhibitor (Thermo Scientific) to obtain total cellular proteins, and the amount of protein was quantified using the BCA Protein Assay Kit (Thermo Scientific, Waltham, MA). Proteins were then denatured by boiling at 100° C. for 10 min in the sample buffer and separated by electrophoresis on 10% SDS-polyvinylamide minigels. Target proteins were transferred to polyvinylidene difluoride membranes and blocked with 5% BSA in TBST solution for 1 h and then washed three times with TBST (5 min each time). After incubation with primary antibodies (P-VEGFR2 antibody, Cell Signaling Technology; T-VEGFR2 antibody, Cell Signaling Technology; p-AKT antibody, Cell Signaling Technology; T-AKT antibody, Cell Signaling Technology; 1:1000 dilution) overnight at 4° C., the membranes were washed three times with TBST and incubated with secondary antibodies (1:5000) at room temperature for 1 h followed by washing with TBST and ECL detection.

6. Immunofluorescence Binding Assay

HUVEC cells grown in m-Dish 35 mm, high Glass Bottom (#81158 Ibidi) were treated with V2 and V3 overnight at 37° C. Cells were then washed with TBST twice and fixed with 4% formaldehyde solution (Fisher Chemical) for 20 min at room temperature. This was followed by TBST wash twice and blocking with TBST—5% BSA blocking solution for 1 h at room temperature. After washing the cells with TBST three times, the cells were incubated with anti-VEGFR-1 antibody (Proteintech) and anti-VEGFR-2 antibody (Invitrogen) overnight at 4° C. After washing with TBST three times, cells were stained with FITC labeled secondary antibody (Invitrogen) for 1 h at room temperature and counterstained with DAPI (Invitrogen). A Nikon fluorescence microscope was used for imaging cells and image analysis was done with Image J software (ImageJ 5.53e, National Institute of Health, USA).

7. Enzyme Stability Assay

Enzyme stability test was conducted in pronase (Roche Diagnostics GmbH, Germany). 0.1 mg/mL of mimic sequences were incubated with 0.1 mg/mL pronase in 100 mM ammonium bicarbonate buffer (pH 7.8, 37° C.). Controls were prepared for each sample in the same way without pronase. After 24 h, samples were dried with speed vacuum and reconstituted in water-acetonitrile (1:1) solvent. Analysis was carried out on a Waters Breeze 2 HPLC system with an analytical column with 1 mL/min flow rate and linear gradient of 5-100% acetonitrile in water (0.1% TFA) for 50 min.

8. Superimposition of Sulfono-γ-AA Peptides with VEGF-α1 Helix

The helical structures of Sulfono-γ-AA peptides V2 and V3 were built on the reported crystal structure of Sulfono-γ-AA peptides (CCDC: 1841094)[5] and side chains were built with desired ones for V2 and V3 by using PyMOL software.[6,7] The structures were subsequently overlaid with VEGF-al helix, and then compared their interaction with VEGFR1 or VEFR2, respectively.

References for Example 2

1. Wu, H.; Qiao, Q.; Hu, Y.; Teng, P.; Gao, W.; Zuo, X.; Wojtas, L.; Larsen, R. W.; Ma, S.; Cai, J., Sulfono-γ-AApeptides as a New Class of Nonnatural Helical Foldamer. Chemistry—A European Journal 2015, 21 (6), 2501-2507.
2. Teng, P.; Ma, N.; Cerrato, D. C.; She, F.; Odom, T.; Wang, X.; Ming, L. J.; van der Vaart, A.; Wojtas, L.; Xu, H.; Cai, J., Right-Handed Helical Foldamers Consisting of De Novo d-AApeptides. J. Am. Chem. Soc. 2017, 139, 7363.

3. Teng, P.; Gray, G. M.; Zheng, M.; Singh, S.; Li, X.; Wojtas, L.; van der Vaart, A.; Cai, J., Orthogonal Halogen-Bonding-Driven 3D Supramolecular Assembly of Right-Handed Synthetic Helical Peptides. Angew. Chem., Int. Ed. 2019, 58, 7778.
4. Sang, P.; Shi, Y.; Lu, J.; Chen, L.; Yang, L.; Borcherds, W.; Abdulkadir, S.; Li, Q.; Daughdrill, G.; Chen, J., α-Helix-mimicking sulfono-γ-AApeptide inhibitors for p53—MDM2/MDMX protein-protein interactions. J. Med. Chem. 2020, 63 (3), 975-986.
5. She, F.; Teng, P.; Peguero-Tejada, A.; Wang, M.; Ma, N.; Odom, T.; Zhou, M.; Gjonaj, E.; Wojtas, L.; van der Vaart, A.; Cai, J., De Novo Left-Handed Synthetic Peptidomimetic Foldamers. Angew. Chem. Int. Ed. 2018, 57 (31), 9916-9920.
6. Sang, P.; Zhang, M.; Shi, Y.; Li, C.; Abdulkadir, S.; Li, Q.; Ji, H.; Cai, J., Inhibition of β-catenin/B cell lymphoma 9 protein-protein interaction using α-helix—mimicking sulfono-γ-AApeptide inhibitors. Proc. Natl. Acad. Sci. 2019, 116 (22), 10757-10762.
7. Sang, P.; Zhou, Z.; Shi, Y.; Lee, C.; Amso, Z.; Huang, D.; Odom, T.; Nguyen-Tran, V.; Shen, W.; Cai, J., The Activity of Sulfono-γ-AApeptide Helical Foldamers That Mimic GLP-1. Sci. Adv. 2020, 6, eaaz4988.
8. Sang, P.; Zhang, M.; Shi, Y.; Li, C.; Abdulkadir, S.; Li, Q.; Ji, H.; Cai, J., Inhibition of β-catenin/B Cell Lymphoma 9 Protein-protein Interaction using α-helix—mimicking Sulfono-γ-AApeptide Inhibitors. Proc. Natl. Acad. Sci. U.S.A. 2019, 116, 10757.
9. Bolarinwa, 0.; Zhang, M.; Mulry, E.; Lu, M.; Cai, J., Sulfono-γ-AA modified peptides that inhibit HIV-1 fusion. Org. Biomol. Chem. 2018, 16 (42), 7878-7882.
10. Sang, P.; Shi, Y.; Lu, J.; Chen, L.; Yang, L.; Borcherds, W.; Abdulkadir, S.; Li, Q.; Daughdrill, G.; Chen, J.; Cai, J., α-Helix-Mimicking Sulfono-γ-AApeptide Inhibitors for p53—MDM2/MDMX Protein-Protein Interactions. J. Med. Chem. 2020, 63, 975.

We claim:

1. A sulfono-γ-AA peptide according to Formula 1 and having the structure:

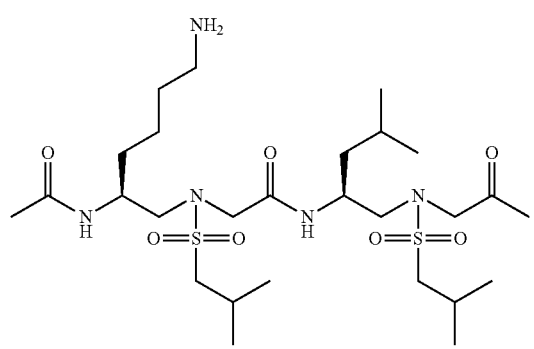

Formula 1

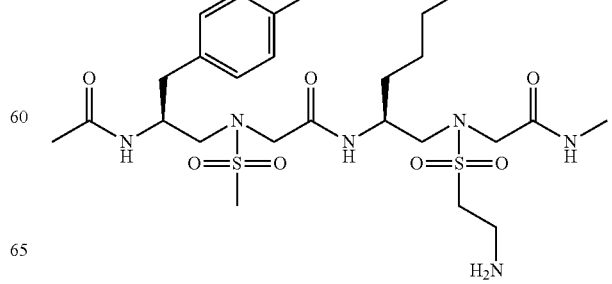

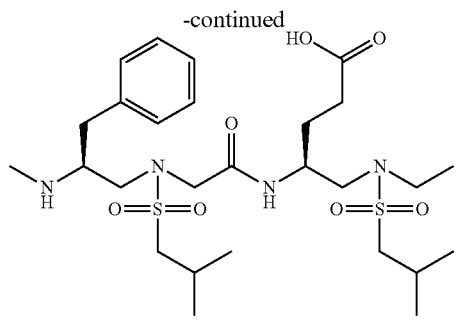

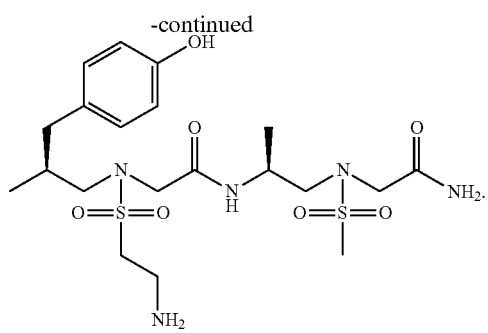

2. A method of reducing cell migration in a population of cells, the method comprising administering to the cells the sulfono-γ-AA peptide of claim 1.

3. A method of reducing capillary tube formation in a population of cells, the method comprising administering to the cells the sulfono-γ-AA peptide of claim 1.

4. A pharmaceutical composition comprising:
the sulfono-γ-AA peptide of claim 1; and
a pharmaceutically acceptable carrier.

5. The pharmaceutical composition of claim 4, further comprising at least one of:
a sulfono-γ-AA peptide according to Formula 3 and having the structure:

Formula 3

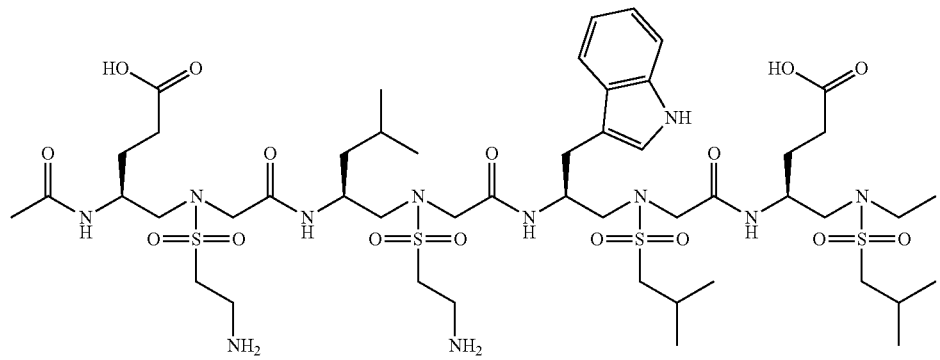

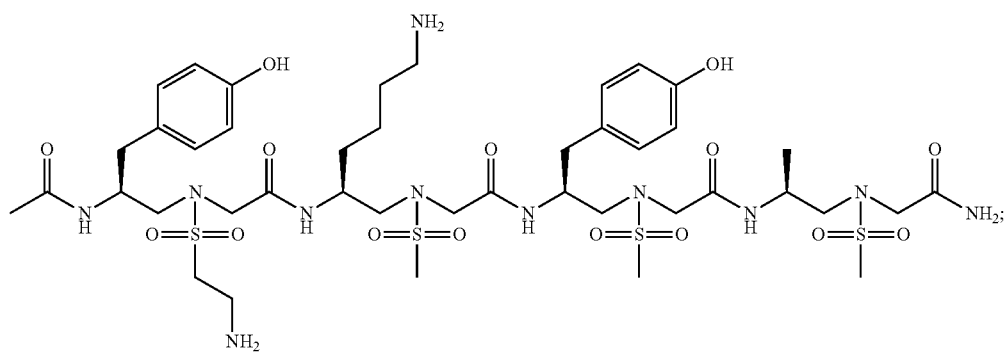

and
a sulfono-γ-AA peptide according to Formula 2 and having the structure:

Formula 2

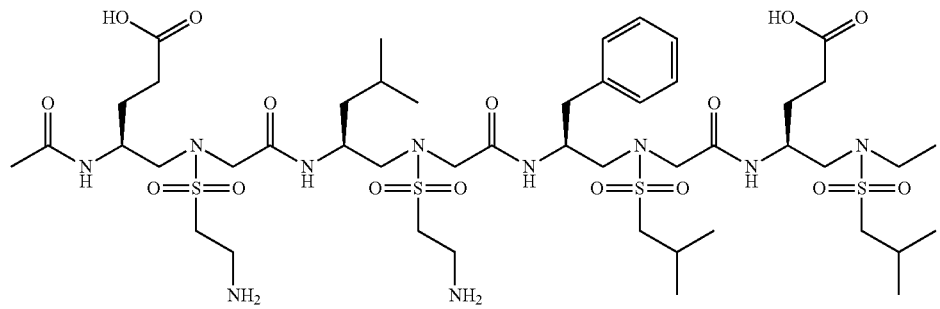

-continued

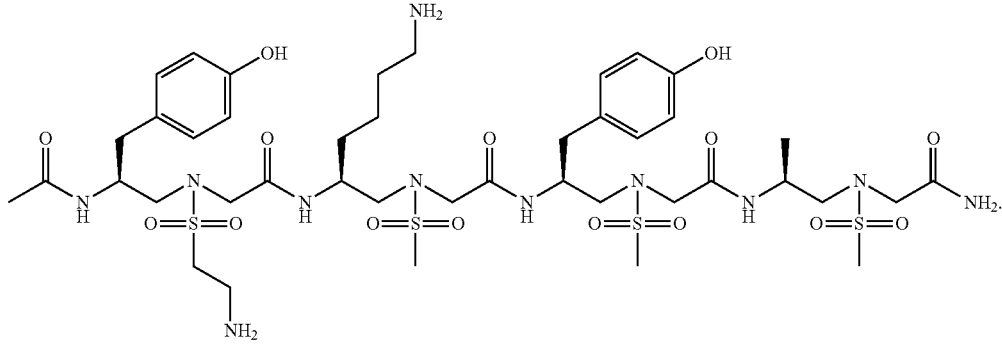

6. A method of reducing angiogenesis in a subject in need thereof comprising administering to the subject a therapeutically acceptable amount of the pharmaceutical composition of claim 4.

7. The method of claim 6, wherein the subject in need thereof has, or is suspected of having, a cancer or retinopathy.

8. A sulfono-γ-AA peptide according to Formula 3 and having the structure:

Formula 3

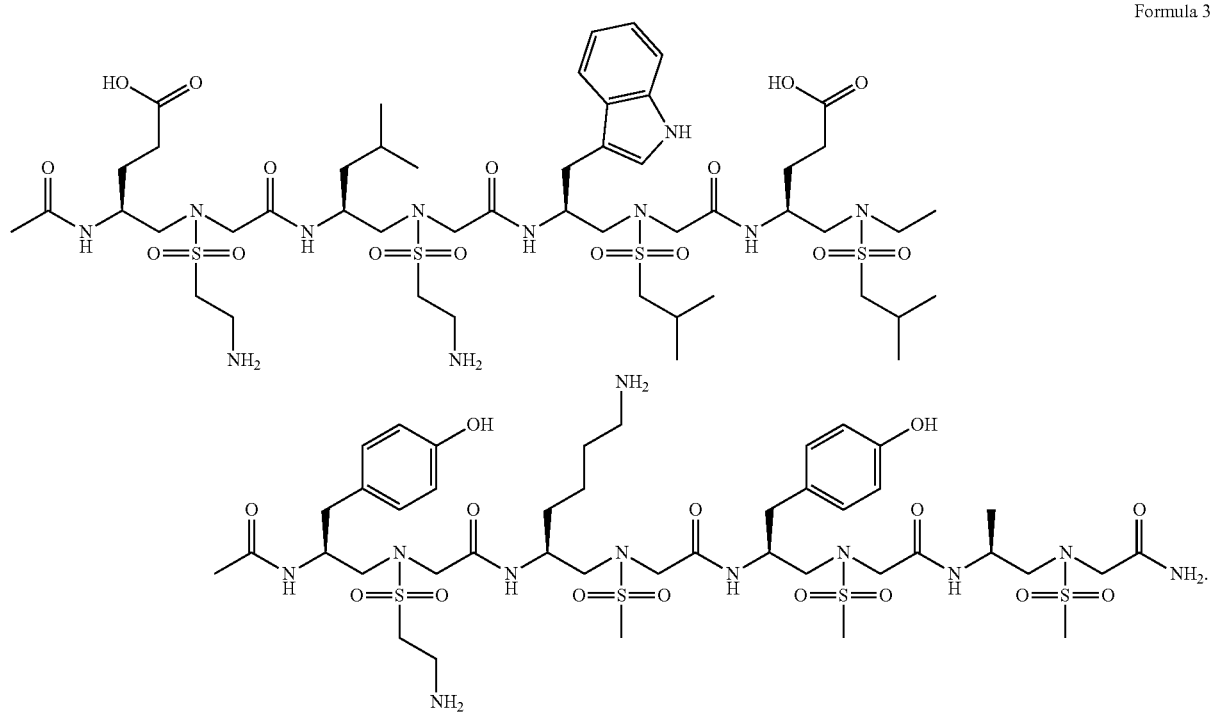

9. A method of reducing cell migration in a population of cells, the method comprising administering to the cells the sulfono-γ-AA peptide of claim 8.

10. A method of reducing capillary tube formation in a population of cells, the method comprising administering to the cells the sulfono-γ-AA peptide of claim 8.

11. A pharmaceutical composition comprising:
the sulfono-γ-AA peptide of claim 8; and
a pharmaceutically acceptable carrier.

12. A method of reducing angiogenesis in a subject in need thereof comprising administering to the subject a therapeutically acceptable amount of the pharmaceutical composition of claim 11.

13. The method of claim 12, wherein the subject in need thereof has, or is suspected of having, a cancer or retinopathy.

14. A sulfono-γ-AA peptide according to Formula 2 and having the structure:

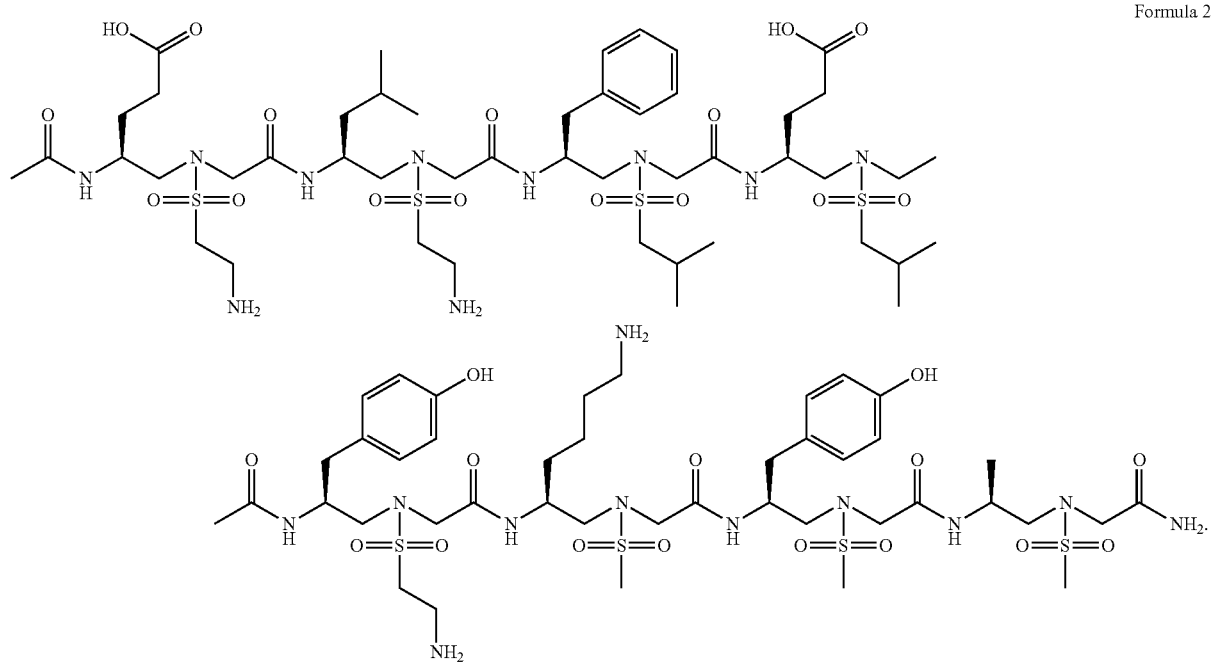

Formula 2

15. A method of increasing cell migration in a population of cells, the method comprising administering to the cells the sulfono-γ-AA peptide of claim 14.

16. A method of increasing capillary tube formation in a population of cells, the method comprising administering to the cells the sulfono-γ-AA peptide of claim 14.

17. A pharmaceutical composition comprising:
the sulfono-γ-AA peptide of claim 14; and
a pharmaceutically acceptable carrier.

18. A method of increasing angiogenesis in a subject in need thereof comprising administering to the subject a therapeutically acceptable amount of the pharmaceutical composition of claim 17.

19. The method of claim 18, wherein the subject in need thereof has, or is suspected of having, ischemic heart disease.

20. The method of claim 18, wherein the subject in need thereof has a wound or damage to an organ.

* * * * *

SEQUENCE LISTING

```
Sequence total quantity: 2
SEQ ID NO: 1           moltype = AA  length = 15
FEATURE                Location/Qualifiers
source                 1..15
                       mol_type = protein
                       organism = synthetic construct
SEQUENCE: 1
KLTWQELYQL KYKGI                                                          15

SEQ ID NO: 2           moltype = AA  length = 15
FEATURE                Location/Qualifiers
source                 1..15
                       mol_type = protein
                       organism = synthetic construct
SEQUENCE: 2
KLTWMELYQL AYKGI                                                          15
```